US012105091B2

(12) United States Patent
Hendrix et al.

(10) Patent No.: US 12,105,091 B2
(45) Date of Patent: Oct. 1, 2024

(54) USAGES OF RECOMBINANT EXTRACELLULAR VESICLES

(71) Applicants: VIB VZW, Ghent (BE); Universiteit Gent, Ghent (BE)

(72) Inventors: An Hendrix, Heusden (BE); Olivier De Wever, Heusden (BE); Edward Geeurickx, Ghent (BE); Joke Vandesompele, Zulte (BE); Pieter Mestdagh, Bruges (BE); Sven Eyckerman, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 1037 days.

(21) Appl. No.: 16/761,786

(22) PCT Filed: Nov. 6, 2018

(86) PCT No.: PCT/EP2018/080299
§ 371 (c)(1),
(2) Date: May 5, 2020

(87) PCT Pub. No.: WO2019/091964
PCT Pub. Date: May 16, 2019

(65) Prior Publication Data
US 2021/0181201 A1    Jun. 17, 2021

(30) Foreign Application Priority Data

Nov. 9, 2017   (EP) .................................... 17200743

(51) Int. Cl.
*G01N 33/58* (2006.01)
*C07K 14/16* (2006.01)
(Continued)

(52) U.S. Cl.
CPC ......... *G01N 33/582* (2013.01); *C07K 14/161* (2013.01); *C07K 14/43595* (2013.01);
(Continued)

(58) Field of Classification Search
CPC ............ C07K 14/161; C07K 14/43595; C07K 2319/60; C12Q 1/6876; C12Q 2600/158;
(Continued)

(56) References Cited

U.S. PATENT DOCUMENTS

| 2013/0078658 A1 | 3/2013 | Park et al. |
| 2013/0157300 A1 | 6/2013 | Park et al. |
| 2013/0302822 A1 | 11/2013 | Kim et al. |

FOREIGN PATENT DOCUMENTS

WO           00/68248 A2     11/2000

OTHER PUBLICATIONS

Hurwitz, S.N., Meckes, D.G. (2017). An Adaptable Polyethylene Glycol-Based Workflow for Proteomic Analysis of Extracellular Vesicles. In: Kuo, W., Jia, S. (eds) Extracellular Vesicles. Methods in Molecular Biology, vol. 1660. Humana Press, New York, NY. https://doi.org/10.1007/978-1-4939-7253-1_25 (Year: 2017).*

(Continued)

*Primary Examiner* — Jeremy C Flinders
(74) *Attorney, Agent, or Firm* — TraskBritt

(57) ABSTRACT

This disclosure relates to the field of research and clinical usage of extracellular vesicles. More in particular, this disclosure relates to usages of recombinant extracellular vesicles comprising a) a self-assembling protein that directs its own release through vesicles as a luminal membrane-bound protein and b) a heterologous marker. Indeed, the disclosure provides recombinant extracellular vesicles that can be used as a biological reference material in methods to quantify extracellular vesicles in a sample, and/or, that can be used to calibrate a device for sample extracellular (Continued)

vesicles analysis, and/or, that can be used to evaluate the isolation process of extracellular vesicles. This disclosure thus relates to improving the accuracy of an extracellular vesicle-based diagnosis.

18 Claims, 42 Drawing Sheets

Specification includes a Sequence Listing.

(51) Int. Cl.
| | |
|---|---|
| C07K 14/435 | (2006.01) |
| C12Q 1/6876 | (2018.01) |
| G01N 21/64 | (2006.01) |
| G01N 33/53 | (2006.01) |

(52) U.S. Cl.
CPC ....... C12Q 1/6876 (2013.01); G01N 21/6428 (2013.01); G01N 33/5308 (2013.01); C07K 2319/60 (2013.01); C12Q 2600/158 (2013.01); G01N 2021/6439 (2013.01); G01N 2496/30 (2013.01)

(58) Field of Classification Search
CPC ........... G01N 21/6428; G01N 33/5308; G01N 33/533; G01N 33/582; G01N 2021/6439; G01N 2496/30
See application file for complete search history.

(56) References Cited

OTHER PUBLICATIONS

Bieniasz "Late budding domains and host proteins in enveloped virus release" Virology 344, 55-63 (2006) accepted Sep. 14, 2005.
Blanc et al. "Reticulocyte-secreted exosomes bind natural IgM antibodies: Involvement of a ROS-activatable endosomal phospholipase iPLA2" Blood 110, 3407-3416 (Nov. 2007).
Brock et al. "Liquid biopsy for cancer screening, patient stratification and monitoring" Transl. Cancer Res. 4, 280-290 (Jun. 2015).
Collins et al. "A branched DNA signal amplification assay for quantification of nucleic acid targets below 100 molecules/ml" Nucleic Acids Research vol. 25, No. 15 (Jun. 1997) pp. 2979-2984.
Comas-Garcia et al. "Efficient support of virus-like particle assembly by the HIV-1 packaging signal" Elife 7, (Aug. 2018) 11 pages.
Crowley et al. "Liquid biopsy: monitoring cancer-genetics in the blood" Nat. Rev. Clin. Oncol. 10, 472-484 (Jul. 2013).
Eyckerman et al. "Trapping mammalian protein complexes in viral particles" Nat. Commun. 7, 11416 (Apr. 2016).
Fisher et al. "Intracellular disposition and metabolism of fluorescently-labeled unmodified and modified oligonucleotides microinjected into mammalian cells" Nucleic Acids Research, vol. 21, No. 16, pp. 3857-3865 (Jun. 1993).
Gardiner et al. "Extracellular vesicle sizing and enumeration by nanoparticle tracking analysis" Journal of Extracellular Vesicles 2, (Feb. 2013).
Geiss et al. "Direct multiplexed measurement of gene expression with color-coded probe pairs" Nature Biotechnology, vol. 26, No. 3, (Mar. 2008) pp. 317-325.
Grönwall et al. "Protective roles of natural IgM antibodies" Frontiers in Immunology, vol. 3, Article 66 (Apr. 2012).
Harty et al. "A PPxY motif within the VP40 protein of Ebola virus interacts physically and functionally with a ubiquitin ligase: implications for filovirus budding" Proc. Natl. Acad. Sci. U. S. A. 97, 13871-6 (Oct. 2000).
Hogue et al. "Gag induces the coalescence of clustered lipid rafts and tetraspanin-enriched microdomains at HIV-1 assembly sites on the plasma membrane" J. Virol., vol. 85, No. 19, pp. 9749-9766 (Oct. 2011).
Hoshino et al. "Tumour exosome integrins determine organotropic metastasis" Nature, 527(7578) pp. 329-335 (Nov. 2015).
Jouvenet et al. "Plasma membrane is the site of productive HIV-1 particle assembly" PLoS Biol., vol. 4, Issue 12, e435 (Dec. 2006) pp. 2296-2310.
Justice et al. "Membrane vesiculation function and exocytosis of wild-type and mutant matrix proteins of vesicular stomatitis virus" Journal of Virology, vol. 69, 3156-60 (May 1995).
Kalluri "The biology and function of fibroblasts in cancer" Nat. Rev. Cancer, vol. 16, 582-598 (Sep. 2016).
Kalra et al. "Focus on extracellular vesicles: Introducing the next small big thing" Int. J. Mol. Sci. 17, (Feb. 2016).
Lamb et al. "Orthomyxoviridae: The viruses and their replication" vol. 47 (1996).
Lee et al. "Acoustic purification of extracellular microvesicles" ACS Nano 9, 2321-7 (Dec. 2015).
Lötvall et al. "Minimal experimental requirements for definition of extracellular vesicles and their functions: A position statement from the International Society for Extracellular Vesicles" J. Extracell. Vesicles 3, 1-6 (Dec. 2014).
Melo et al. "Glypican-1 identifies cancer exosomes and detects early pancreatic cancer" Nature, vol. 523, 177-182 (Jul. 2015).
Nabhan et al. "Formation and release of arrestin domain-containing protein 1-mediated microvesicles (ARMMs) at plasma membrane by recruitment of TSG101 protein" Proc. Natl. Acad. Sci. U. S. A. 109, 4146-51 (Jan. 2012).
Nakai et al. "A novel affinity-based method for the isolation of highly purified extracellular vesicles" Sci. Rep. 6, 33935 (Sep. 2016).
Nawaz et al. "The emerging role of extracellular vesicles as biomarkers for urogenital cancers" Nat. Rev. Urol. 11, 688-701 (Nov. 2014).
Pastuzyn et al. "The Neuronal Gene Arc Encodes a Repurposed Retrotransposon Gag Protein that Mediates Intercellular RNA Transfer" Cell 172, 275-288.e18 (Jan. 2018).
Petersen et al. "A review of exosome separation techniques and characterization of B16-F10 mouse melanoma exosomes with AF4-UV-MALS-DLS-TEM" Anal. Bioanal. Chem. 406, 7855-66 (Dec. 2014).
Saad et al. "Structural basis for targeting HIV-1 Gag proteins to the plasma membrane for virus assembly" Proc. Natl. Acad. Sci. U. S. A., vol. 103, No. 30 pp. 11364-9 (Jul. 2006).
Sadovska et al. "Extracellular Vesicles as Biomarkers and Therapeutic Targets in Breast Cancer" Anticancer Res. 35, 6379-90 (Oct. 2015).
Tang et al. "Exosomes: Emerging biomarkers and targets for ovarian cancer" Cancer Lett. 367, 26-33 (Jul. 2015).
Thëry et al. "Isolation and characterization of exosomes from cell culture supernatants and Biological Fluids" Current Protocols in Cell Biology, Supplement 30, pp. 3.22.1-3.22.29 (Apr. 2006).
Tkach et al. "Communication by Extracellular Vesicles: Where We Are and Where We Need to Go" Cell 164, 1226-1232 (Mar. 2016).
Valkonen et al. "Biological reference materials for extracellular vesicle studies" Eur. J. Pharm. Sci. 98, 4-16 (2017) Accepted Sep. 6, 2016.
Van Der Pol et al. "Refractive index determination of nanoparticles in suspension using nanoparticle tracking analysis" Nano Lett. 14, 6195-6201 (Sep. 2014).
Van Der Vlist et al. "Fluorescent labeling of nano-sized vesicles released by cells and subsequent quantitative and qualitative analysis by high-resolution flow cytometry" Nat. Protoc. 7, 1311-26 (Jun. 2012).
Van Deun et al. "EV-TRACK: transparent reporting and centralizing knowledge in extracellular vesicle research" Nat. Methods 14, 228-232 (Mar. 2017).
Van Deun et al. "The Impact of Disparate Isolation Methods for Extracellular Vesicles on Downstream RNA Profiling" Journal of Extracellular Vesicles (Aug. 2014).
Vergauwen et al. "Confounding factors of ultrafiltration and protein analysis in extracellular vesicle research" Sci. Rep. 7, 2704 (Apr. 2017).
Witwer et al. "Standardization of sample collection, isolation and analysis methods in extracellular vesicle research" J. Extracell. Vesicles 2 (May 2013).

(56) References Cited

OTHER PUBLICATIONS

Yamamoto et al. "Use of serial analysis of gene expression (SAGE) technology" J. Immunol. Methods 250 (Apr. 2001):45-66.
Zhang et al. "Microenvironment-induced PTEN loss by exosomal microRNA primes brain metastasis outgrowth" Nature (Nov. 2015) doi:10.1038/nature 15376.
European Search Report Received for EP Application No. 18205202, dated on Feb. 20, 2019, 5 pages.
International Search Report for International Application No. PCT/EP2018/080299, mailed on Apr. 3, 2019, 5 pages.
International Written Opinion for International Application No. PCT/EP2018/080299, mailed Apr. 3, 2019, 5 pages.
Lobb et al., "Optimized exosome isolation protocol for cell culture supernatant and human plasma", Journal of extracellular vesicles, (Jan. 1, 2015), pp. 27031-11.
Urbanelli et al., "Send Orders for Reprints to reprints@benthamscience. ae Exosome-based strategies for Diagnosis and Therapy", Recent Patents on CNS Drug Discovery, (Jan. 1, 2015), pp. 10-27.

\* cited by examiner rEV

MOCK EV rEV

MOCK EV

```
SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
gacgacggca actacaagac                                                 20

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
tccttgaagt cgatgccctt                                                 20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
taaacggcca caagttcagc                                                 20

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
gaacttcagg gtcagcttgc                                                 20
```

USAGES OF RECOMBINANT EXTRACELLULAR VESICLES

CROSS-REFERENCE TO RELATED APPLICATIONS

This application is a national phase entry under 35 U.S.C. § 371 of International Patent Application PCT/EP2018/080299, filed Nov. 6, 2018, designating the United States of America and published as International Patent Publication WO 2019/091964 A1 on May 16, 2019, which claims the benefit under Article 8 of the Patent Cooperation Treaty to European Patent Application Serial No. 17200743.7, filed Nov. 9, 2017.

TECHNICAL FIELD

This disclosure relates to the field of research and clinical usage of extracellular vesicles. More in particular, this disclosure relates to usages of recombinant extracellular vesicles comprising a) a self-assembling protein that directs its own release through vesicles as a luminal membrane-bound protein and b) a heterologous marker. Indeed, this disclosure provides recombinant extracellular vesicles that can be used as a biological reference material in methods to quantify extracellular vesicles in a sample, and/or can be used to calibrate a device for sample extracellular vesicles analysis, and/or can be used to evaluate the isolation process of extracellular vesicles. This disclosure thus relates to improving the accuracy of an extracellular vesicle-based diagnosis.

BACKGROUND

Liquid biopsies increasingly gain attention as a golden standard for future clinical use because of the lower risk for the patient, the possibility of treatment monitoring, the lesser cost and the heterogeneous view of the disease compared to tissue biopsies.[1,2] Since it is generally accepted that extracellular vesicles (EV) are present in body fluids and that they represent a fingerprint of the originating cell they are focused upon as a candidate to provide information for medical decision making.[2,3]

EV are nanometer-sized vesicles secreted by all cell types and found circulating in body fluids like plasma, serum, urine, cerebrospinal fluid, etc. They consist of a double lipid membrane surrounding its cargo of proteins, nucleic acids and metabolites making them useful conveyors of information as the lipid membrane provides protection against degradative proteins, such as proteases and RNAses, present in biofluids.[4] EV are found to be implicated in cancer progression. They can be secreted by cancer cells and either activate or recruit cancer or stromal cells locally or educate a premetastatic niche at a distant location, and hereby facilitating metastasis formation.[5,6] Recently, EV isolated from different biofluids have been found to contain specific mRNA, miRNA and protein content related to disease state for breast, urogenital, pancreatic and ovarian cancers.[7-10] However, little advances are made towards clinical application. This is mainly due to the fact that EV research is difficult to reproduce owing to the plethora of isolation methods used and a lack of standardization and normalization.[11-13] The latter problems can be solved by using a standard reference material that has the same characteristics as sample EV, but can be easily distinguished from them.

Up to date there are few materials used as a reference material for EV research. Nanometer sized polystyrene or silica beads are often used as a calibrator for flow cytometry (FC) or nanoparticle tracking analysis (NTA). This usually leads to inaccurate measurements of EV as the refractive index (RI) of these beads is higher than the RI of EV (1.61, 1.46 vs 1.40).[14,15] Another alternative could be EV-inspired liposomes engineered to contain proteins and nucleic acids. However, natural EV are heterogeneous in size, and standards lacking this heterogeneity may consequently impact the standard reference settings of EV quantification methods. To overcome these problems, a biological reference material seems mandatory. A recent survey performed by researchers of the METVES program (Metrological characterization of micro vesicles from body fluid) indeed stated that an ideal EV reference material should be from biological origin and have the same physical and biochemical characteristics as sample EV and should preferably be distinguishable from them.[16] US20130078658 discloses a recombinant EV comprising a fusion of a membrane protein and a light-emitting protein that can be used to quantify sample EV. However, the latter recombinant EV are difficult to be produced in high quantities and cannot be detected in a very sensitive manner.

BRIEF DESCRIPTION OF THE DRAWINGS

(FIG. 1a) Schematic overview of the production of rEV at the cellular level: 1) The GAG-EGFP fusion protein inserts in regions of the plasma membrane enriched for tetraspanins CD9, CD63 and CD81 via its N-terminal MA domain containing a myristyl group; 2) The GAG-EGFP fusion protein oligomerizes and recruits ESCRT-1 proteins (TSG101) via the PTAP motive on its P6 domain; 3) Recruitment of ESCRT-2/3 proteins initiates the outward budding of the GAG-EGFP containing plasma membrane; and 4) ESCRT-3 mediated scission of the membranes finally causes release of rEV into the conditioned medium. (FIG. 1b) Schematic overview of the workflow to isolate rEV from conditioned medium of GAG-EGFP-transfected HEK293T cells. (FIG. 1c) Phase contrast microscopy images of HEK293T cells transfected with MOCK (up) and GAG-EGFP (under) DNA. (FIG. 1d) Cell viability of GAG-EGFP and MOCK-transfected HEK293T cells calculated using trypan blue. (FIG. 1e) Fluorescent microscopy image of GAG-EGFP-transfected HEK293T cells with the calculated transfection efficiency. Scale bar is 50 µm. (FIG. 1f) Transfection efficiency measured by FC of HEK293T cells transfected with GAG-EGFP gated for EGFP. (FIG. 1g) Western blot for EGFP and loading control tubulin of GAG-EGFP-transfected HEK293T cells in 6 biological replicates. 20 µg of protein was loaded. (FIG. 1h) Transfection stability assessed by the relative EGFP signal of the Western Blot in FIG. 1g.

(FIG. 2a) Comparison of particles per cell between GAG-EGFP-transfected and MOCK-transfected HEK293T cells quantified by nanoparticle tracking analysis (NTA) (n=24). (FIG. 2b) Comparison of the size modi of rEV versus EV from MOCK-transfected HEK293T cells measured by NTA (n=27). (FIG. 2c) Comparison of the zeta potential from both rEV and MOCK EV (n=6). (FIG. 2d) Western blot on all ODG fractions top to bottom from the conditioned medium of GAG-EGFP- and MOCK-transfected HEK293T cells for EGFP and EV enriched proteins TSG101, CD81 and Alix. Equal volumes were loaded. (FIG. 2e) Wide field and close-up electron microscopy (EM) images of both rEV (left) and MOCK EV (right). (FIG. 2f)

Size distribution of rEV (left) and MOCK EV (right) as measured from the EM images in FIG. 2e. (FIG. 2g) Refractive index distributions of rEV and MOCK EV calculated by nanoparticle tracking analysis and Mie theory.

(FIG. 3a) Western blot of rEV and EV from MOCK-transfected HEK293T cells and EV from MCF7-Rab27B cells for EV enriched proteins Alix, TSG101, CD81, Flotillin-1, Syntenin-1, CD9 and CD63. Equal amount of protein was loaded (5.7 µg). (FIG. 3b) Western blot for EGFP and CD81 of rEV immune precipitated (IP) with anti-CD81-coated magnetic beads (left) and empty magnetic beads (right) together with the flow through (FT). (FIG. 3c) Wide field and close-up immune electron microscopy (EM) images of rEV and MOCK EV against CD63. (FIG. 3d) Volcano plot of the fold changes of all detected proteins from MOCK EV (left) and rEV (right) with a FDR of 0.01 with the EV-associated proteins indicated as red dots. (FIG. 3e) Venn diagram of proteins from the ESCRT pathway, proteins enriched in rEV and MOCK EV and equally expressed proteins in both types of EV.

(FIG. 4a) Log 2 expression values of all detected phospholipids in rEV and MOCK EV. (FIG. 4b) µg cholesterol per particle of rEV and MOCK EV from four biological replicates.

(FIG. 5a) Size distribution graphs of rEV measured with nanoparticle tracking analysis (NTA) under both scatter and fluorescence mode (left) and the percentage of fluorescent particles of different rEV batches (n=20) (right). (FIG. 5b) Detection of rEV with high resolution FC. (FIG. 5c) Western blot for EGFP on the maximum detectable concentration range (up) and linear detectable concentration range (under) of rEV dilutions in PBS. (FIG. 5d) Linear detection of three biological replicates of rEV diluted in PBS with a fluorescent plate reader and the batch to batch variability. (FIG. 5e) Linear detection of three biological replicates of rEV diluted in PBS with an ELISA for p24, a subunit of the Gag polyprotein, and the batch to batch variability. (FIG. 5f) Semi logarithmic detection of EGFP mRNA with qPCR from rEV particles diluted in PBS. In FIGS. 5d and 5e, each biological replicate was measured in triplicate.

(FIG. 6a) Fluorescent particles/mL measured via fluorescent nanoparticle tracking analysis (fNTA) of rEV from different batches direct after isolation (fresh) and after 2 consecutive freeze thaw cycles (FT) at −80° C. (FIG. 6b) Fluorescent particles/mL measured via fNTA of fresh rEV or after 1 in 10 dilution and storage at 4° C. (FIG. 6c) Relative rEV concentration measured by fNTA immediately upon rEV isolation (fresh) or after storage at 4° C. up to three weeks without dilution. (FIG. 6d) Size distribution profile of rEV before (left) and after (right) lyophilization measured with fNTA. (FIG. 6e) Fluorescent particles/mL as measured with fNTA of rEV at different time points in conditions with or without light exposure. (FIG. 6f) Recovery of rEV spiked in plasma by size exclusion chromatography on fresh plasma or after freezing spiked plasma one week at −80° C.

(FIG. 7a) Western blot for TSG101 and EGFP on SEC fractions of PBS spiked with EV from MCF7-RAB27B or rEV and plasma spiked with rEV. (FIG. 7b) Calculation of recovery rate using fluorescent NTA (fNTA) and ELISA for p24 after isolation of rEV from plasma using SEC. (FIG. 7c) Calculation of the loss of rEV using fNTA after consecutive isolation steps in PK-treated plasma (SEC-ultrafiltration (UF), ODG and SEC). (FIG. 7d) Calculation of recovery rate using fNTA and ELISA for p24 after ODG and consecutive high speed pelleting in DMEM supplemented with 10% serum. (FIG. 7e) Loss during pelleting after density gradient centrifugation of spiked DMEM supplemented with 10% serum (sample 2 of FIG. 7d). (FIG. 7f) Calculation of recovery rate using fNTA and ELISA for p24 after differential ultracentrifugation in plasma. (FIG. 7g) Calculation of recovery rate using an ELISA for p24 after exoquick precipitation in plasma. All recovery calculations were performed in triplicate.

(FIG. 8a) Fluorescent particles in ODG fractions of PK treated and control plasma spiked with rEV as measured with fluorescent nanoparticle tracking analysis (fNTA). (FIG. 8b) Western blot for EGFP and human IgG on ODG fractions of PK treated and control plasma spiked with rEV. (FIG. 8c) EM image of pelleted ODG fractions 12-13 of rEV spiked plasma. (FIG. 8d) Fluorescent particles measured via fNTA in ODG fractions of plasma and DMEM supplemented with 10% FBS both spiked with rEV. (FIG. 8e) Fluorescent particles measured via fNTA in ODG fractions of top down (TD) and bottom up (BU) ODG gradients of urine spiked with rEV. (FIG. 8f) Percentage fluorescent particles per ODG fraction of rEV particles spiked in PBS in the presence or absence of human IgM or IgG. (FIG. 8g) Total amount of particles in PK treated and control plasma after SEC followed by ODG. (FIG. 8h) Western blot analysis for EV enriched proteins flotillin-1 and syntenin-1 on 6 mL of cancer plasma treated with PK after SEC followed by ODG.

(FIG. 9a) PEG modified rEV are compatible with multiple biofluids and can be separated from EV for downstream approaches. (FIG. 9b) Density distribution of rEV-PEG and rEV spiked in plasma, measured by fNTA. (FIG. 9c) Western blot analysis for EGFP and syntenin-1 of immune precipitated rEV and rEV-PEG in PBS with anti-PEG or aspecific goat IgG-coated magnetic beads. (FIG. 9d) Log of the number of EV measured by NTA before and after normalization by rEV quantification with fNTA to reduce inter-user variability. (FIG. 9e) Log of the EV/mL plasma from healthy volunteers and breast cancer patients (n=6 and n=18) after isolation by SEC-ODG-SEC and normalization by rEV quantification with fNTA. ** $P<0.01$.

DETAILED DESCRIPTION

Figure 1A:
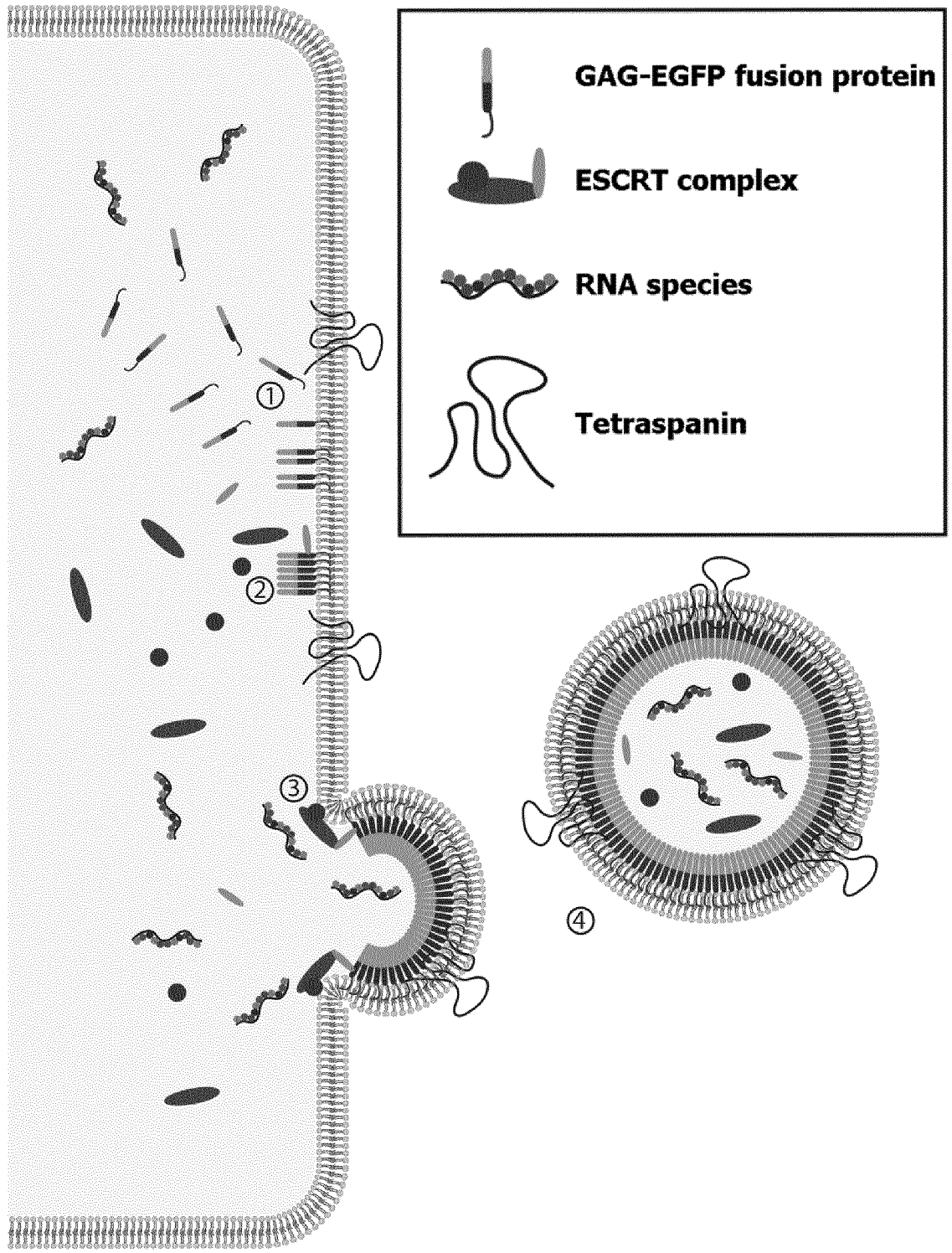
FIGS. 1a-1h: Production of recombinant extracellular vesicles (rEV).

In this disclosure, the use of a particular kind of recombinant extracellular vesicle (rEV) was used as a biological reference material for EV research. These rEV are induced by self-assembling proteins that direct their own release through vesicles as a luminal membrane-bound protein and further comprise a heterologous marker that can be fused to the self-assembling proteins. A non-limiting example of such a self-assembling protein is the retroviral group-specific antigen (Gag) fused to a heterologous marker such as the light-emitting enhanced green fluorescent protein (EGFP). The physical and biochemical characteristics of density gradient purified particles from the supernatant of Gag-EGFP-transfected HEK293T cells and endogenous sample EV from different cell lines and biofluids at the level of NTA, (immune) electron microscopy, proteomics, lipidomics and zeta potential were analyzed and compared. The high abundance of fluorescent fusion proteins per particle can be exploited to deduce the amount of particles, as measured with fluorescent NTA, by measuring fluorescent signals with a fluorescent plate reader, high resolution FC or by measuring the concentration of, for example, the Gag polyprotein or, most preferably, by measuring the concentration of, for example, EGFP mRNA. It was shown that the latter non-fluorescence-based measurements are far more sensitive than the fluorescence measurements. It was further shown that rEV can be used as a reference material to spike in different biofluids prior to isolation and afterwards be tracked, giving the possibility to calculate the recovery rate of different EV isolation methods. The methods of this disclosure allow the end user to choose whether he wishes to isolate the reference material together with the sample EV or separated from the sample EV. In addition, it is disclosed herein that rEV can be used to calibrate a device for analyzing sample EV and that rEV can be used to evaluate EV isolation methods. Taken together, the methods of this disclosure clearly enable the comparison of results between different research groups, and support the use of EV measurements for the diagnosis, prognosis and therapeutic decision making of diseases such as, but not limited to, cancer, diabetes and cardiovascular disease.

This disclosure thus provides for a method to determine the recovery rate of sample EV, the method comprising:
- mixing a biofluid sample comprising sample EV with a known amount of rEV wherein rEV comprise: a) a self-assembling protein that directs its own release through vesicles as a luminal membrane-bound protein, and b) a heterologous marker, to obtain a mixture,
- isolating the EV from the mixture,
- detecting the amount of the rEV among the isolated EV, and
- determining the recovery rate of the sample EV based on the ratio of the amount of rEV after the isolation step to the known amount of rEV mixed with the biofluid sample before the isolation step.

As used herein, the term "sample extracellular vesicle (sample EV)" refers to endogenous EV present in a sample, such as a biofluid, taken from a patient. The term "endogenous EV" refers to membrane-structured vesicles that are secreted by a wide range of cell-types including red blood cells, tumor cells and immune cells.[4] Endogenous EV are known to be released in both normal and pathological conditions and are known to contain proteins, lipids, nucleic acids such as miRNAs, and metabolites. It has been disclosed that the amounts of various types of, for example, miRNAs present in endogenous EV correlate with particular diseases.[17] Hence, accurate quantification of EV in EV-based diagnostics is crucial.

As used herein, the term "recombinant extracellular vesicles (rEV)" refers to EV obtainable by transfecting an appropriate host cell with DNA encoding for "a self-assembling protein that directs its own release through vesicles as a luminal membrane-bound protein" and with DNA encoding for "a heterologous marker." The latter "heterologous marker" can thus be provided by direct transfer into producer cells using cell-transfection procedures known to a person skilled in the art. For heterologous markers consisting of RNA, this molecule can be supplied either in its native form (i.e., unprotected) or in a protected form. Protected RNA relates to modifications in the RNA molecule that enhance the stability of the molecule by reducing RNase activity (see Fisher T L, Terhorst T, et al. (1993) Nucleic Acids Res, 21:3857-3865). Examples of modifications are phosphorothioate bonds, 2'-O-methyl bases and 2'fluoro bases. Alternatively, and as indicated above, the heterologous RNA molecule can be transcribed from an expression cassette, either transfected in cells as a double stranded DNA fragment, as part of a plasmid, or after integration of the expression cassette in the genome. In its simplest form, an expression cassette consists of a promoter, a sequence that is transcribed and a sequence that terminates transcription. Additional elements can be added to improve the transcription process: 1) the transcribed DNA fragment can be fused directly to the DNA that encodes the self-assembling protein; 2) the transcribed DNA encodes a heterologous marker protein (a luminescent, fluorescent or any other detectable protein) that is translated as a fusion protein to the self-assembling protein.

The heterologous RNA marker molecule can be recruited to the vesicles by aspecific binding to the self-assembling protein (see M. Comas-Garcia et al., eLife 2017 (6): 1-27) or by specific recruitment to the self-assembling protein via the retroviral packaging signal psi (see M. Comas-Garcia et al., eLife 2017 (6): 1-27). Alternatively, the heterologous marker is recruited by a nucleotide-binding polypeptide that recognizes a specific nucleotide target sequence. To this end, the nucleotide-binding polypeptide is fused directly to the self-assembling protein. Non-limiting examples of RNA-binding polypeptides are Lambda N, RNA-binding domain of MS2, NS3 and Cas9. The nucleotide target sequence can be used directly as heterologous marker, or can be fused to the heterologous marker sequence. Non-limiting examples of nucleotide target sequences are NutL, MS2, NS3 aptamers and gRNAs.

The terms "heterologous marker" mean a marker derived from a different organism than the organism from which the sample EV are under examination, or a synthetic marker, not originating from any existing organism. The term "marker" as used herein refers to a measurable, heterologous protein or nucleic acid whose detection indicates the presence of a rEV of this disclosure. A preferred heterologous protein marker of the disclosure is a light-emitting protein as is also defined further.

Hence, this disclosure further relates to a method as described above wherein the heterologous marker is a heterologous nucleic acid molecule or a heterologous protein.

Furthermore, this disclosure relates to a method as described above wherein the heterologous protein is fused to the self-assembling protein.

Moreover, this disclosure relates to a method as described above wherein the heterologous nucleic acid is fused to the retroviral packaging signal psi.

The disclosure further relates to a method as described wherein the detecting step is undertaken by determining the amount of any heterologous nucleic acid by—as non-limiting examples—real-time PCR, RT-qPCR, digital PCR or RNA sequencing. A skilled person will understand that also other techniques to quantify the amount of heterologous nucleic acids such as nanostring (see Geiss et al., Nature Biotechnology 26 (2008):317-325), branched DNA amplification (see Collins et al., Nucleic Acids Res. 25 (1997): 2979-2984) or serial analysis of gene expression (SAGE; see M. Yamamoto et al., J. Immunol. Methods 250 (2001):45-66) can be used.

As a preferred embodiment, the disclosure further relates to a method as described above wherein the heterologous protein is a light-emitting protein or wherein the heterologous nucleic acid is light-emitting protein mRNA.

The term "a self-assembling protein that directs its own release through vesicles as a luminal membrane-bound protein" means a protein that comprises: a) a membrane insertion domain that is a protein domain that directly inserts in the double lipid layer or that recruits a lipid chain for insertion (a non-limiting example of such a domain is the MA domain of the well-known retroviral group-specific antigen (Gag)), b) a self-assembling domain that is a protein domain that is responsible for oligomerization. The latter is required for a tight packing of proteins in a small domain of the lipid membrane, so that one vesicle contains a high amount of copies of that same (a non-limiting example of such a domain is the CA domain in the Gag polyprotein), and c) a late budding domain that is a protein domain that comprises a PTAP, PPXY or FPIV amino acid sequence for recruitment of ESCRT proteins required for vesicle morphogenesis. A non-limiting example of such a domain is the P6 domain of the Gag polyprotein.[18, 19] Non-limiting examples of such a "self-assembling protein that directs its own release through vesicles as a luminal membrane-bound protein" are—besides Gag—Gag variations as described by Coffin and Hughes,[20] the influenza M1 proteins as described by Lamb and Krung,[21] the Arrdc1 protein as described by Kuo et al.,[22] the Ebola virus VP40 protein as described by Harry et al.,[23] the Arc protein as described by Pastuzyn et al.[24] and the M proteins of vesicular stomatitis virus as described by Justice et al.[25]

Hence, the disclosure relates to methods as described above and as described further wherein the self-assembling protein that directs its own release through vesicles as a luminal membrane-bound protein is chosen from the group consisting of: the retroviral group-specific antigen, retroviral group-specific antigen variations, the influenza M1 protein, the Arrdc1 protein, the Arc protein, the Ebola virus VP40 protein and the M proteins of vesicular stomatitis virus.

A non-limiting example of a "rEV" of the present disclosure is the one obtainable by transfecting HEK293T cells with DNA encoding for the retroviral Gag polyprotein C-terminally linked with enhanced green fluorescent protein (EGFP), followed or not by the retroviral packaging signal psi, overexpressing the Gag-EGFP fusion protein in the embryonic kidney cells for a certain period of time and isolating the rEV from the conditioned medium via density gradient ultracentrifugation.

As used herein, the term "light-emitting protein" refers to any protein that emits light by a change in physical conditions or by a chemical process. Non-limiting examples of such proteins are fluorescent proteins such as green fluorescent protein, enhanced green fluorescent protein, yellow fluorescent protein and red fluorescent protein, luminescent proteins, photoproteins or luciferase. The light-emitting protein is positioned inside the rEV as is—for example— explained in detail in US 20130078658. Hence, the present disclosure provides a method as described above wherein the light-emitting protein is a fluorescent protein or a luminescent protein. The present disclosure specifically provides a method as described above wherein the fluorescent protein is green fluorescent protein.

As used herein, the term "biofluid sample" (which contains sample EV) can be any suitable biofluid taken from the body or in vitro cultures. Non-limiting examples of such biofluids are plasma, serum, blood, urine, mucus, saliva, stool, brocheoalveolar fluid (BALF), sweat, vitreous humor, tear drops or culture medium derived from in vitro cell or tissue cultures. However, the present disclosure specifically provides a method that is described further as a second embodiment wherein the biofluid sample is a plasma or serum sample as these biofluids may contain a endogenous Immunoglobulins such as IgM and/or IgG.

After mixing a biofluid sample comprising sample EV with a known amount of rEV, the method comprises isolating both types of EV using any type of isolation method such as any type of density-based isolation method, size-based isolation, protein-based isolation, precipitation-based isolation, electrotatic-based isolation, acoustic-based isolation, microfluidics-based isolation or lipid-based isolation.[13, 26-30]

Detecting the amount of the rEV among the isolated EV can be—as already mentioned above—undertaken by qPCR or any other method as described above for light-emitting protein mRNA or any other heterologous nucleic acid. In other words, quantification of the rEV can be performed using any appropriate method known in the art. Non-limiting examples of such methods are fluorescence intensity measurement methods using a fluorescence microplate reader, FC, fluorescent NTA (fNTA), qPCR for light-emitting protein mRNA or an enzyme-linked immune sorbent assay against a subunit of the "self-assembling protein that directs its own release through vesicles as a luminal membrane-bound protein" or the light emitting protein.

The method of the disclosure further includes determining the recovery rate of the sample EV from a ratio of the amount of rEV after isolation to the known amount of rEV added to the sample, which contains the sample EV, before isolation. The ratio of the rEV after isolation to the known amount of the rEV added to the sample containing sample EV can be calculated and used in calculating the recovery rate of the sample EV. The latter recovery rate can be used in quantifying and normalization of—for example—miR-NAs or proteins in a sample obtained from a patient and can thus be used in diagnosis based on sample EV.

In another embodiment, the disclosure more specifically relates to a method as described above, wherein the isolation step comprises a separation step and/or is combined with a separation step in order to obtain a first fraction comprising the rEV and a second fraction comprising the sample EV, wherein detecting of the amount of the rEV occurs in the first fraction. The latter separation step is preferably a density-based separation step. However, since this separation is based on the adherence of immunoglobulins to the rEV it can also be achieved by immunocapturing the rEV with for instance (magnetic) beads expressing anti-IgM/anti-IgG antibodies on its surface. The above-mentioned separation can also be achieved by using a high resolution FC that can sort vesicles based on a fluorescent signal as explained by Van de vlist et al.[31] The step of "detecting the amount of the rEV in the first fraction" can be undertaken by, for example, a fNTA analysis, qPCR for light emitting protein mRNA or, an enzyme-linked immune sorbent assay against a subunit of the self-assembling protein.

After mixing a biofluid sample comprising sample EV with a known amount of rEV, the method described in this embodiment comprises separating both types of EV using any type of separation method resulting in a first fraction comprising the rEV and a second fraction comprising the sample EV. This surprising and unique feature of the method of the present disclosure allows the end user to isolate the rEV separated from the sample EV. This allows further downstream analysis of sample EV without disturbance by rEV. This unique feature is due to the fact that immunoglobulin proteins, such as IgM and/or IgG, endogenously present in the biofluid sample or exogenously added to the rEV bind to the surface of the rEV as a consequence of the outer membrane orientation of specific lipids (phosphatidylserine or lysophosphatidylcholine). These lipids are then recognized by antibodies, such as IgM and/or IgG, as a Damage/Pathogen Associated Molecular Pattern (DAMP/PAMP).[32, 33]

Non-limiting examples of the separation methods, preferably density-based isolation methods, are density gradient ultracentrifugation and density cushion centrifugation.

Furthermore, this disclosure specifically provides a method as described above wherein the density-based separation is iodixanol density gradient ultracentrifugation.

Furthermore, the disclosure provides a method as described above wherein the density gradient centrifugation is preceded or not by an additional biophysical isolation step.

Non-limiting examples of the latter biophysical isolation steps are ultrafiltration, size exclusion chromatography and differential ultracentrifugation.

More specifically, the disclosure provides a method as described above wherein the additional isolation step is a size exclusion chromatography.

After separating both types EV, the method of the latter embodiment of the disclosure includes the step of detecting or quantifying the amount of the rEV in the first fraction. Quantification of the rEV can be performed using any appropriate method known in the art. Non-limiting examples of such methods are fluorescence intensity measurement methods using a fluorescence microplate reader, FC, fNTA, qPCR for light-emitting protein mRNA or an enzyme-linked immune sorbent assay against a subunit of the "self-assembling protein that directs its own release through vesicles as a luminal membrane-bound protein" or the light emitting protein. Hence, the present disclosure further provides a method as described above wherein detecting the amount of the rEV in the first fraction is undertaken specifically by high resolution FC or fNTA analysis, or, qPCR for light emitting protein mRNA and an enzyme-linked immune sorbent assay against a subunit of the self-assembling protein that directs its own release through vesicles as a luminal membrane-bound protein.

Moreover, and as stated above, the method of the disclosure actually allows the end user to choose whether he wishes to isolate the rEV together with the sample EV or separated from the sample EV. Indeed, the disclosure also provides a method as described above wherein the mixture is treated with a protease before the density-based isolation so that the rEV and the sample EV are present in the same density fraction after the density-based isolation. Any protease such as papain, trypsin or subtilisin can be used. However, the present disclosure specifically provides a method as described above wherein the protease is proteinase K. In order to have the rEV and the sample EV present in the same density fraction, the rEV can be incubated with lipid conjugated PEG prior to mixing the rEV with the biofluid sample. In this method the lipid conjugated PEG—for example DMPE-PEG—inserts in the membrane of the rEV orienting the low molecular weight PEG chains to the exterior of the rEV. This exterior orientation of the low molecular weight PEG chains then sterically inhibits the adherence of immunoglobulins to the surface of the rEV. After isolation of the rEV incubated with lipid conjugated PEG and the sample EV in the same density fraction, the rEV incubated with lipid conjugated PEG can be separated from the sample EV by immune precipitation using anti-PEG antibodies. Hence, the present disclosure relates to a method as described above wherein the rEV incubated with PEG and the sample EV isolated in the same fraction after the isolation are incubated with anti-PEG-coated magnetic beads so that the rEV incubated with PEG are separated from the sample EV. A skilled person will understand that also other techniques to capture the recombinant extracellular vesicles incubated with PEG like immunecapture in microfluidic devices, immune affinity chromatograpy or immunecapture on coated plastic wells can be used.

On the other hand, the present disclosure also provides a method as described above wherein the rEV are incubated with immunoglobulin proteins such as IgG and/or IgM before mixing the biofluid with a known amount of the rEV so that the rEV and the sample EV are present in a different fraction after the separation step. The latter method is suited especially for biofluid samples that contain trace amounts or no endogenous immunoglobulin proteins.

Nanometer sized polystyrene or silica beads are often used as a calibrator for FC or NTA. This usually leads to inaccurate measurements of EV as the refractive index (RI) of these beads is higher than the RI of EV (1.61, 1.46 vs 1.40). This higher RI results in increased scattering and consequently wrong device settings for EV measurements that have a lower RI and thus scatter less light.[14, 15] A biological reference material with the same RI as sample EV is required to calibrate these devices.[16] By means of NTA and MIE theory calculations,[14] the RI of the recombinant extracellular vesicles could be accurately determined and found to be equal to the RI of the sample extracellular vesicles.

Therefore, the present disclosure also relates to a method to calibrate a device for sample EV analysis, the method comprising:

mixing a fluid with rEV from which the properties are known and wherein the rEV comprise: a) a self-assembling protein that directs its own release through vesicles as a luminal membrane-bound protein, and optionally b) a heterologous marker, to obtain a mixture, introducing the mixture into the device, analyzing a property of the rEV in the mixture, optionally analyzing the property again with one or more new combinations of device settings, deriving from the analysis of the rEV a combination of device settings that gives the exact property of the rEV used to obtain the mixture, and using the combination of device settings to calibrate the device against future subsequent analysis of samples containing EV of unknown properties, to determine the exact properties thereof.

The term "to calibrate" as used herein means to define the appropriate settings of a device to analyze sample EV.

The term "fluid" as used herein means, for example, a buffer in which the sample EV are isolated.

The term "optionally" refers to the fact that a heterologous marker is not, under all circumstances, used in the claimed calibration method because there are a number of analyses (except in the case of, for example, an analysis based on fluorescent threshold flow cytometry) that are based on the characteristics of sample EV that do not express a heterologous marker.

The term "a property" as used herein means the concentration and/or a specific characteristic, such as, the size, the morphology, the presence of EV markers, the zeta potential, etc., of EV.

Non-limiting examples of "analyzing a property" in relation to a device that has to be calibrated are: 1) choosing the optimal settings of an EM that reveal normal morphology of rEV, 2) defining the optimal settings of NTA or FC instruments that result in the approximate concentration or size of the rEV, 3) defining the optimal settings of a zetasizer, which gives the approximate zeta potential of rEV, etc.

The term "device settings" as used herein means, for example, the camera level for NTA, the detection threshold for NTA or FC, the right voltage for EM and or zeta potential measurements, the right pore size for TRPS, etc.

The present disclosure further relates to a method as described above wherein the device is a flow cytometer, a nanoparticle tracking analysis device, a tunable resistive pulse-sensing device, a plate reader, a microfluidics device, an ELISA reader, a zetasizer, an atomic force microscope, surface plasmon resonance analyzers or an electron microscope.

This disclosure also relates to a method to evaluate the isolation of EV, the method comprising:
- mixing a fluid with rEV wherein the rEV comprise: a) a self-assembling protein that directs its own release through vesicles as a luminal membrane-bound protein, and b) a heterologous marker, to obtain a mixture,
- isolating the rEV from the mixture, and
- detecting the presence of the rEV isolated from the mixture.

The terms "evaluate the isolation" as used refers to the fact that producers of new EV isolation methods can use the rEV described in the present disclosure to evaluate whether their new technique isolates EV. For example: developers of an EV detection chip can test their chip with rEV (which are easily detectable) before testing endogenous EV containing samples.

The term "detecting" refers to the above mentioned detection techniques of the heterologous marker (ELISA, fNTA, fluorescent FC, RT-qPCR, . . . ).

This disclosure will be described in further detail in the following examples.

These examples are illustrative and are not intended to limit the scope of the invention.

EXAMPLES

Materials and Methods

Antibodies

The following primary and secondary antibodies were used for immunostaining: mouse monoclonal anti-Alix (1:1000) (2171, Cell Signaling, Danvers MA, USA), Rabbit monoclonal anti-CD9 clone D3H4P (1:1000) (13403S, Cell Signaling), mouse monoclonal anti-CD63 clone MEM-259 (1:200) (ab8219, Abcam, Cambridge, UK), mouse monoclonal anti-CD81 (1:1000) (SC-166029, Santa Cruz Biotechnology, Dallas TX, USA), mouse monoclonal anti-Flotillin-1 (1:1000) (610820, BD Biosciences, Franklin Lakes NJ, USA), mouse monoclonal anti-green fluorescent protein (GFP) (1:1000) (MAB3580, Merck Millipore, Billerica MA, USA), rabbit monoclonal anti-IgG (1:1000) (ab181236, Abcam), Chicken polyclonal anti-IgM (1:1000) (ab26867, Abeam), anti-Syntenin-1 (1:1000) (ab133267, Abeam), mouse monoclonal anti-α-tubulin (1:4000) (T5168, Sigma, Saint Louis, MO, USA), sheep anti-mouse horseradish peroxidase-linked antibody (1:3000) (NA931V, GE Healthcare Life Sciences, Uppsala, Sweden), donkey anti-rabbit horseradish peroxidase-linked antibody (1:4000) (NA934V, GE Healthcare Life Sciences) and goat anti-chicken IgY horseradish peroxidase-linked antibody (1:5000) (A16054, Thermo Fisher scientific, Erembodegem, Belgium). Immunoelectron microscopy was performed with a primary mouse monoclonal anti-CD63 antibody (clone H5C6) (557305, Becton Dickinson) and a rabbit anti-mouse IgG (Zymed Laboratories, San Francisco, CA, USA). For CD81 immunoprecipitation mouse monoclonal anti-CD81 antibody was used (MA5-13548, Thermo Fischer scientific).

Cell Culture and Transfection

HEK293T cells were cultured in a humidified atmosphere at 10% CO2 using high glucose DMEM (Invitrogen, Carlsbad, CA) supplemented with 10% fetal bovine serum, 100 U/mL penicillin and 100 µg/mL streptomycin. Cells were passaged at 70-80% confluency in T175 flasks and were discarded after 10 passages. Cell cultures were regularly tested and found negative for *mycoplasma* contamination using the MycoAlert *Mycoplasma* Detection Kit (Lonza, Verviers, Belgium).

pMET7-GAG-EGFP and empty pMET7mcs (MOCK) plasmids were purified from DH10B *E. coli* using the PC2000 nucleobond kit (Macherey-Nagel, Düren, Germany) following manufacturer's procedures.[34] Cells were seeded in T175 flasks and were transfected at 70-80% confluency (day 1) using 25K linear polyethyleneimine (PEI) (Polysciences, Warrington PA, USA) in a PEI:DNA ratio of 5:1 with a final concentration of 1 µg DNA/mL culture medium in a total volume of 120 mL per multilayer cell culture flask.

rEV Isolation 48 hours following transfection (day 3) cells were washed three times using Opti-MEM reduced serum medium (31985070, Thermo Fischer Scientific) followed by 24 hours incubation with 15 mL Opti-MEM reduced serum medium supplemented with 100 U/mL penicillin and 100 µg/mL streptomycin at 37° C. and 10% CO2. Conditioned medium (CM) was harvested and centrifuged for 10 minutes at 200 g and 4° C. to remove detached cells, followed by a 0.45 µm cellulose acetate filtration (Corning, New York, USA) to remove larger particles. Next, CM was concentrated approximately 300 times using a Centricon Plus-70 centrifugal filter device with a 10K nominal molecular weight limit (Millipore, MA, USA). The resulting concentrated CM (CCM) was filtered through a 0.2 µm cellulose acetate filter (Whatman) and 1 mL was used for Optiprep density gradient ultracentrifugation. Following collection of the medium, cell cultures were trypsinized and cell viability was measured on a Countess Automatic Cell Counter (Invitrogen) using a 0.1% trypan blue exclusion test.

A discontinuous iodixanol gradient was made by layering 4 mL of 40%, 4 mL of 20%, 4 mL of 10% and 3.5 mL of 5% iodixanol solutions on top of each other in a 16.8 mL open top polyallomer tube (337986, Beckman Coulter).[26] 1 mL CCM sample was overlaid on top of the gradient, which was then centrifuged for 18 hours at 100,000 g and 4° C. (SW 32.1 Ti rotor, Beckman Coulter). All gradients were made using a biomek 4000 automated workstation (Beckman Coulter). Solutions of 5%, 10%, 20% and 40% iodixanol were made by mixing appropriate amounts of a homogenization buffer (0.25 M sucrose, 1 mM EDTA, 10 mM Tris-HCL, [pH 7.4]) and an iodixanol working solution. This working solution was prepared by combining a working solution buffer (0.25 M sucrose, 6 mM EDTA, 60 mM Tris-HCl, [pH 7.4]) and a stock solution of OptiPrep™ (60% (w/v) aqueous iodixanol solution) (Axis-Shield, Oslo, Norway). After centrifugation (day 4) gradient fractions of 1 mL were collected from top to bottom using a biomek 4000 automated workstation, fractions 8 and 9 were diluted to 16 mL in PBS and centrifuged for 3 hours at 100,000 g and 4° C. The resulting pellets were resuspended in 100 µL PBS and stored at −80° C. For proteomics and lipidomics, the last 100,000-g pelleting step was replaced by a size exclusion chromatography (SEC) and fractions 4-7 were collected.[35]

To estimate the density of each fraction, a standard curve was made of the absorbance values at 340 nm of 1:1 aqueous dilutions of 5%, 10%, 20% and 40% iodixanol solutions. This standard curve was used to determine the density of fractions collected from a control gradient overlaid with 1 mL of PBS.

Sample Collection

Collection of patient samples was according to ethical committee of Ghent university hospital approval and in accordance to relevant guidelines. Venous blood from healthy volunteers and breast cancer patients was collected using Venosafe-citrate tubes (VF-054SBCS07, Terumo Europe, Leuven, Belgium). Directly after collection, whole blood was centrifuged two times for 15 minutes at 2500 g at room temperature resulting in platelet free plasma (PFP). PFP was stored at −80° C. until further use or used instantly (fresh) when stated so. Urine from healthy volunteers was collected and centrifuged for 10 minutes at 1000 g and 4° C. followed by direct EV isolation.

EV isolation

Differential ultracentrifugation (diff UC) was performed according to Thery et al.[30] In short, plasma was diluted with equal volumes of PBS and centrifuged at 2000 g for 30 minutes at 4° C., the supernatant was then centrifuged once at 12,000 g for 45 minutes and 2 hours at 111,000 g at 4° C. in a SW32.1 Ti rotor (Beckman Coulter). The resulting pellet was then diluted to 5 mL PBS, 0.22 µm filtered and centrifuged again at 110,000 g for 70 minutes in a SW55 Ti rotor (Beckman Coulter). The final pellet was resuspended in 100 µL PBS and analyzed directly with NTA or stored at −80° C. for protein analysis.

Size exclusion chromatography (SEC) was performed in a 10 mL syringe with a nylon net with 20 µm pore size (NY2002500, Merck Millipore, Billerica MA, USA) at the bottom. The syringe was packed with 10 mL pre-washed sepharose CL-2B (GE Healthcare, Uppsala, Sweden) and a 2 mL sample was loaded on top, after which 1 mL fractions of eluate was collected under constant gravitational flow by continuously adding PBS containing 0.32% trisodiumcitrate dihydrate (ChemCruz, Dallas, Texas, USA). The collected fractions were analyzed directly with NTA or frozen at −80° C. for protein analysis.

To further purify EV, following SEC, eluted fractions 4-5-6 were concentrated to 1 mL with Amicon Ultra-2 mL centrifugal filters with a 10K cut-off value (UFC201024, Merck Millipore, Billerica MA, USA) and placed on top of a discontinuous iodixanol gradient and centrifuged as previously described in the rEV isolation section. If stated so, an additional proteinase K (PK) treatment was performed after concentration and before density gradient centrifugation. This was done at a PK concentration of 1 mg/mL for 60 minutes at 37° C. and was ended at 4° C.

ExoQuick-TC was used according to manufacturer's instructions (System Biosciences). Briefly, 250 µL defibrinated plasma was mixed with 63 µL ExoQuick-TC solution and incubated at 4° C. for 30 minutes. Afterwards the mixture was spun down at 1500 g for 30 minutes and the resulting pellet was resuspended in 200 µL RNase free water and stored at −80° C.

(Immune-)Electron Microscopy

Isolated EV were deposited on glow-discharged formvar carbon-coated grids and stained with neutral uranylacetate and embedded in methylcellulose/uranyl acetate. For Immune electronmicroscopy, the grids containing the vesicles were incubated with 1% BSA in PBS blocking solution. Antibodies and gold conjugates were diluted in 1% BSA in PBS. The grids were exposed to the primary anti-CD63 antibody for 20 minutes, followed by secondary antibody to rabbit anti-mouse IgG (Zymed, San Francisco, CA, USA) for 20 minutes and protein A-gold complex (CMC Utrecht, The Netherlands) for 20 minutes. The grids were examined in a Tecnai Spirit transmission electron microscope (FEI, Eindhoven, The Netherlands). Images were captured by Quemesa charge-coupled device camera (Olympus Soft Imaging Solutions, Munster, Germany).

Nano Particle Tracking Analysis

Nano particle tracking analysis (NTA) was performed using a NanoSight LM10-HS microscope (NanoSight, Amesbury, UK) equipped with a 488 nm laser and an automatic syringe pump system. For conventional NTA three 30 second videos were recorded of each sample with a camera level of 14, a detection threshold of 3 and a syringe pump infusion speed of 20. For fluorescent NTA measurements (fNTA) an additional 500 nm longpass filter was used, and the camera level was increased to 16. Temperatures were monitored throughout the measurements and the videos were analyzed with NTA software 3.2. For optimal measurements, samples were diluted with PBS until particle concentration was within optimal concentration range of the NTA Software ($3 \times 10^8$-$1 \times 10^9$). For recovery calculations the amount of fluorescent particles was measured before spiking.

High Resolution Flow Cytometry

High-resolution flow cytometry of EV was performed on a jet-in-air-based BD Influx flow cytometer (BD Biosciences, San Jose, CA) using an optimized configuration.[31] In brief, the BD Influx was triggered on the fluorescence signal derived from the fluorescently labeled rEV, and thresholding was applied on this channel. The threshold level was adjusted to allow an event rate ≤10/s when running clean PBS. Forward scatter was measured with a collection angle of 15-25 degrees (reduced wide-angle forward scatter [rw-FSC]). Three lasers were used: a 200 mW 488 nm laser (Sapphire; Coherent, Santa Clara, CA), a 150 mW 561 nm laser (Jive; Cobolt, Solna, Sweden), and a 120-mW 640-nm laser (Melles Griot, Carlsbad, CA). A large-bore nozzle (140 µm) was used, sheath pressure was permanently monitored and kept within 4.89 to 5.02 psi, and the sample pressure was set at 4.29 psi, to assure an identical diameter of the core in the jet stream. EV counts were determined by measuring each sample for 30 seconds. The event rate was below <10,000/s to avoid coincident particle detection and occurrence of swarm.

Zeta Potential Measurements

Zeta potential measurements were performed with a zetasizer nano ZS, which makes use of laser doppler electrophoresis, (Malvern Instruments Ltd, Malvern, UK) in disposable folded capillary cells at 22° C. in distilled water. MOCK EV and rEV particles were suspended in equal amounts of particles in distilled water and five measurements of 10-100 runs were performed using the "automode" option. Zeta potential values given are the means of the five respective measurements.

rEV Quantification Via Fluorescence Intensity Measurement

Fluorescence measurements were performed with a spectramax paradigm multi-mode microplate reader (molecular devices, Sunnyvale CA, USA) equipped with a 488 nm laser and a 500 nm filter. As a positive control, an ALEXA FLUOR®-488 antibody was used, and the relative fluorescence units (RFU) were calculated by subtracting the FU of a negative control (PBS) from the FU of the samples. All measurements were performed in triplicate.

rEV quantification via anti-P24 ELISA

GAG-EGFP protein concentrations were determined with the commercially available anti-P24 ELISA kit Innotest HIV antigen mAB (Innogenetics, Ghent, Belgium). The assay was performed following manufacturer's instructions. For recovery calculations an rEV standard curve, from the same batch as used for spiking, was included ranging from $10^7$ to $10^6$ fluorescent particles as previously measured with fNTA.

Protein Analysis

Protein concentrations of EV were measured, after lysis with 0.2% sodium dodecylsulphate (SDS), with the Qubit Protein assay kit (ThermoFisher, Waltham MA, USA) and Qubit fluorometer 3.0 following manufacturer's instructions. Protein concentrations of cell lysates, obtained in Laemmli lysis buffer (0.125 M Tris-HCl [pH 6.8], 10% glycerol, 2.3% SDS), were determined using the Bio-Rad DC Protein Assay (Bio-Rad, Hercules, USA). For protein analysis, samples were dissolved in reducing sample buffer (0.5 M Tris-HCl (pH 6.8), 40% glycerol, 9.2% SDS, 3% 2-mercaptoethanol, 0.005% bromophenol blue) and boiled at 95° C. for 5 minutes. For CD63 analysis samples were dissolved in non-reducing sample buffer lacking 2-mercaptoethanol. Proteins were separated by SD S-PAGE and transferred to nitrocellulose membranes (Bio-Rad, Hercules CA, USA). Membranes were blocked for 30 minutes in blocking buffer (5% nonfat milk in PBS with 0.5% TWEEN®-20) and incubated overnight at 4° C. with primary antibodies. Secondary antibodies were added for 60 minutes at room temperature after extensive washing with blocking buffer. After final washing, chemiluminescence substrate (WesternBright Sirius, Advansta, Menlo Park CA, USA) was added and imaging was performed using Proxima 2850 Imager (IsoGen Life Sciences, De Meern, The Netherlands). Quantification of signal intensity was performed using ImageJ software.

LC-MS/MS

Amphipol A8-35 at 1 mg/mL was added to both samples containing the same amount of particles as measured with NTA. Samples were vortexed and incubated for 10 minutes at room temperature (pH 7). Next the samples were reduced and alkylated with respectively 15 mM TCEP and 30 mM iodoacetamide for 15 minutes in the dark at 37° C. The samples were acidified with 5% formic acid to pH3 and spun down. The resulting protein containing pellets were re-dissolved in 0.5 mL 50 mM ammonium bicarbonate followed by overnight digestion with 2.5 µg trypsion at 37° C. Following digestion, the samples were acidified a final time to pH 3 resulting in Amphipol A8-35 precipitation. The supernatant containing the peptide material was concentrated by vacuum drying to 20 µl and 8 µl was analyzed by LC-MS/MS on the Q-Exactive mass spectrometer with a 120-minute gradient. The obtained data was searched using Maxquant against a database containing the Swiss-Prot "*Homo sapiens*" entries (version 05/2016: 20195 sequences) supplemented with the sequence of the GAG-EGFP fusion protein. Identification was carried out at a confidence level of 99%. Spectra originating from potentially contaminating proteins were identified by adding a default contaminant fasta list to the search. A minimum ratio count of two unique or razor peptides was required for quantification. Further data analysis was performed with Perseus software (version 1.5.4.1). Contaminants and reverse database hits were removed and LFQ intensities were log 2 transformed to obtain normal ratio distributions. Replicate samples were grouped. Proteins with less than three valid values in at least one group were removed and missing values were imputed from a normal distribution around the detection limit.

Immune Precipitation

MagnaBind goat anti-mouse IgG or goat anti-rabbit IgG magnetic beads (Thermo Fischer scientific, Erembodegem, Belgium) were incubated with 10 µg anti-CD81, anti-CD63, anti-PEG antibody or PBS (negative control) per 200 µL beads for 2 hours at 4° C. while rotating. Beads were washed three times with 500 µL PBS supplemented with 0.001% TWEEN®-20 (Sigma, Diegem, Belgium) and incubated with the sample containing rEV or rEV-PEG for 2 hours at 4° C. while rotating. Beads were washed three times and the supernatant was pooled and pelleted using an SW55 rotor (Beckman Coulter, Brea, CA, USA) at 100,000 g for 70 minutes.

RNA Analysis

Total RNA was isolated from vesicles using the miRNeasy Micro kit according to manufacturer's instructions (Qiagen, Valencia CA, USA). RNA concentration was measured using a UV-Vis spectrophotometer (Nanodrop Technologies, Wilmington DE, USA). GFP mRNA expression analysis in rEV was performed via quantitative real-time polymerase chain reaction (PCR) (RT-qPCR) using PrimePCR assays (Bio-Rad). The 10.0 µL PCR reaction mix contained PrimePCR Assay (0.5 µL), SsoAdvanced SYBR Green Supermix (5.0 µL), cDNA (1 µL corresponding to the cDNA reverse transcribed from approximately 10 ng RNA), and nuclease-free water (4.5 L). The 384-well plate was then run on the CFX 384 (Bio-Rad) at 95° C. for 30 seconds, then 95° C. for 5 seconds and 60° C. for 15 seconds (for 45 cycles). Following primers were used: EGFP primer pair 1 with forward sequence ACGACGGCAACTACAAGAC (SEQ ID NO:1) and reverse sequence TCCTTGAAGTC-GATGCCCTT (SEQ ID NO:2) and EGFP primer pair 2 with forward sequence TAAACGGCCACAAGTTCAGC (SEQ ID NO:3) and reverse sequence GAACTTCAGGGTCAGCTTGC (SEQ ID NO:4). Data were processed and normalized using qbase+2.6 software.

Lipid Analysis

Lipids were extracted using a modified Bligh-Dyer protocol and phospholipids were analyzed by electrospray ionization tandem mass spectrometry (ESI-MS/MS) on a hybrid triple quadrupole linear ion trap mass spectrometer (4000 QTRAP, AB SCIEX, Framingham, Massachusetts, USA) equipped with a robotic sample injection and ionization device (TriVersa NanoMate, Advion). The collision energy was varied as follows: prec 184, 50 eV; nl 141, 35 eV; nl 87, −40 eV; prec 241, −55 eV. The system was operated in the multiple reaction monitoring (MRM) mode for quantification of individual species. To quantify the total amount of phospholipids, the abundances of individually measured species within each phospholipid class were summed and normalized based on the amount of protein. Total cholesterol concentrations were measured with the Amplex Red Cholesterol Assay Kit (A12216, Invitrogen) following manufacturer's instructions.

rEV PEGylation rEV (2E10) were incubated in 100 µL of 0.015 µg/mL DMPE-PEG 5k (PG1-DM-5K, Nanocs, NY, USA) at 40° C. for 2 hours while being gently mixed.

Lyophilization

For lyophilization, samples were diluted 1:200 in 1 mL PBS containing 5% trehalose to a final concentration higher then $5 \times 10^{10}$ particles/mL. The vials were placed on pre-cooled shelves at −45° C. for 2 hours after which the chamber pressure was lowered until 0.1 mbar. From the moment the desired pressure was reached, the shelf temperature was increased at 1° C./minute to −25° C. and maintained for 24 hours. When all ice was completely sublimated the temperature was increased at 0.15° C./minute to the final drying temperature of 20° C. and this temperature was maintained for 4 hours. Finally the temperature was decreased again at 1° C./minute to a storage temperature of 3° C. while maintaining the vacuum until the cycle was stopped.

Example 1: Recombinant Extracellular Vesicles (rEV) Share Physical and Biochemical Characteristics with Endogenous Sample Extracellular Vesicles (Sample EV)

Figure 1B:
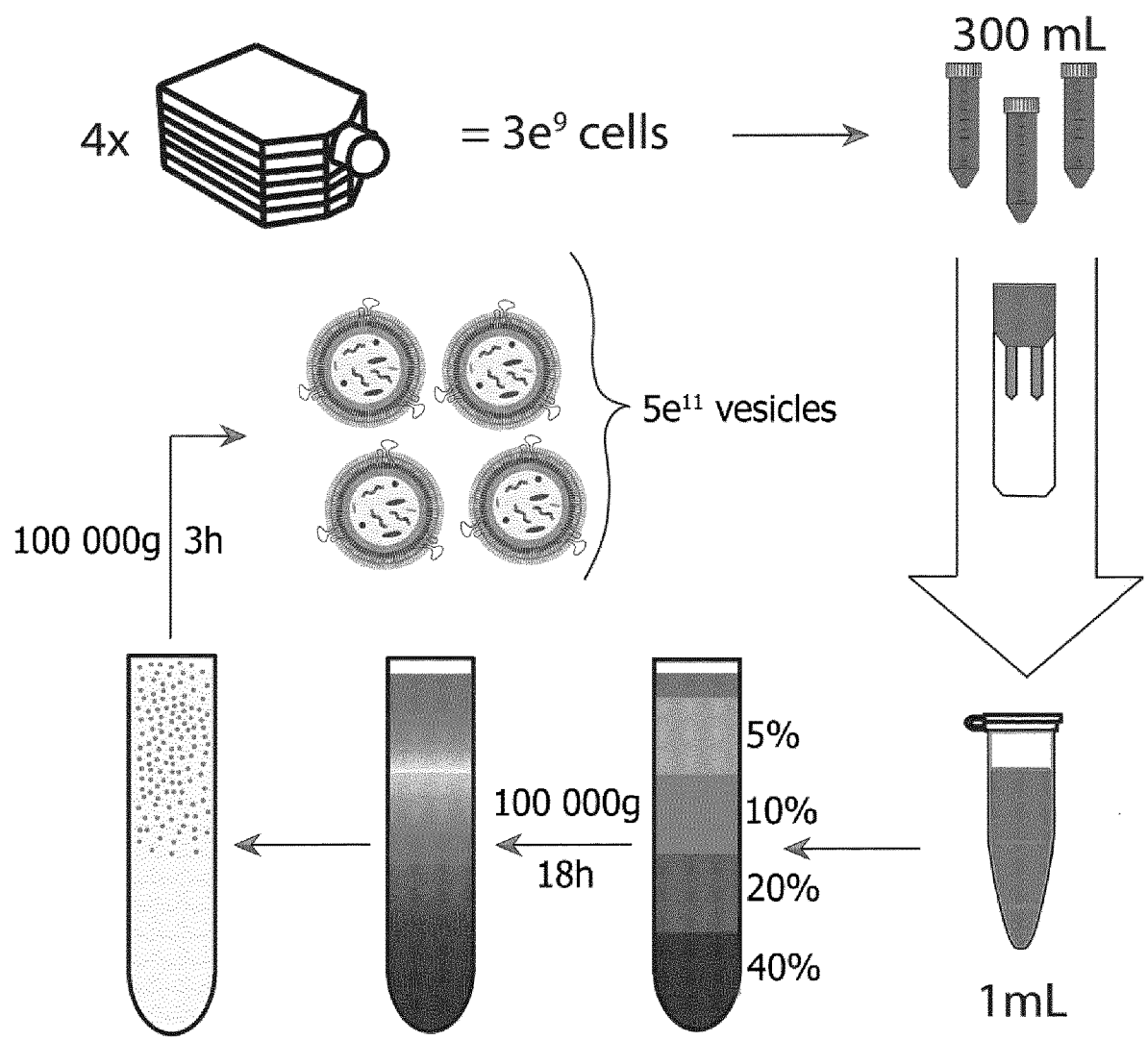
Figure 1C:
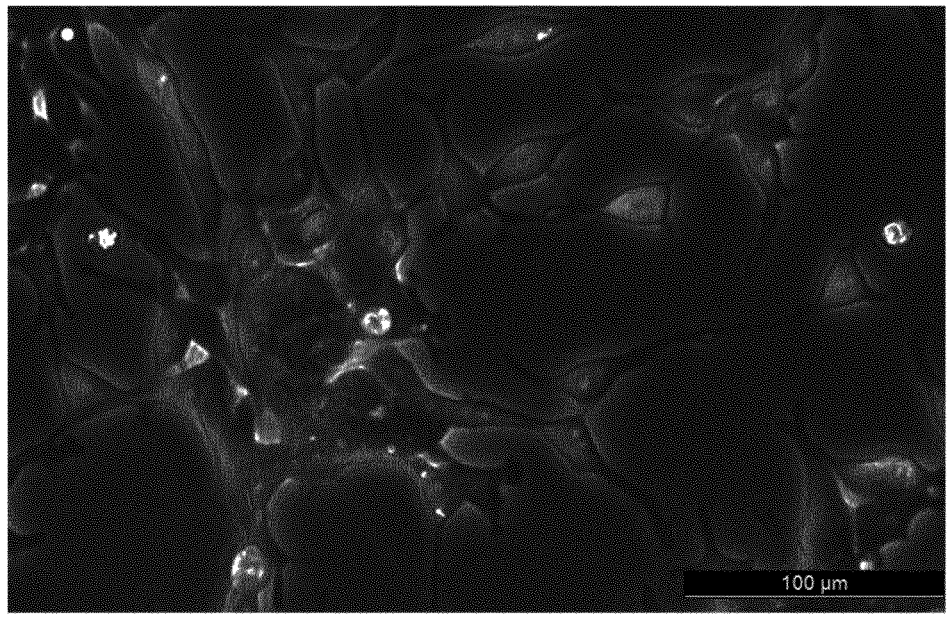
Figure 1C:
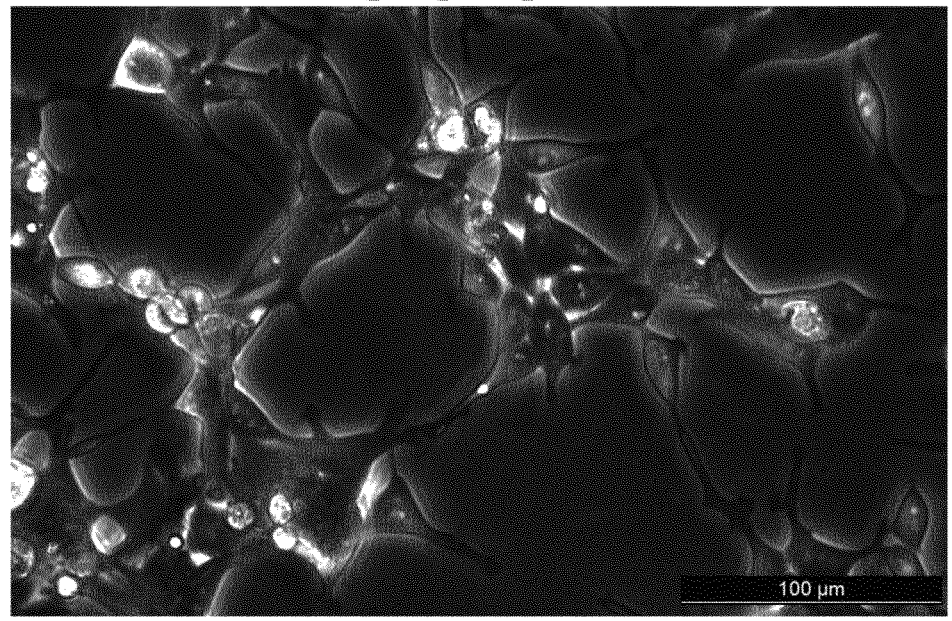
Figure 1D:
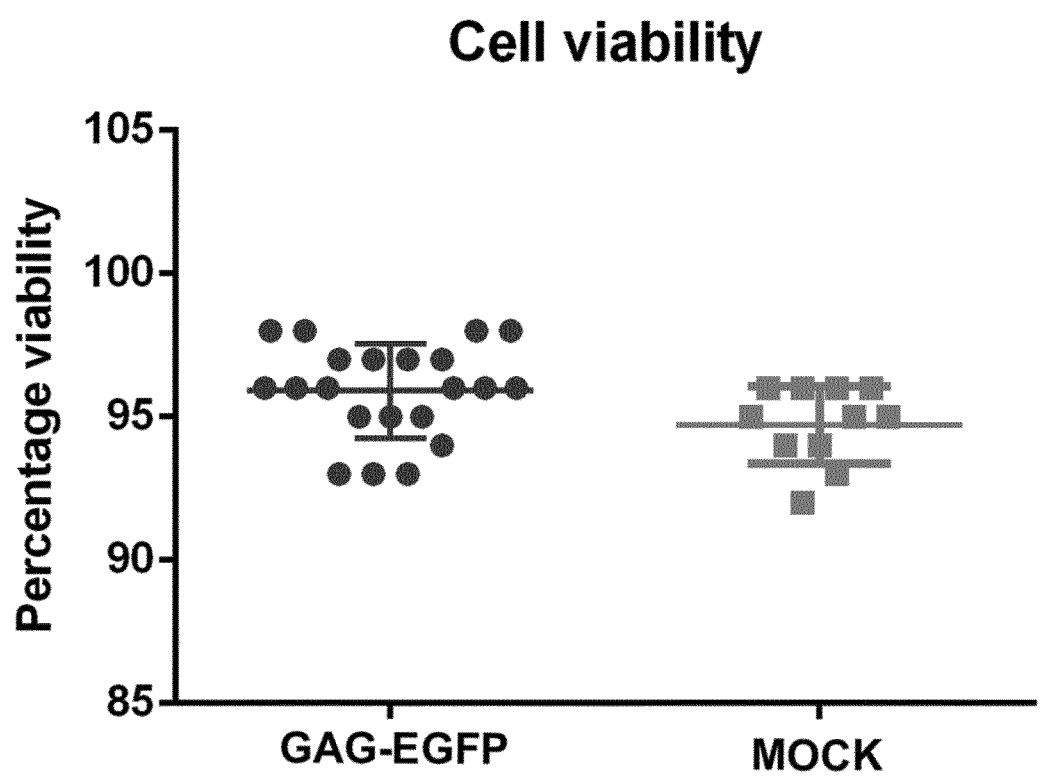
Figure 1E:
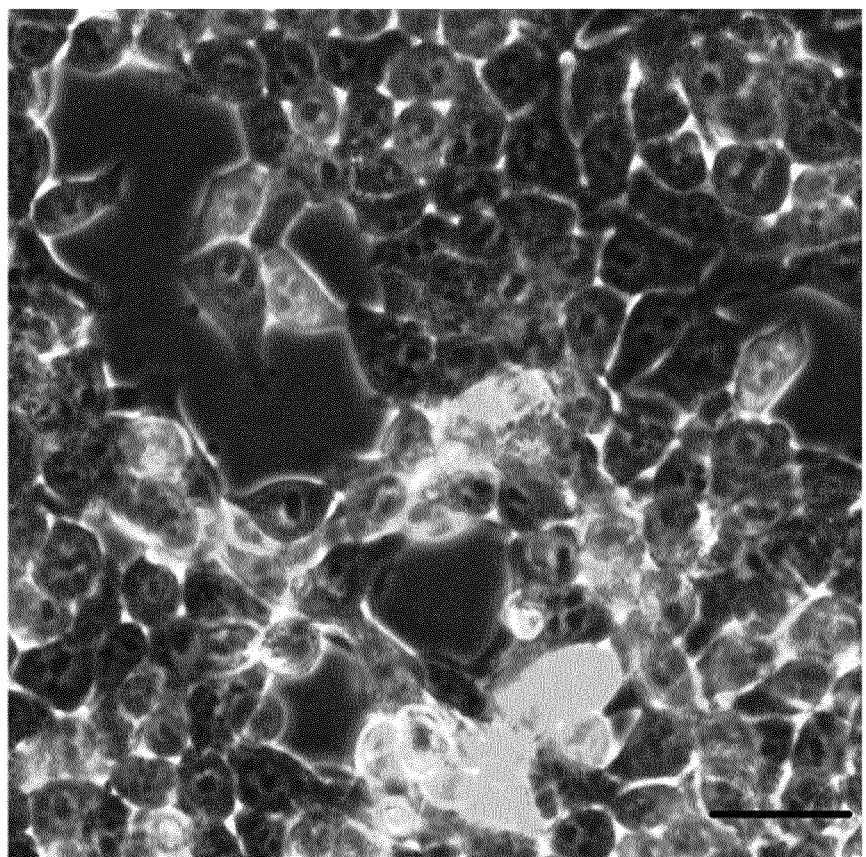
Figure 1F:
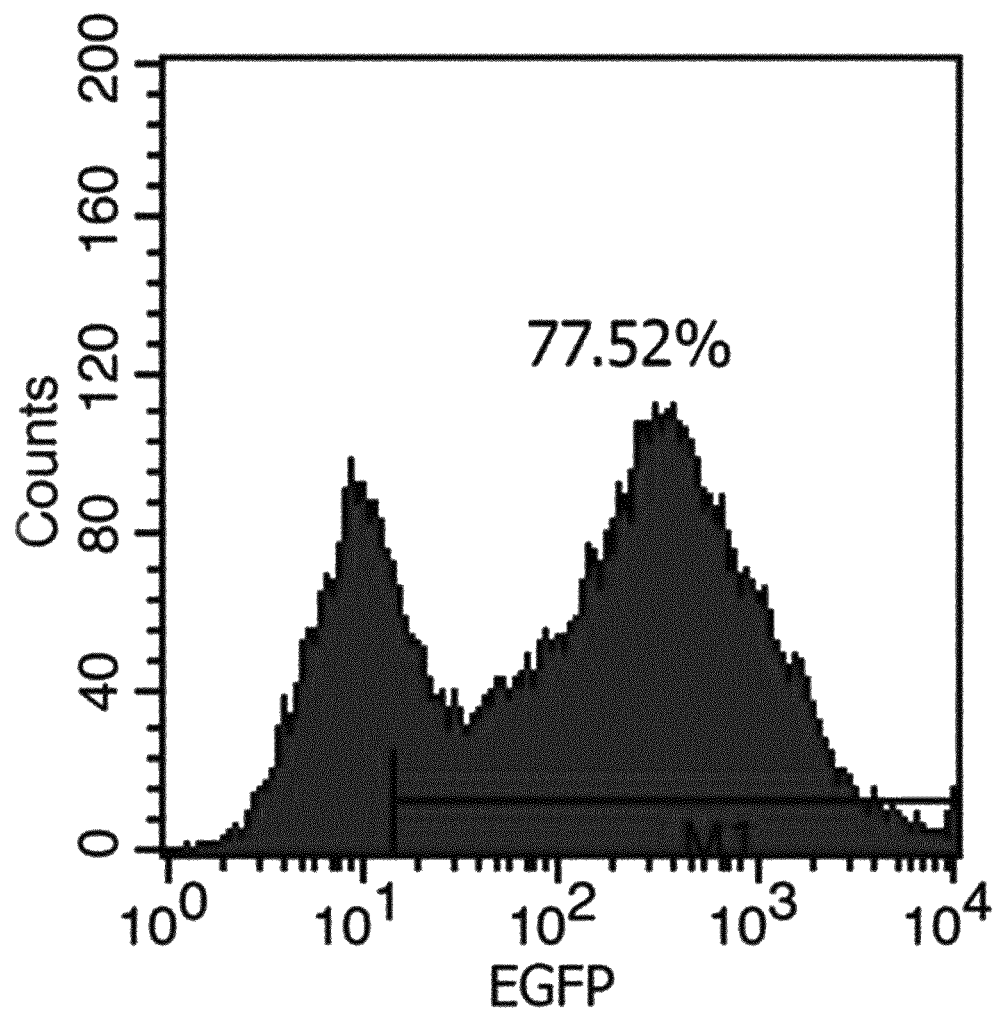
Figure 1G:
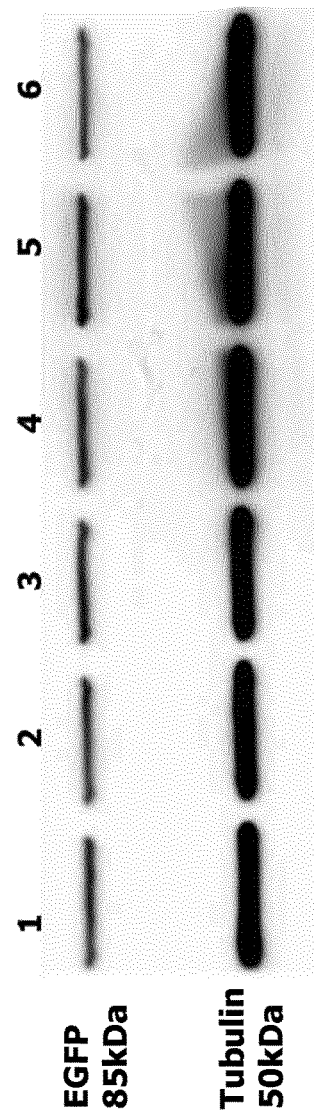
Figure 1H:
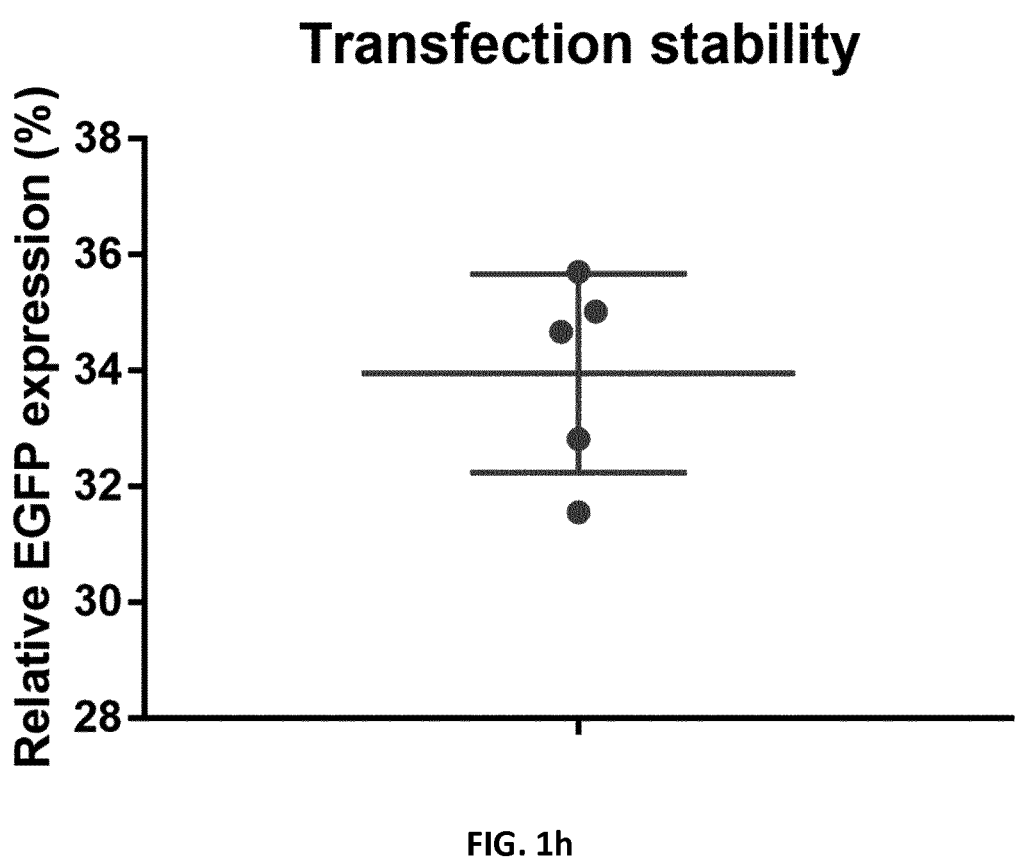
Figure 2A:
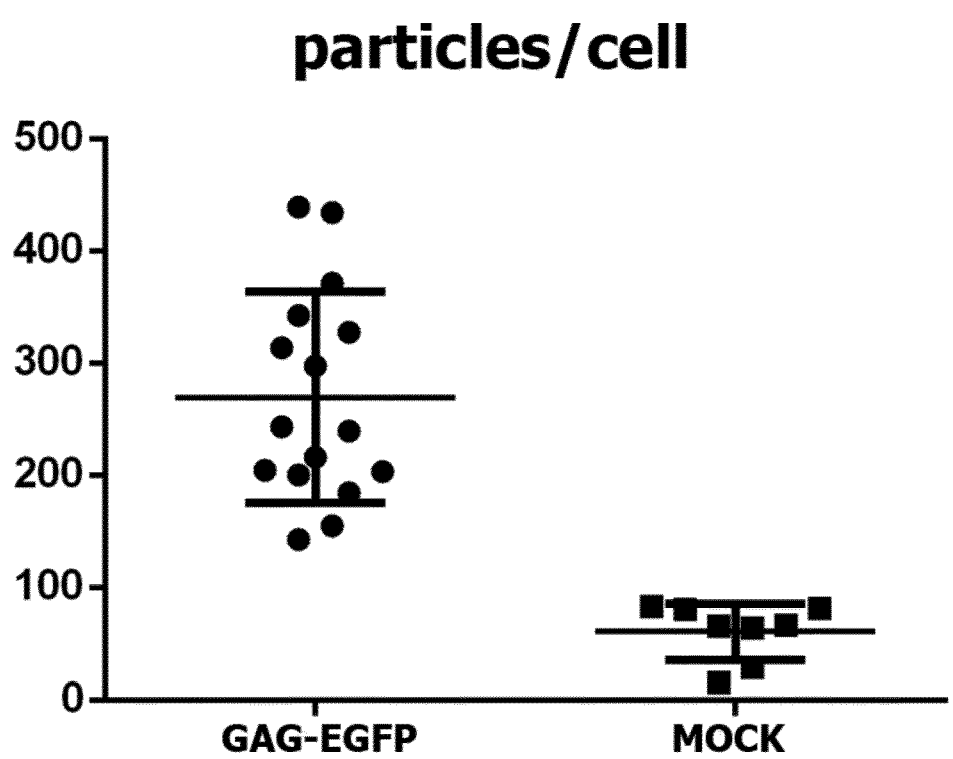
FIGS. 2a-2g: rEV reflect physical and biochemical characteristics of sample EV.

For the production for rEV, use was made of the overexpression of a fusion protein of the retroviral group-specific antigen (Gag) polyprotein C-terminally linked with enhanced green fluorescent protein (EGFP). rEV was isolated from the conditioned medium (CM) 72 hours after transfection of approximately $3 \times 10^9$ HEK293T cells with Gag-EGFP DNA by Optiprep density gradient ultracentrifugation (ODG) and consecutive pelleting resulting in approximately $5 \times 10^{11}$ vesicles (FIG. 1b). Transfection efficiency, calculated by flow cytometry and fluorescence microscopy, was on average 75% (FIGS. 1e, 1f) with no significant changes in morphology and cell viability compared to MOCK-transfected cells (FIGS. 1c, 1d). Western Blot analysis for EGFP of 6 transfections at different time points proved that Gag-EGFP transfection was reproducible (FIGS. 1g, 1h). Expression of the Gag-EGFP fusion protein resulted in more than 5 times more particles per cell compared to MOCK-transfected cells (FIG. 2a).

To check the similarity of rEV with sample EV, EV from both Gag-EGFP (rEV) and MOCK-transfected HEK293T cells (MOCK EV) were compared on the basis of physical and biochemical characteristics previously found to be important for a possible EV reference material.[16]

Figure 2B:
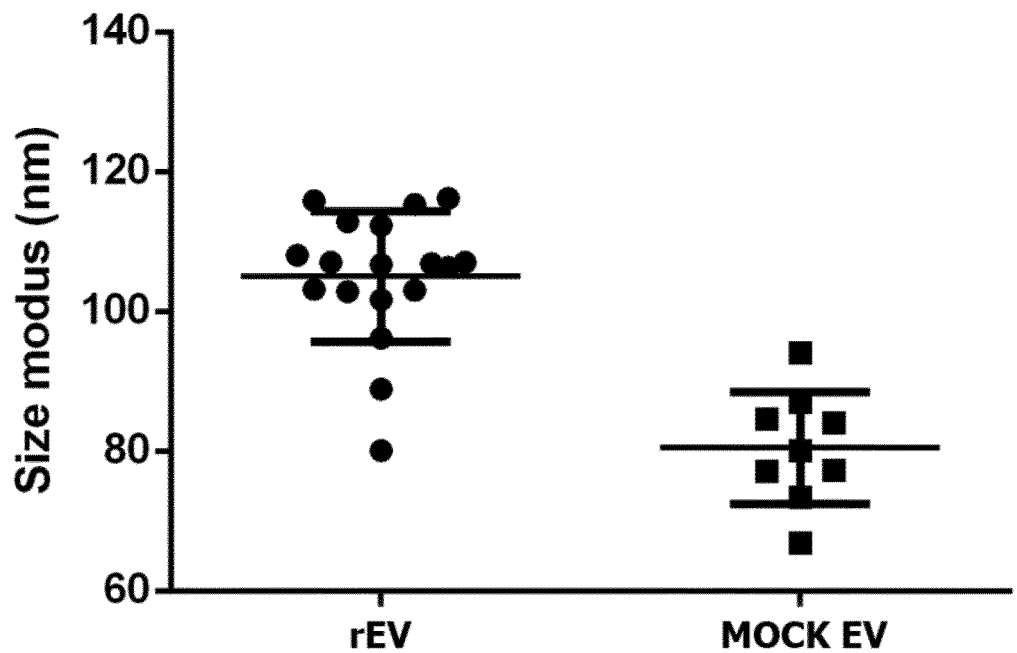
Figure 2C:
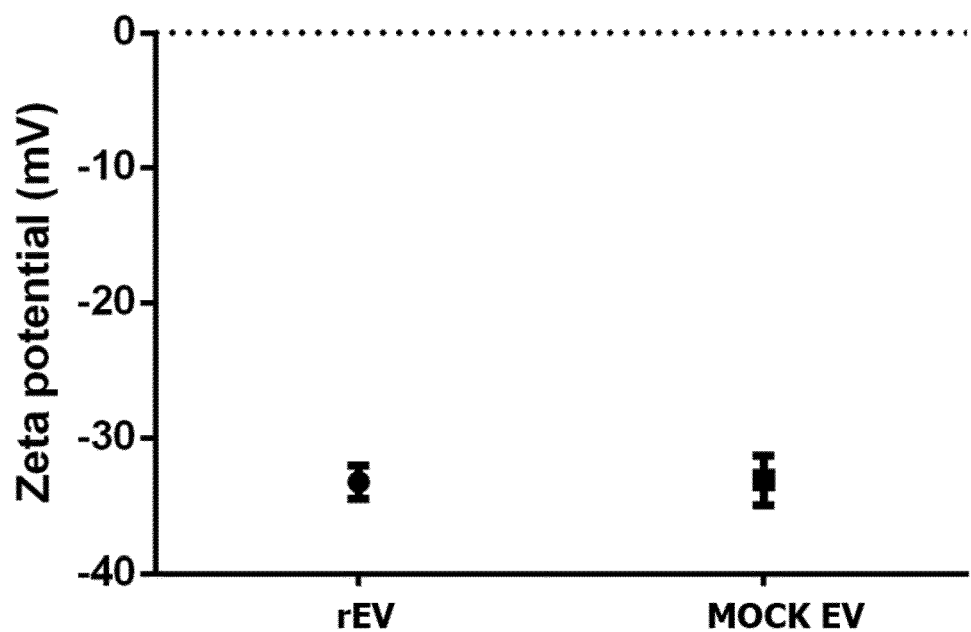
Figure 2D:
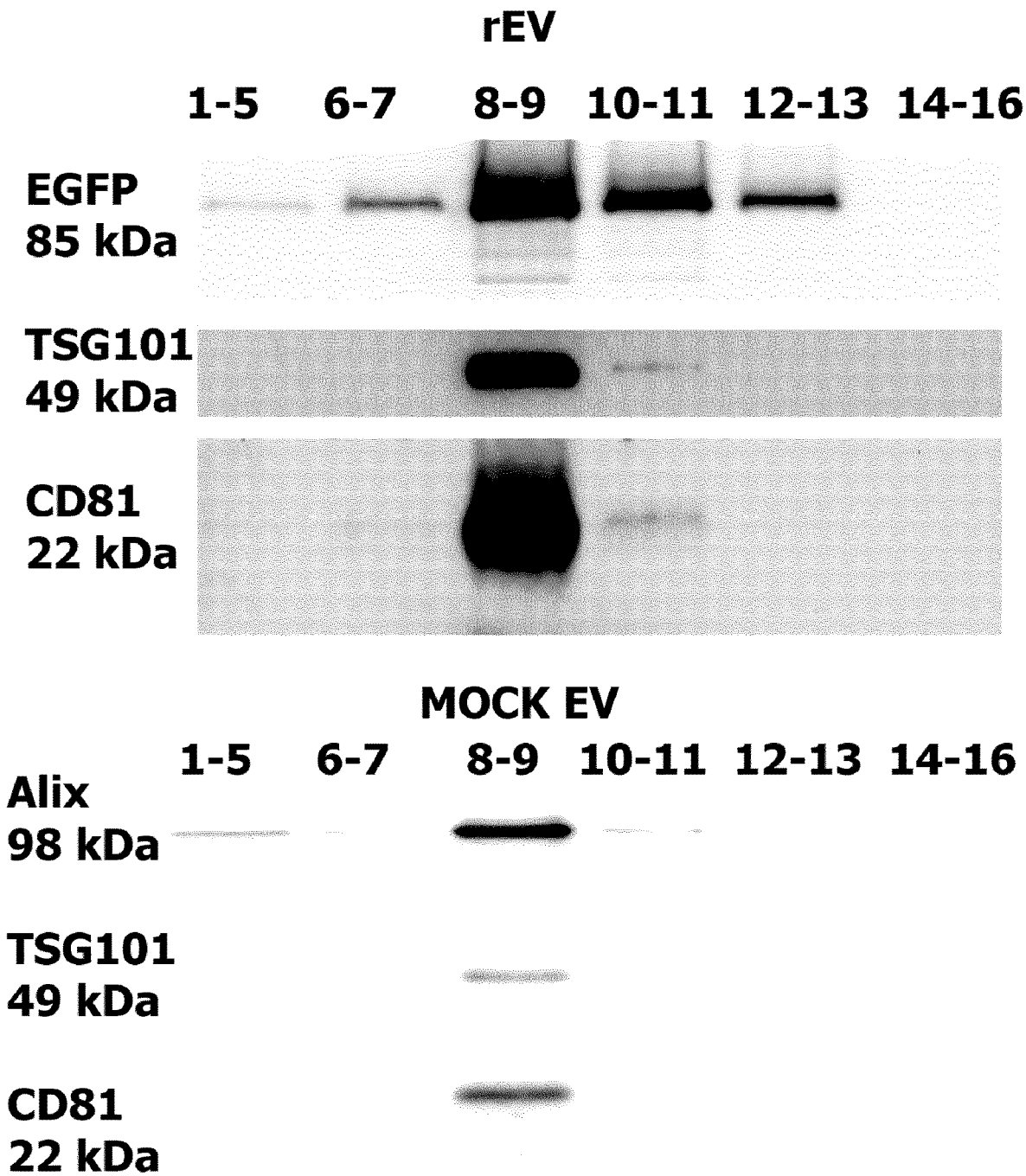
Figure 2E:
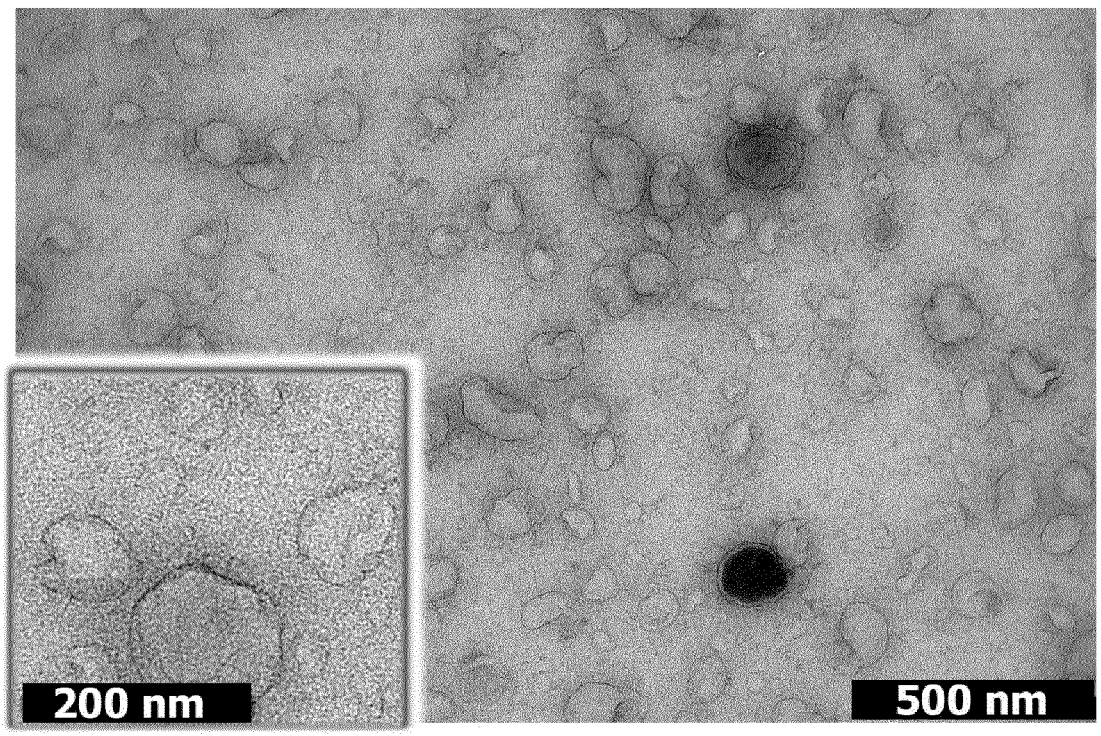
Figure 2E:
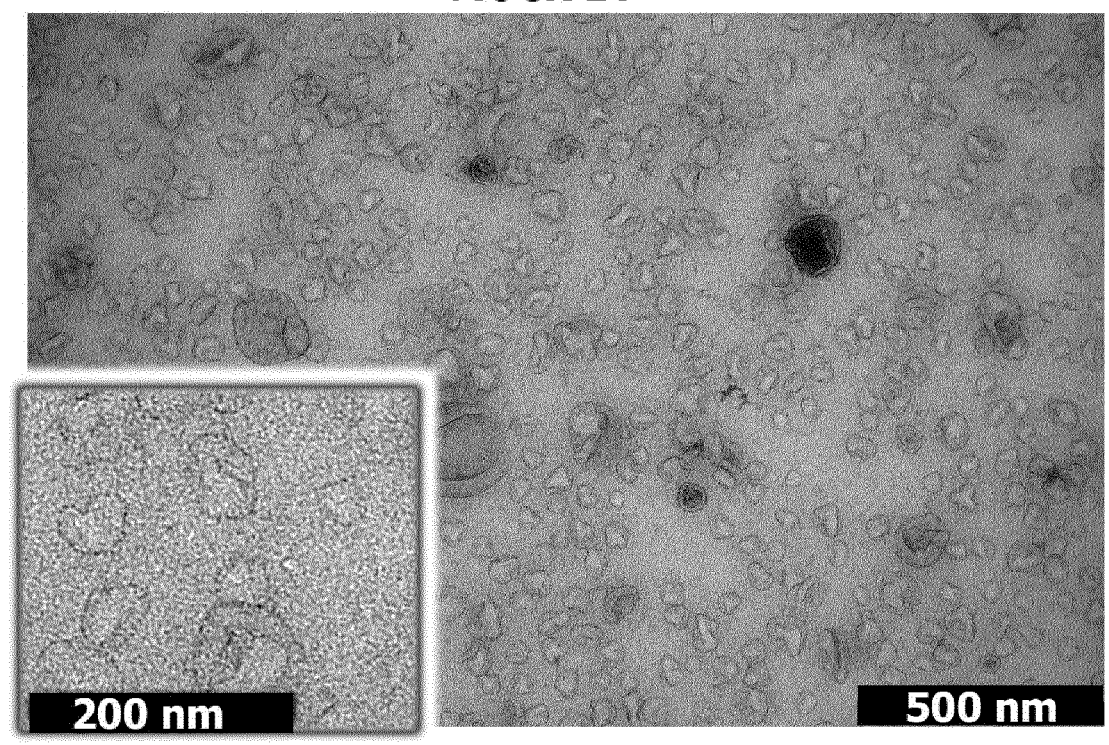
Figure 2F:
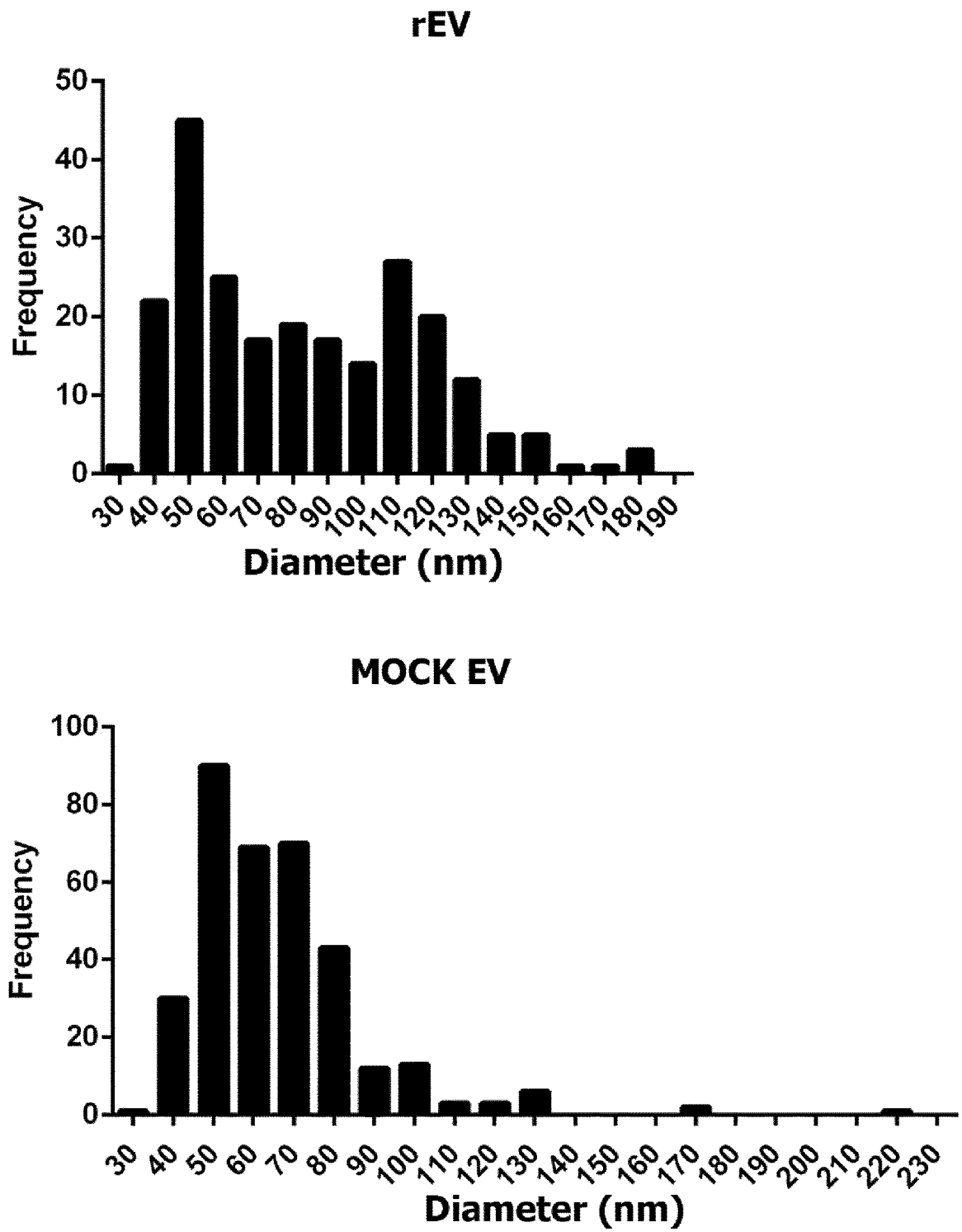
Figure 2G:
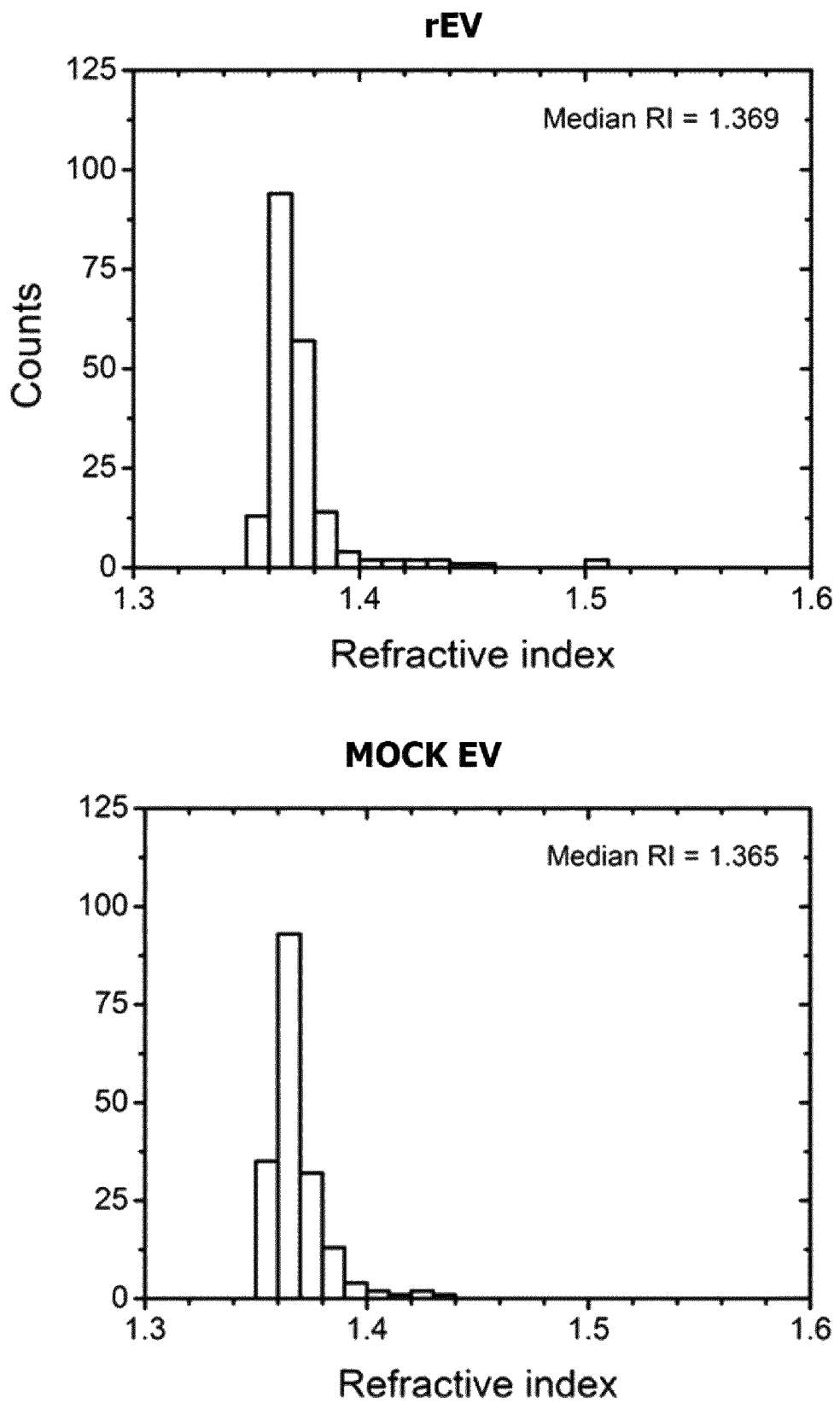

Nano particle tracking analysis (NTA) showed a 24.51 nm±3.631 bigger mean size modus for rEV compared to MOCK EV (FIG. 2b), but showed a 7.769 nm±3.246 smaller and similar mean size modus as EV isolated from Rab27b-transfected and WT human MCF7 breast cancer cells, mouse 4T1 breast cancer cells and human cancer-associated fibroblasts respectively and a similar mean size modus as EV isolated from plasma and urine. The average zeta potential for rEV in water was similar to those of EV from different cell lines and biofluids (−34 mV) and Western blot analysis of all top-to-bottom ODG fractions from CM of GAG-EGFP and MOCK-transfected HEK293T cells identified EV enriched proteins TSG101, CD81 and Alix in fraction 8-9 corresponding to a buoyant density of 1.094 g/mL (FIGS. 2c, 2d).[26] EGFP was characterized by a Gaussian distribution, with the highest protein levels in the EV enriched fraction of CM. EM images visualized a heterogeneous population of vesicles in rEV and MOCK EV samples with similar morphology and size distributions, in agreement with NTA measurements (FIGS. 2e, 2f). The RI of rEV, calculated by Mie theory and flow-SR, is approximately 1.36, corresponding to the RI of MOCK EV and EV from various sources (FIG. 2g).

Figure 3A:
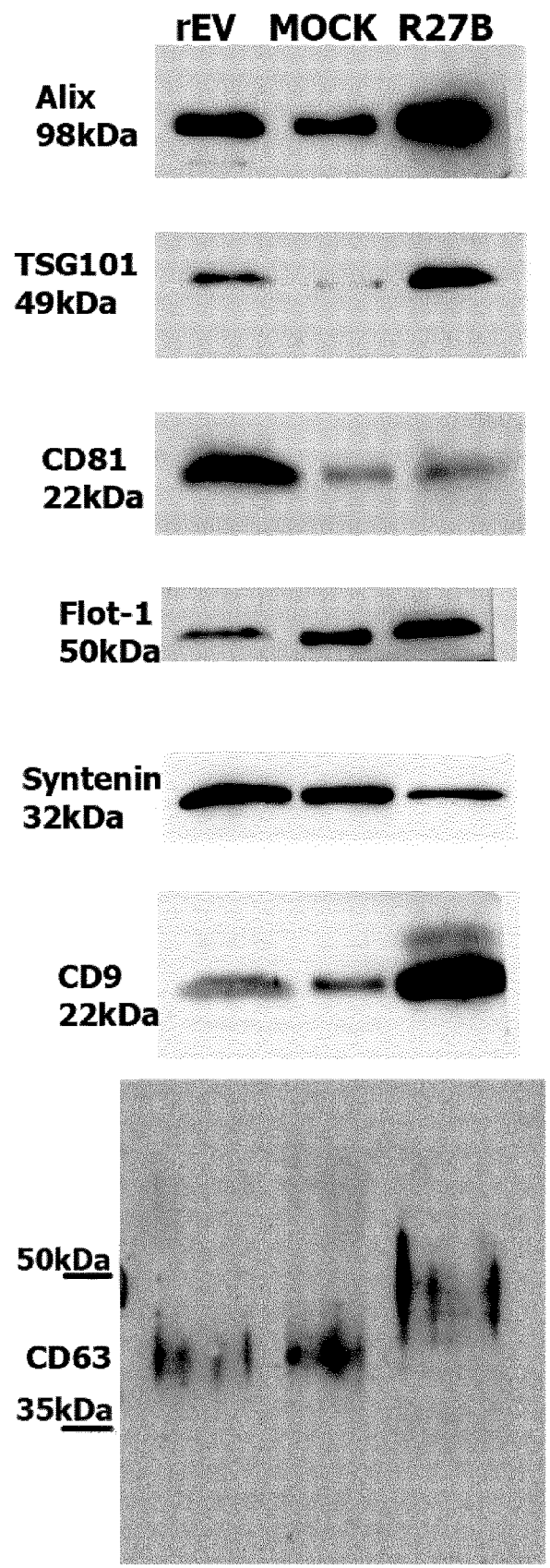
FIGS. 3a-3e: Proteomic comparison of rEV and sample EV.
Figure 3B:
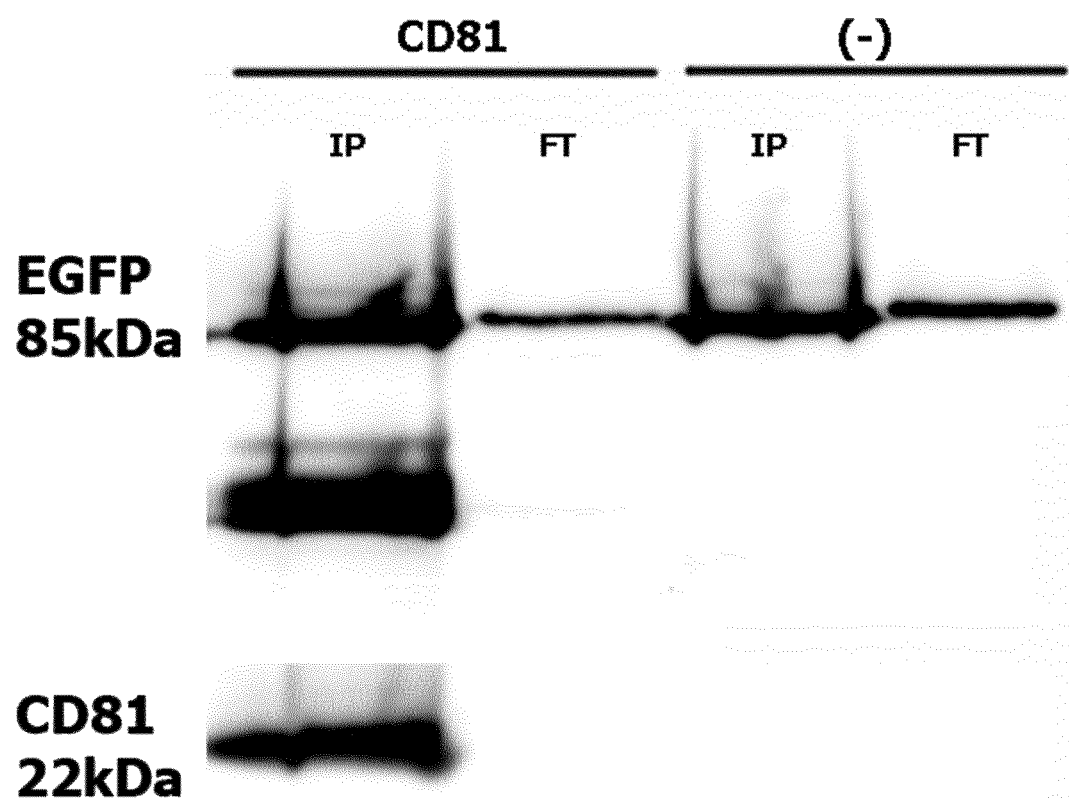
Figure 3C:
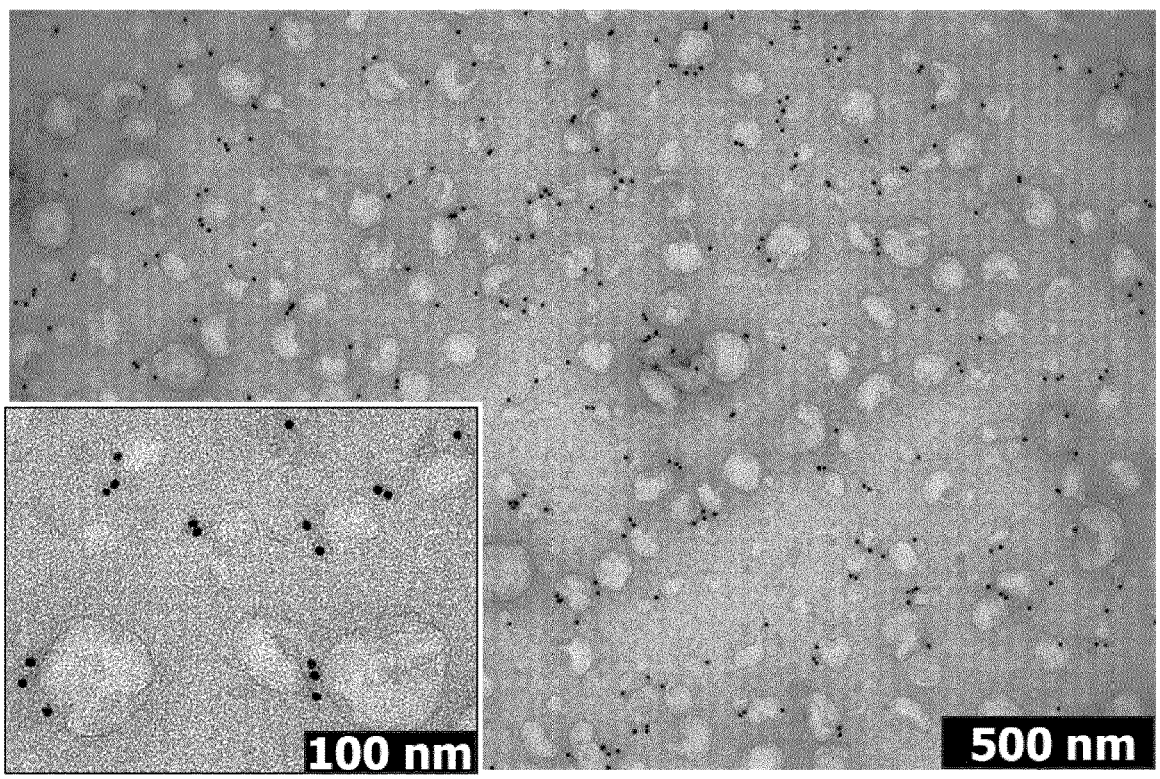
Figure 3C:
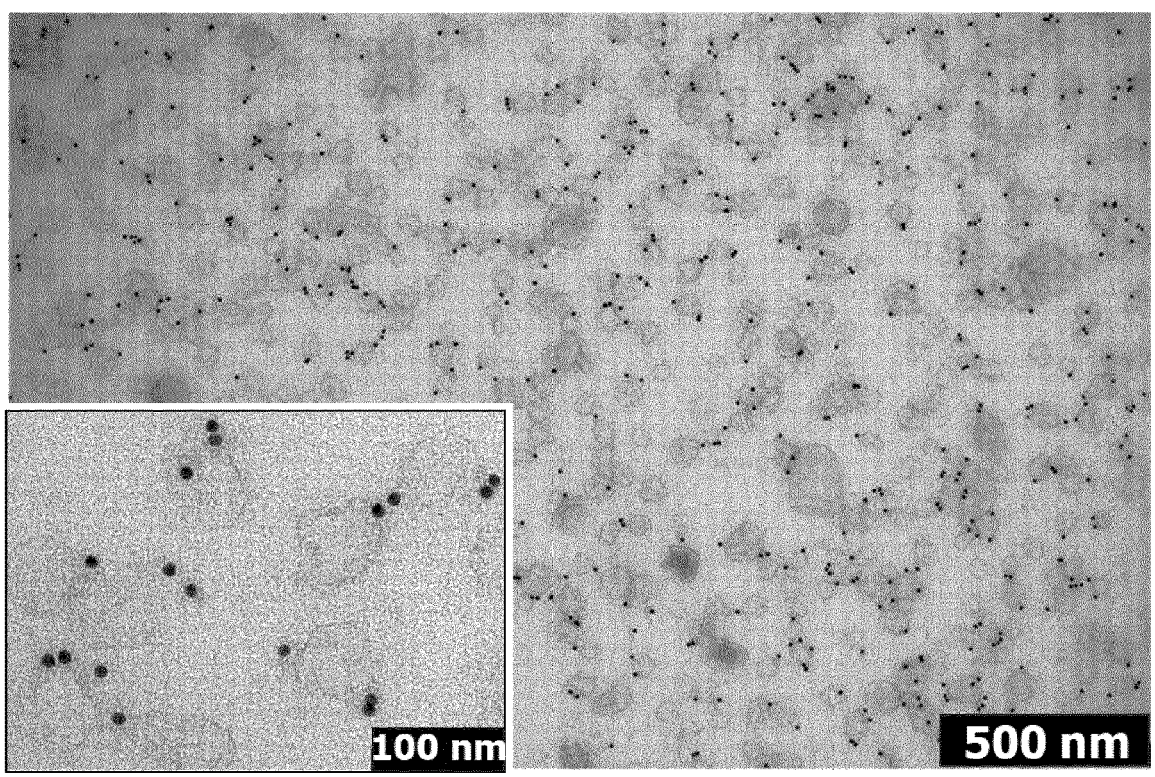
Figure 3D:
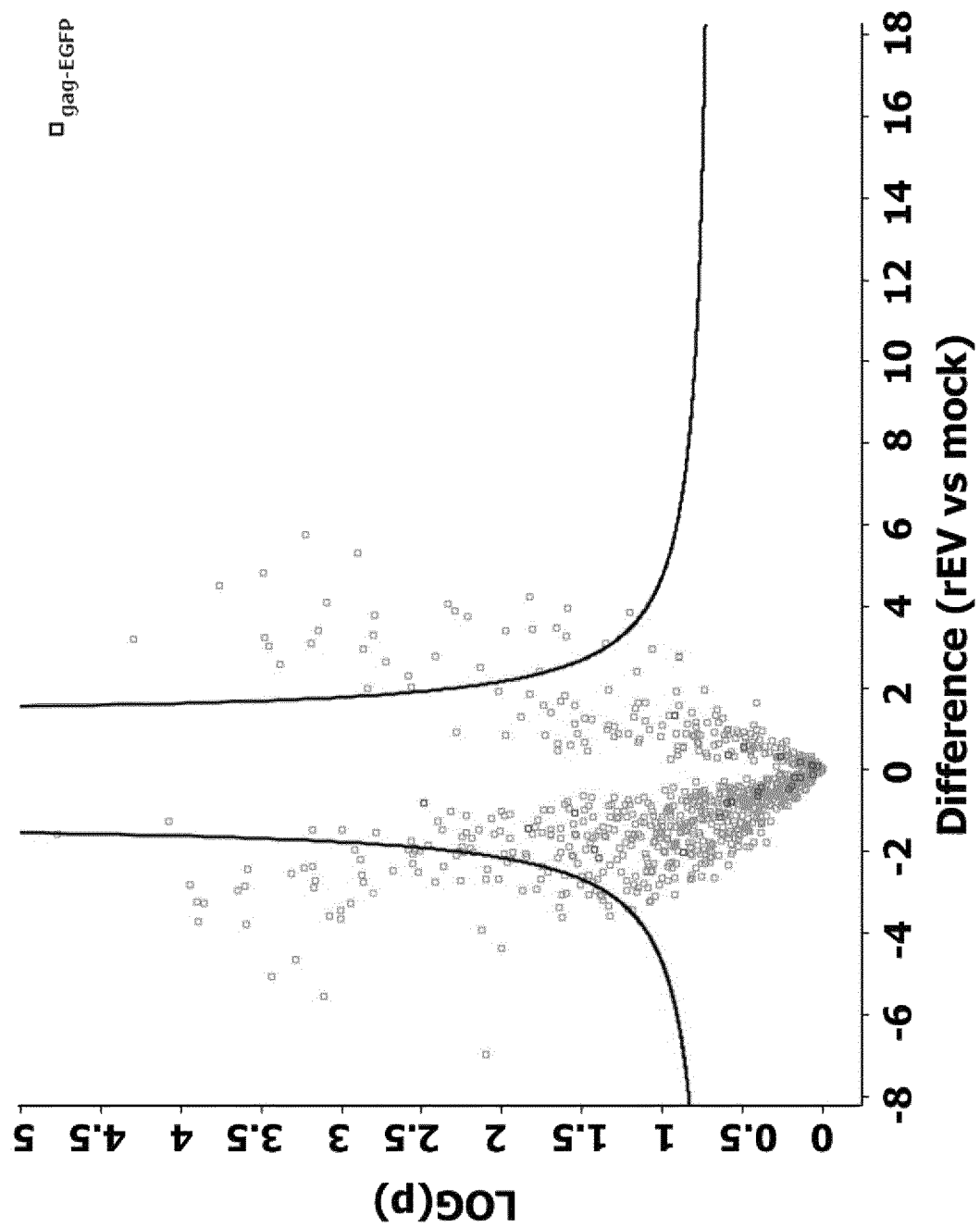
Figure 3E:
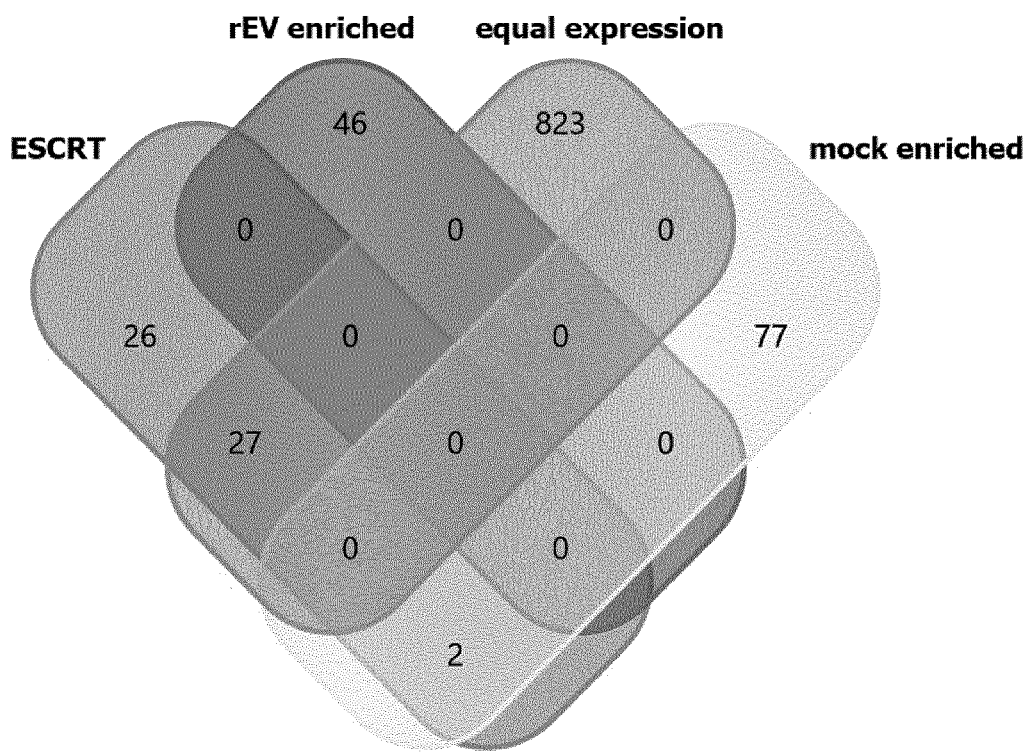

Western blot analysis of rEV, MOCK EV and EV isolated from Rab27b overexpressing MCF7 cells identified the presence of EV enriched proteins Alix, TSG101, CD81, Flotillin-1, syntenin-1 and CD9 (FIG. 3a). The CD63 smear differed between rEV and MOCK EV, and EV isolated from MCF7 cells. Immune capture of rEV with anti-CD81, anti-CD63 or anti-CD9-coated magnetic beads confirmed the co-isolation of CD81, CD63 or CD9 with GAG-EGFP (FIG. 3b). Immunoelectron microscopy (IEM) with a gold labelled secondary antibody recognizing anti-CD63 antibody targeting an epitope in the large extracellular loop, confirmed the presence of CD63 in the membrane of rEV (FIG. 3c).

rEV and MOCK EV proteins isolated by ODG followed by size exclusion chromatography (SEC) were trypsin digested and analyzed by LC-MS/MS followed by quantification of the identified proteins by a label-free approach. A total of 869 and 900 proteins were identified in rEV and MOCK EV, respectively, of which 46 and 77 proteins were significantly enriched in rEV and MOCK EV, respectively. In the group of proteins that were equally expressed in rEV and MOCK EV (n=823), most EV-associated proteins were found (FIG. 3d). When ESCRT-associated proteins were compared, proteins that play a role in EV biogenesis, with rEV and MOCK EV enriched and equally expressed proteins, it was found that 27 ESCRT-associated proteins were equally expressed in rEv and MOCK EV; only 2 were significantly enriched in MOCK EV, whereas no ESCRT-associated proteins were significantly enriched in rEV (FIG. 3e).

Figure 4A:
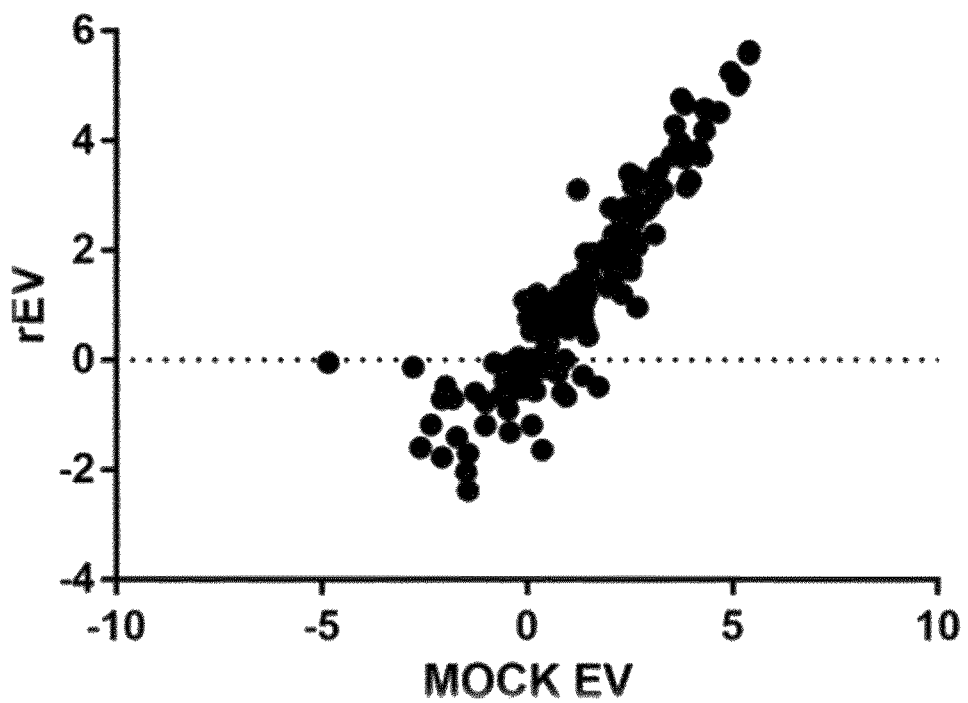
FIGS. 4a and 4b: Lipidomic comparison of rEV and MOCK EV.
Figure 4B:
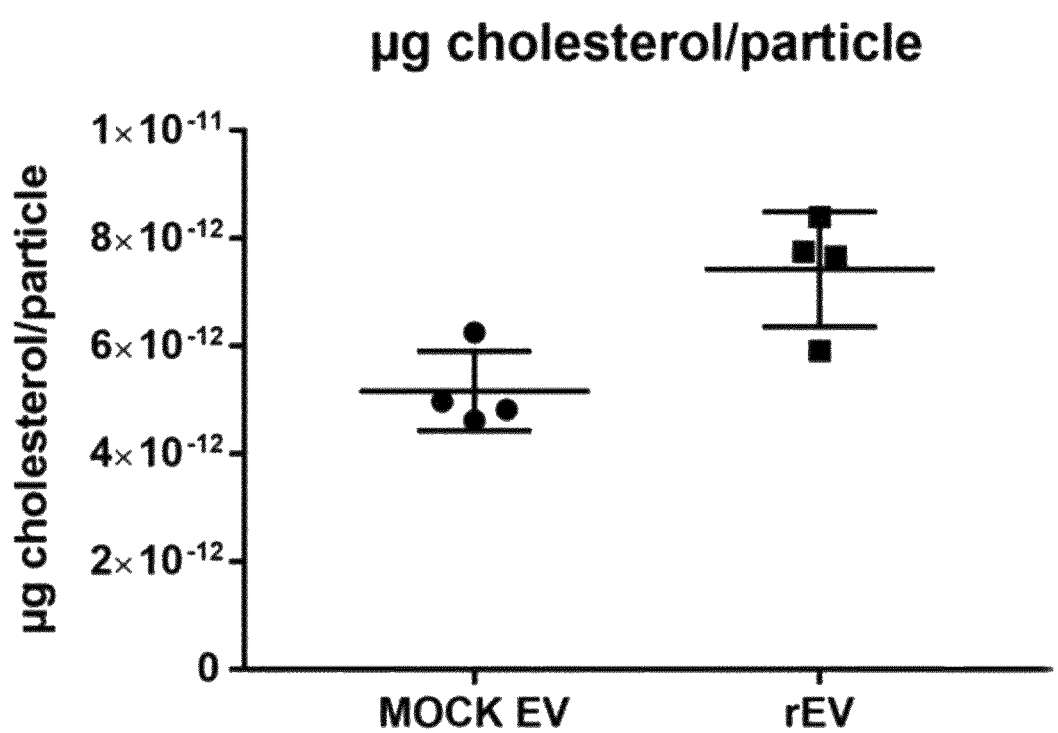

In addition, mass-spectrometry-based lipidomics was also performed for phospholipids, sphingomyelins, ceramides and lysophospholipids on three biological replicates of both rEV and MOCK EV. A positive correlation was found between the lipid composition of rEV and MOCK EV except for one phospholipid, PS 32:1, which was 5 times more expressed in rEV compared to MOCK EV (FIG. 4a). Assessment of the cholesterol concentration per particle of rEV and MOCK EV via a colorimetric kit, however, revealed a significant difference of $2.265 \times 10^{-12} \pm 6.479 \times 10^{-13}$ µg cholesterol/particle more for rEV in comparison with MOCK EV (p=0.0129), but similar to cholesterol concentrations of EV isolated from different cell cultures and biofluids (FIG. 4b). This was expected due to the high number of membrane-bound Gag-EGFP molecules organized into cholesterol containing lipid rafts.[36, 37]

Example 2: Identification of rEV Detection Methods

Different detection methods were analyzed for their ability to quantify rEV in the presence of sample EV by exploiting its fluorescent and non-human Gag-EGFP fusion protein.

Figure 5A:
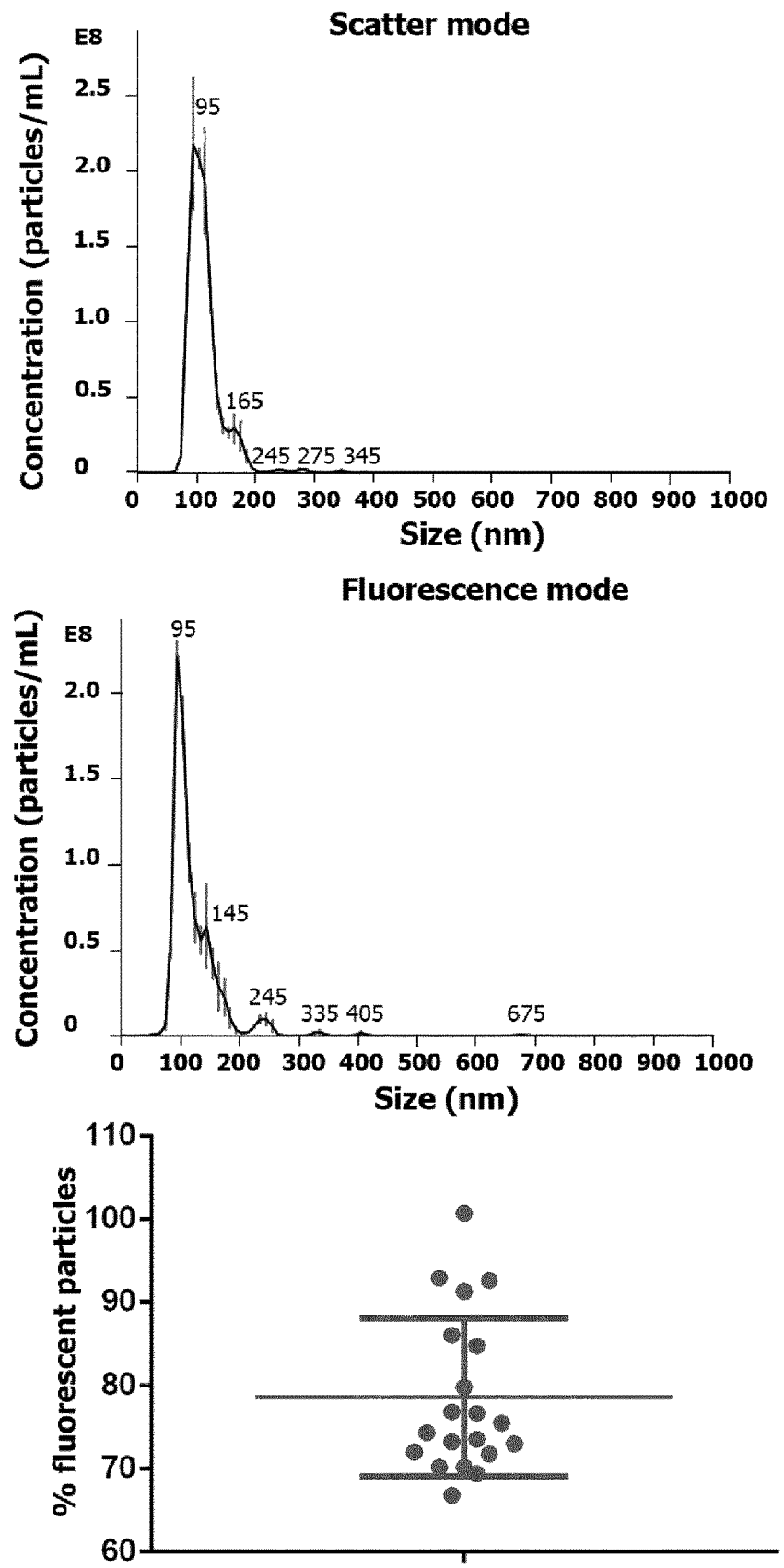
FIGS. 5a-5f: Read-out possibilities of rEV.
Figure 5B:
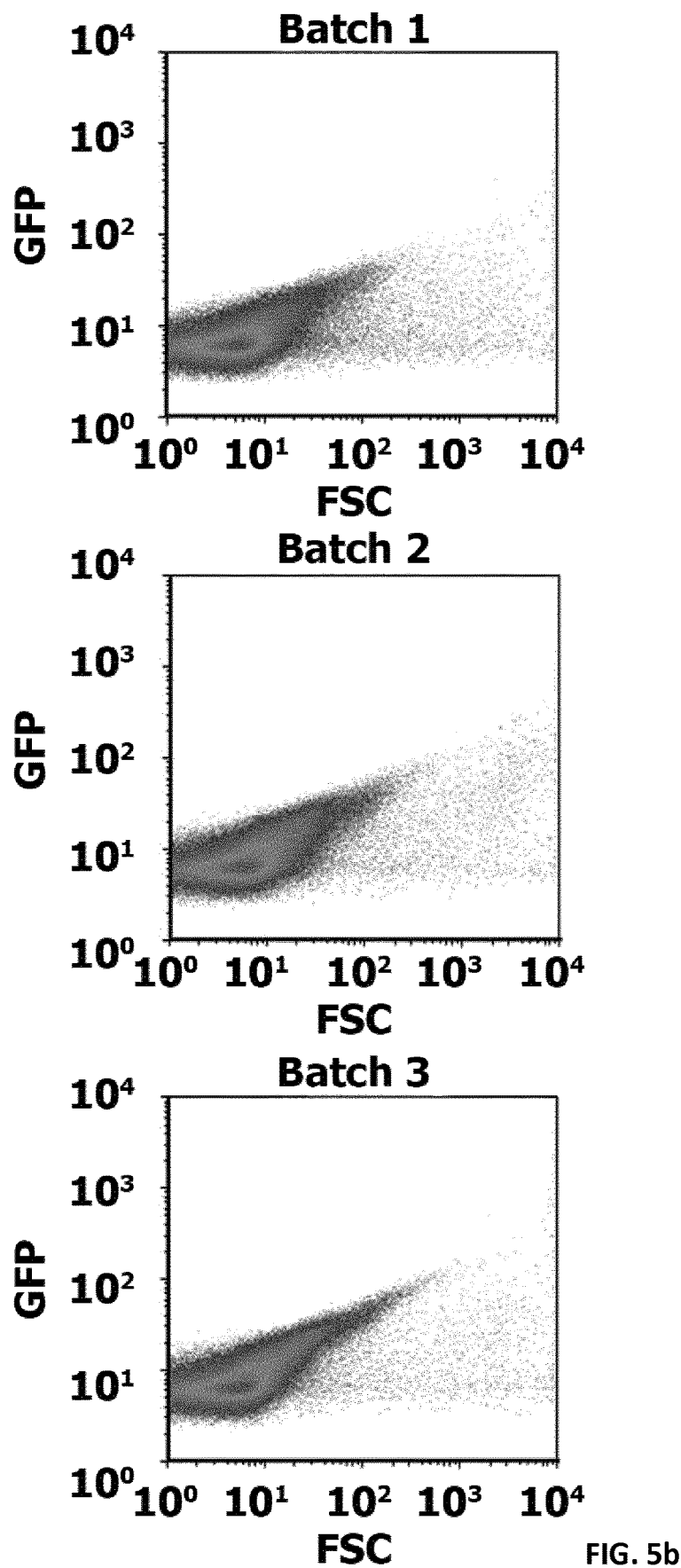
Figure 5C:
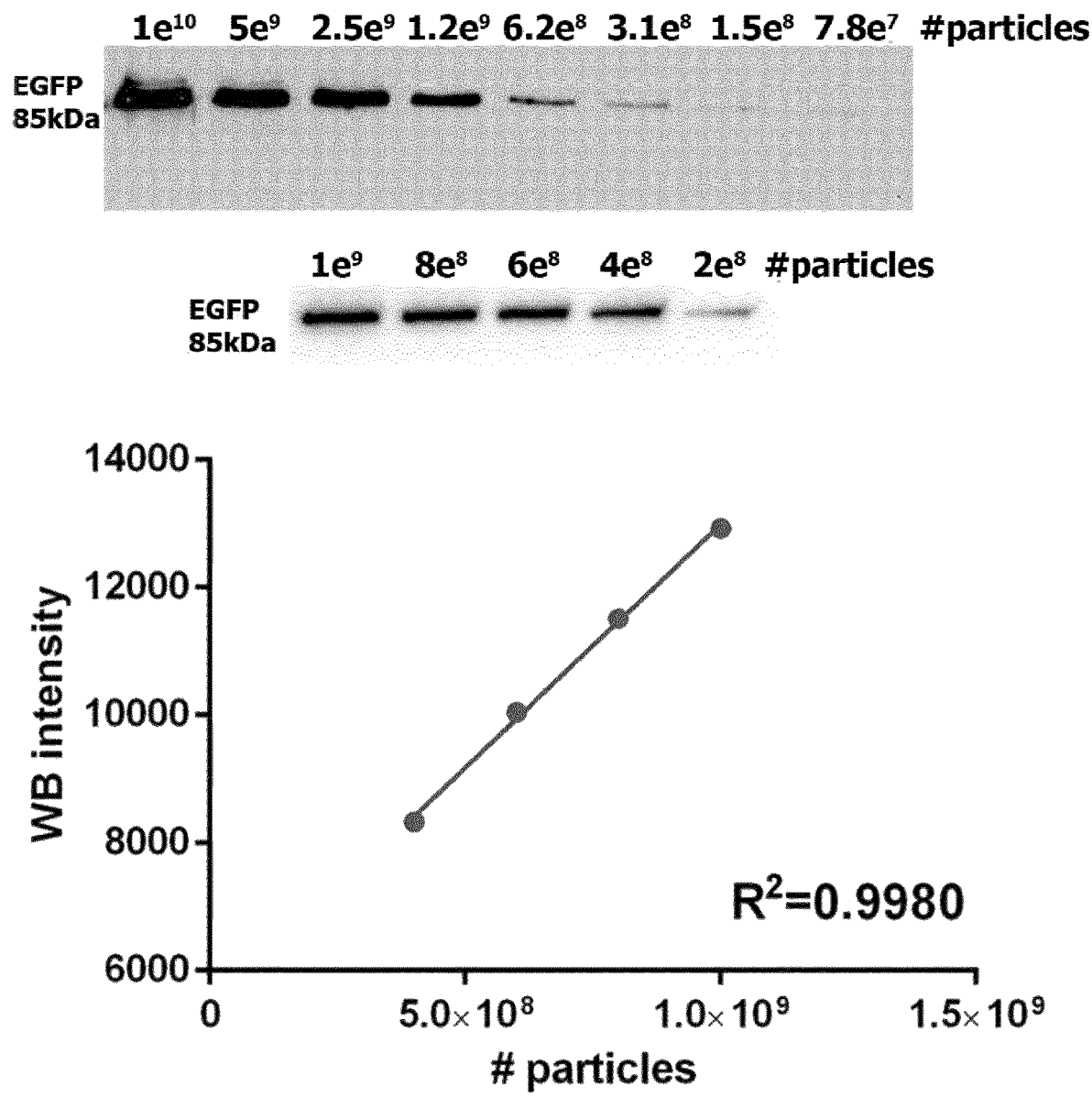
Figure 5D:
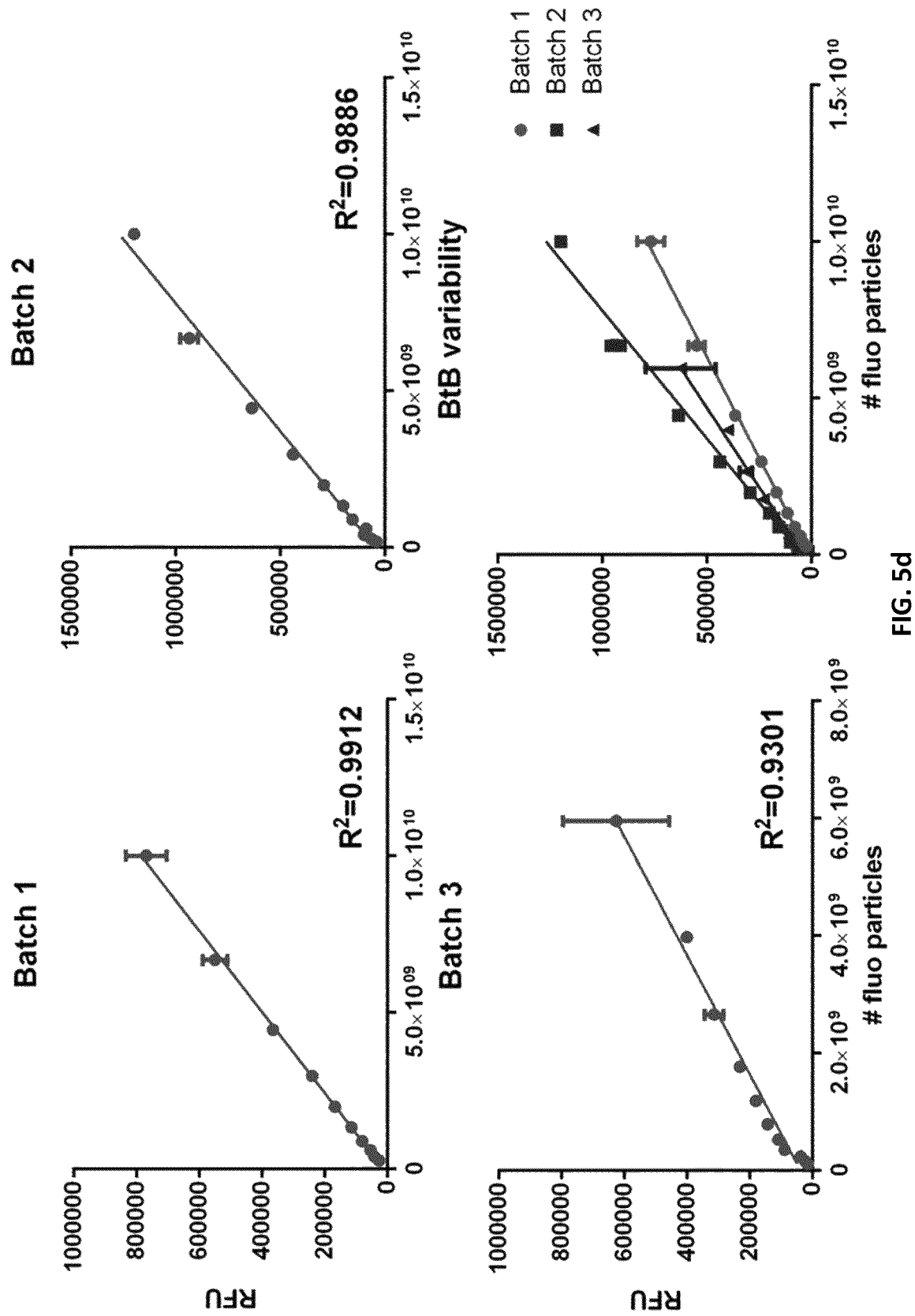
Figure 5E:
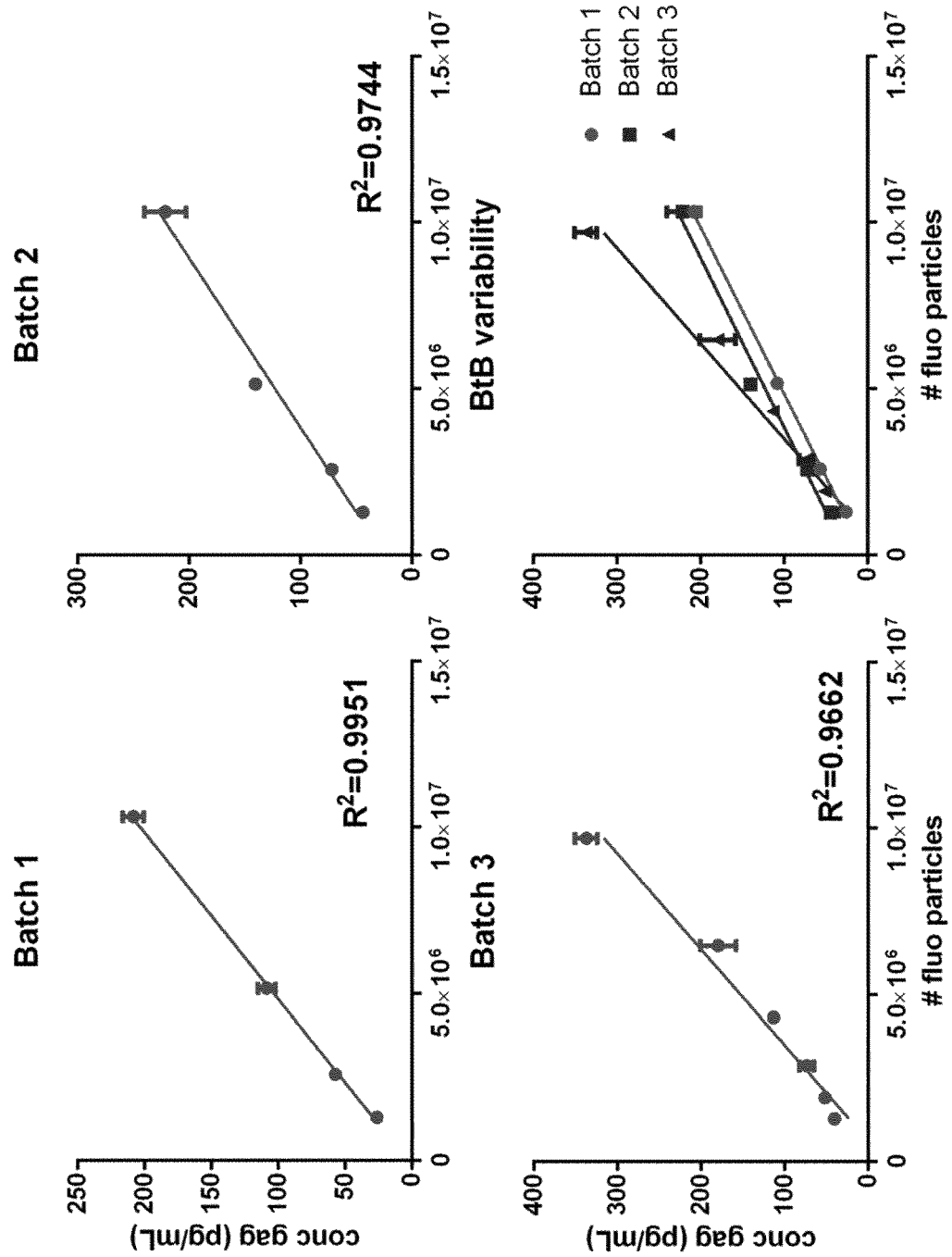
Figure 5F:
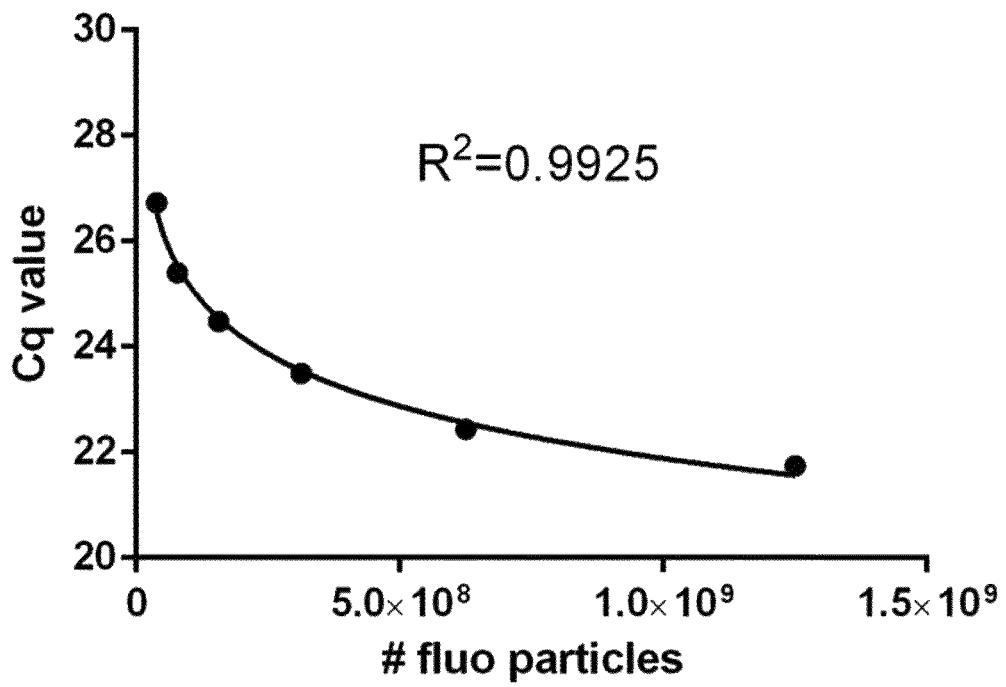

Identification of rEV by fluorescent NTA (fNTA), making use of a 488 nm laser and a 500 nm long pass filter, measured on average 79% fluorescent particles. No differences were observed in the size distribution of rEV measured with conventional NTA (measured by means of light scattering) and fNTA (FIG. 5a). Alternatively, rEV can be assessed by high resolution flow cytometry (FC) (FIG. 5b). FC and fNTA detected similar relative amounts of three biological replicates of rEV. rEV was measured in triplicate in a 2/3 dilution series in PBS with a fluorescence plate reader. A linear signal trend was obtained from $10^{10}$ to $2 \times 10^8$ particles, with a mean $R^2$ of 0.969 for three biological replicates (FIG. 5d). Western blot for EGFP on a series of ½ dilutions of rEV in PBS identified a lower detection limit of $7.8 \times 10^7$ particles, with a narrow linear range from $10^9$ to $4 \times 10^8$ particles (FIG. 5c). With a commercial ELISA kit for P24, a subunit of the Gag polyprotein, the concentration P24 (ng/mL) could be correlated to the amount of particles (as quantified by fNTA). This technique was found to be the most sensitive with a linear concentration range from $10^7$ to $10^6$ particles suspended in PBS in a ½ dilution series in triplicate with a mean $R^2$ of 0.978 for three biological replicates (FIG. 5e). RFU signals and P24 concentrations obtained with a fluorescence plate reader and an anti-P24 ELISA, respectively, differed between different batches of rEV. When measuring the concentration of EGFP mRNA from a ½ dilution series in PBS, a semi-logarithmic relationship was found between the amount of particles and the Cq values for EGFP Q-PCR ($R2=0.9925$) in a broad range from $2\times10^9$ to $4\times10^7$ rEV particles (FIG. 5f).

Example 3: Identification of Optimized Storage Conditions of rEV

The stability of rEV in different conditions was assessed.

Figure 6A:
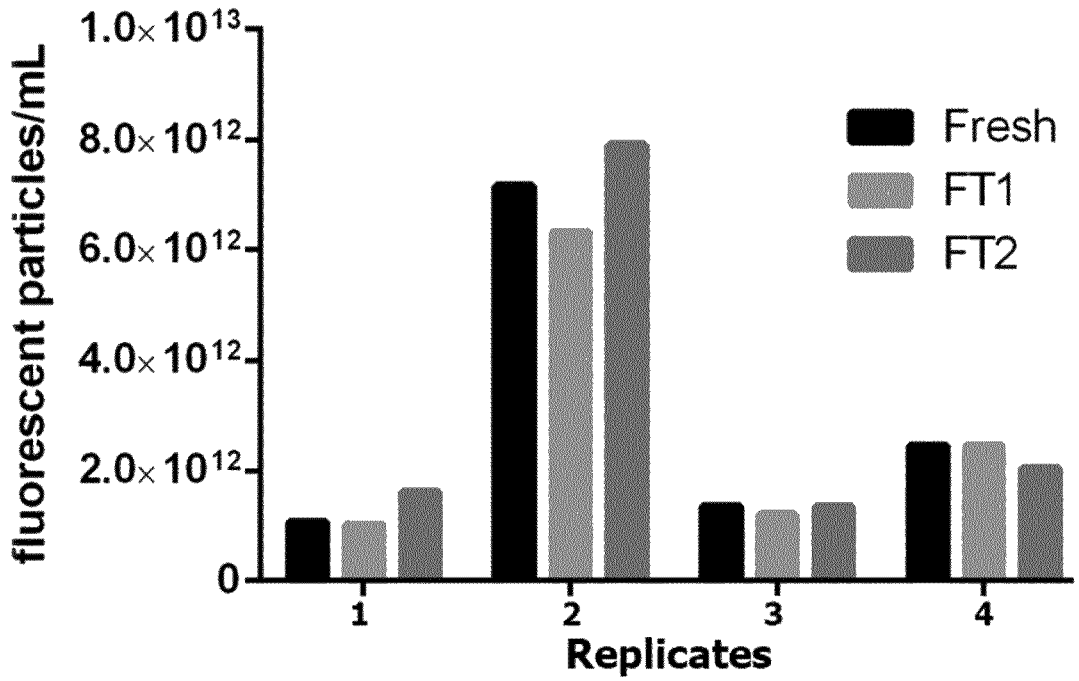
FIGS. 6a-6f: Stability of rEV.
Figure 6B:
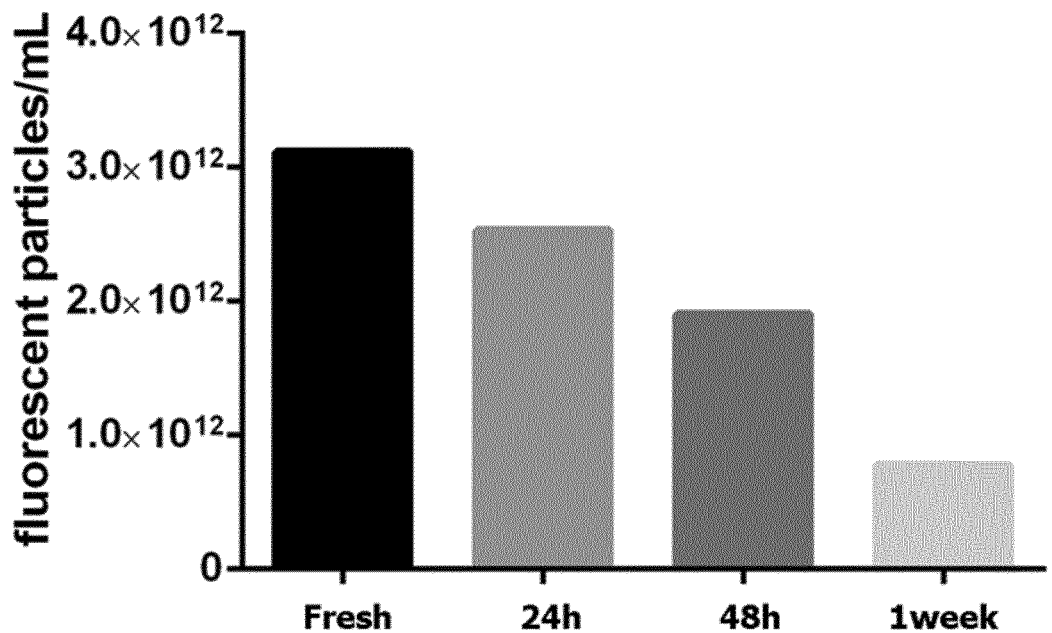
Figure 6C:
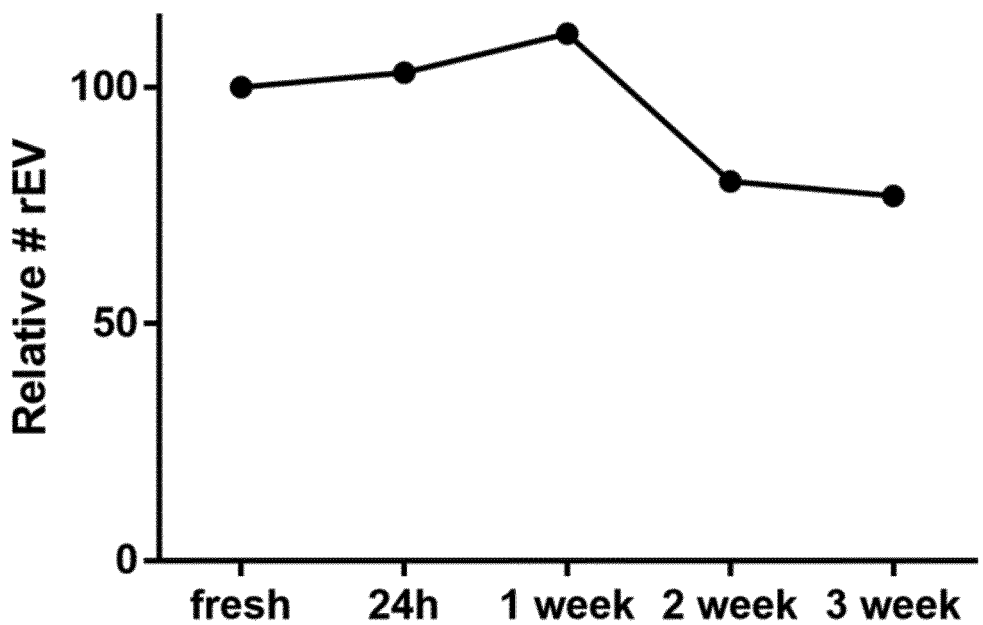
Figure 6D:
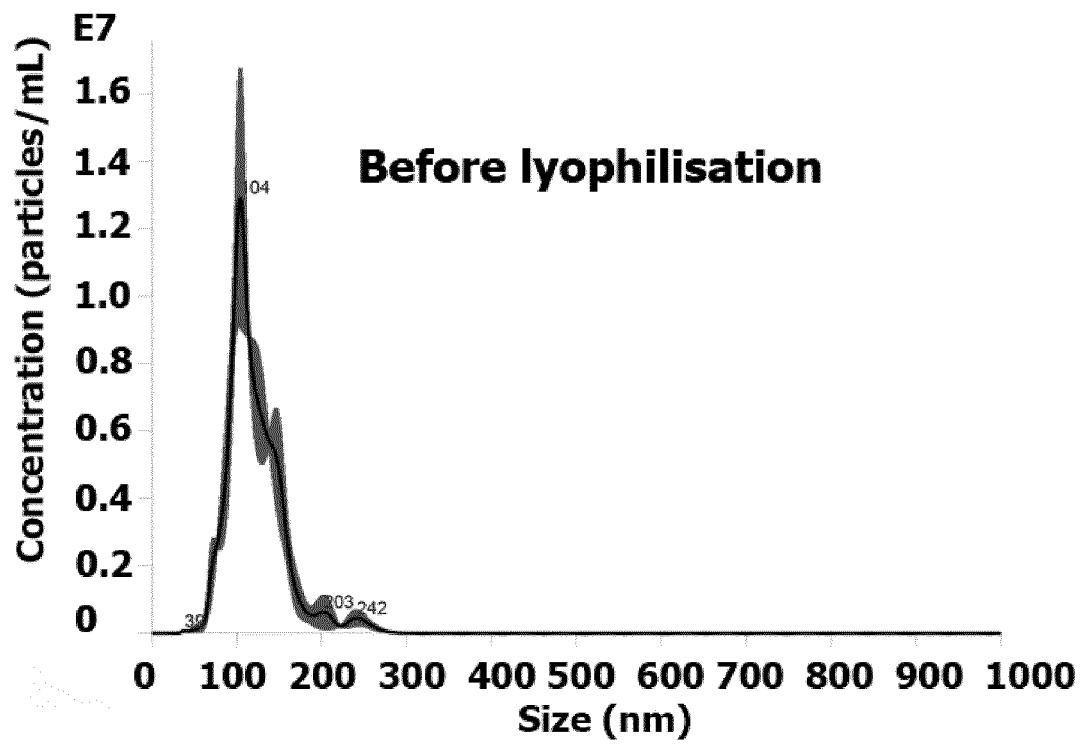
Figure 6D:
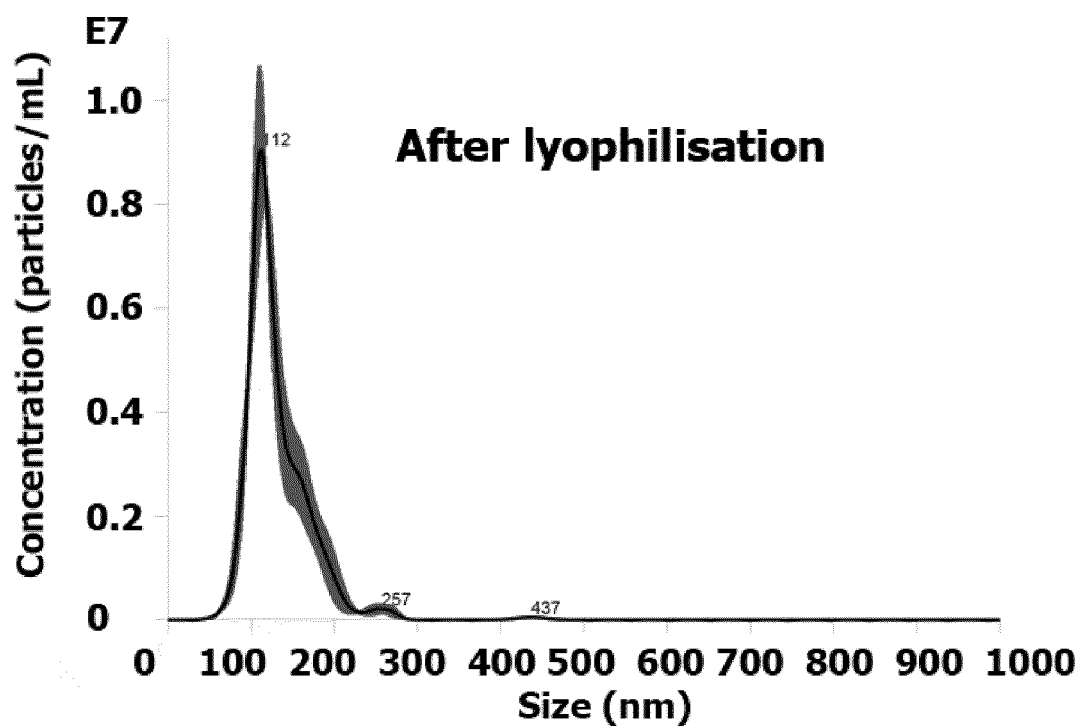

After two consecutive freeze thaw cycles at $-80°$ C., no significant changes in concentration and size distribution were observed in comparison with freshly isolated rEV (FIG. 6a). Diluted storage at $4°$ C. resulted in 18.85% reduction in concentration after 24 hours and 72.56% after one week (FIG. 6b), whereas storage at $4°$ C. of rEV at a higher concentration was stable up to one week (FIG. 6c). rEV lyophilized in PBS supplemented with 5% trehalose did not show any changes in size distribution and concentration (FIG. 6d).

Figure 6E:
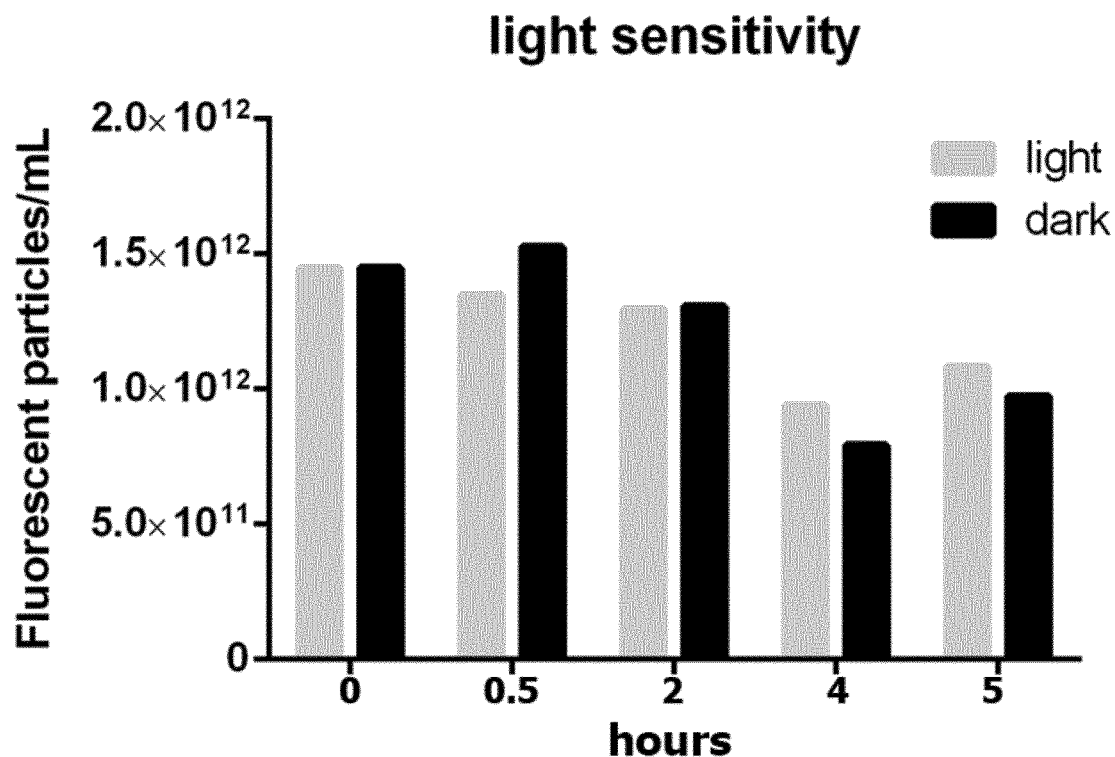

The effect of light exposure to rEV was analyzed by fNTA at different time points of the same batch of rEV incubated at $4°$ C. in a clear versus a black, light omitted, microcentrifuge tube. No differences in concentration were detected in light-exposed or omitted rEV. After 5 hours, the concentration reduced in both clear and black tubes as a result of the instability of diluted rEV at $4°$ C. (FIG. 6e).

Figure 6F:
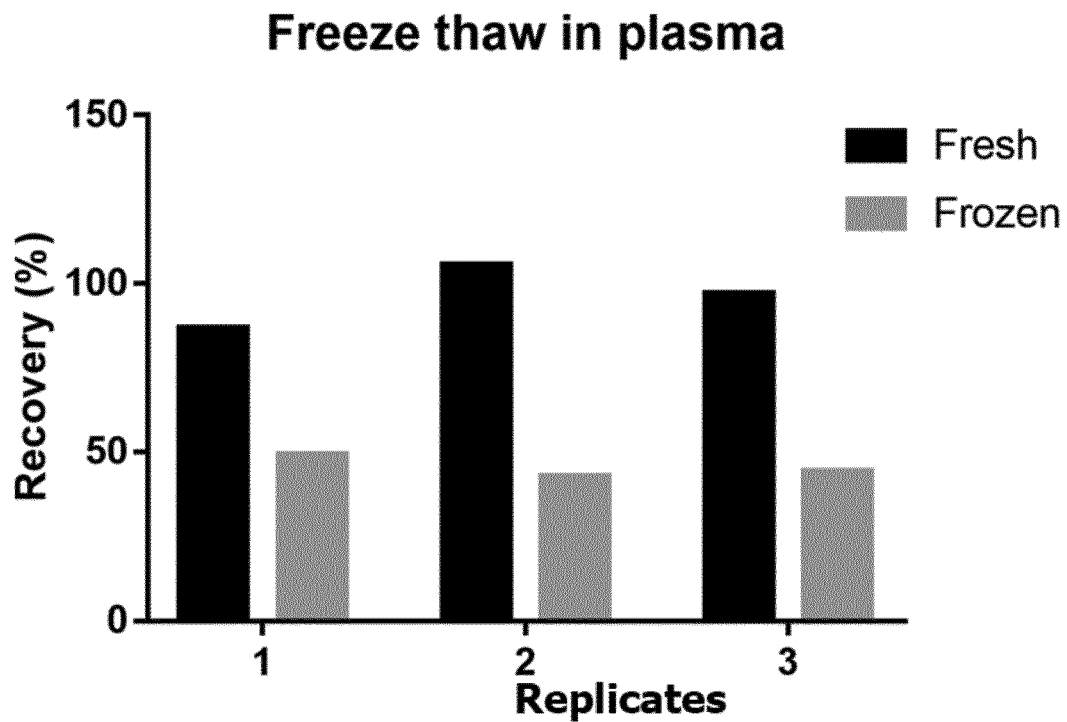

To check the stability of rEV in plasma, spiked plasma samples were stored for 1 week at $-80°$ C. The recovery of rEV after size exclusion chromatography (SEC) was compared with freshly spiked plasma. Recovery was 50% less efficient from frozen plasma compared to fresh plasma (FIG. 6f).

Example 4: The Use of rEV to Estimate the Efficiency of EV Isolation Methods

PBS or healthy donor plasma was spiked with rEV and performed SEC, differential ultracentrifugation (dUC), Exoquick precipitation and ODG. The recovery of rEV, and thus the efficiency of the isolation method, was evaluated by Western blot for EGFP and quantified by fNTA and anti-P24 ELISA.

Figure 7A:
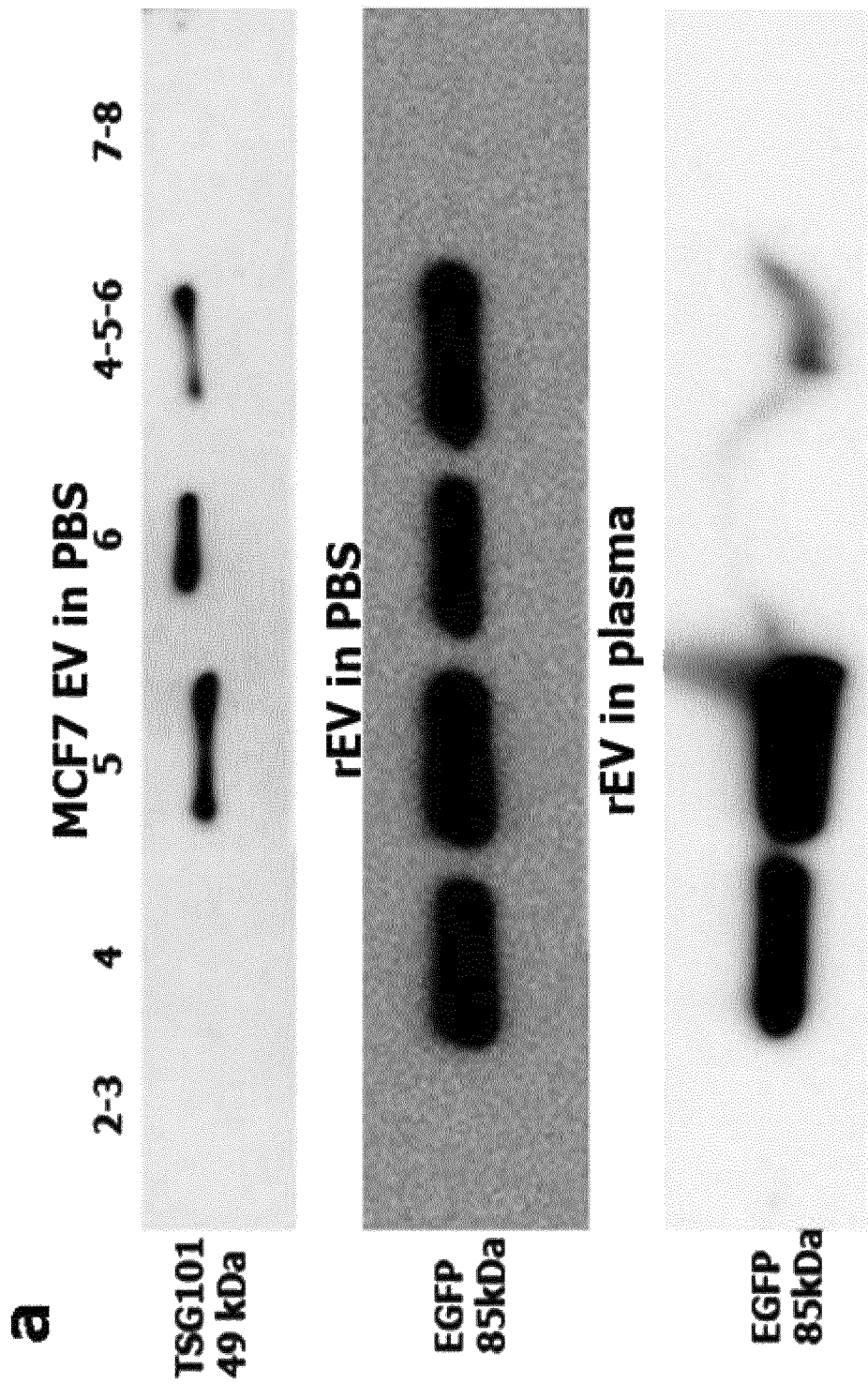
FIGS. 7a-7g: The implementation of rEV to estimate the isolation efficiency of frequently used isolation methods.
Figure 7B:
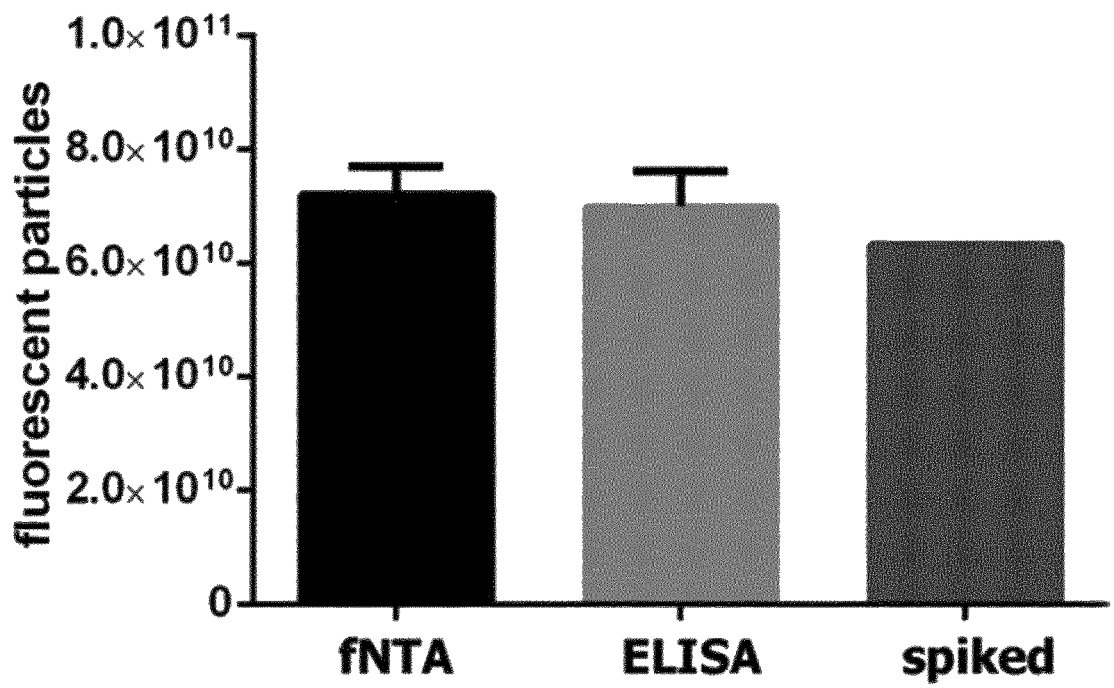

Western blot analysis for EGFP revealed that rEV elutes in similar fractions as sample EV after isolation with SEC (FIG. 7a). When spiked in PBS, rEV elutes in fractions 4 to 6, which corresponds to the TSG101 signal of EV from MCF7-Rab27b cells (FIG. 7a). rEV spiked in plasma elutes in the same fractions as plasma sample EV (FIG. 7a). The EGFP signal in fraction 6 was masked by the co-elution of abundant plasma proteins (albumin). Quantification of R-EV by fNTA and anti-P24 ELISA revealed an isolation efficiency of nearly 100% (FIG. 7b).

Figure 8A:
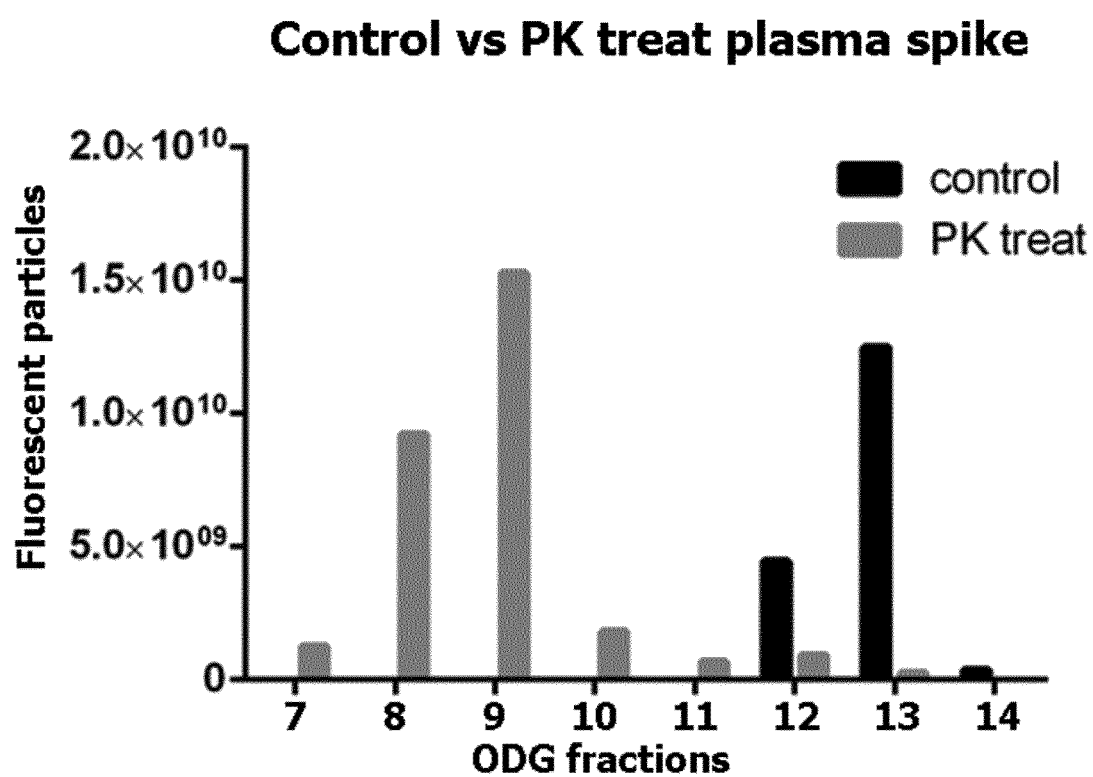
FIGS. 8a-8h: rEV shifts to higher densities in plasma and in the presence of exogenously administered IgM and IgG.
Figure 8B:
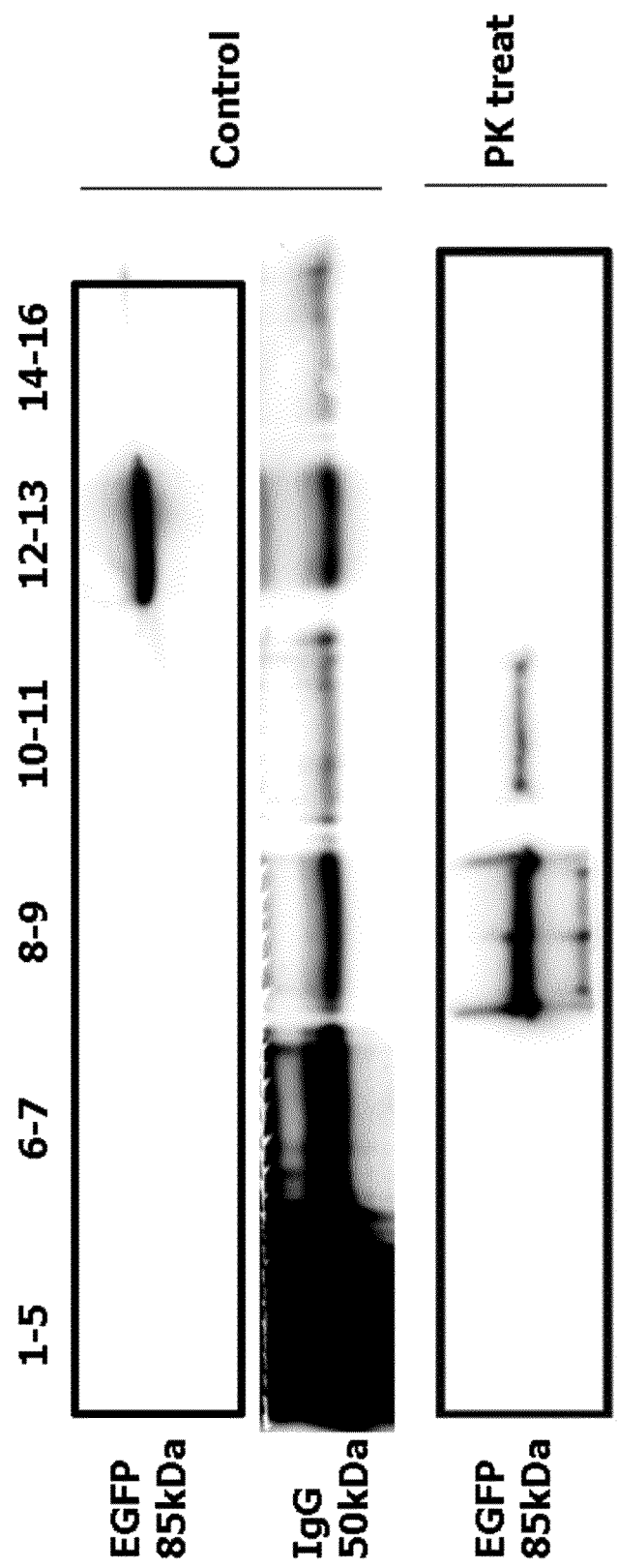
Figure 8C:
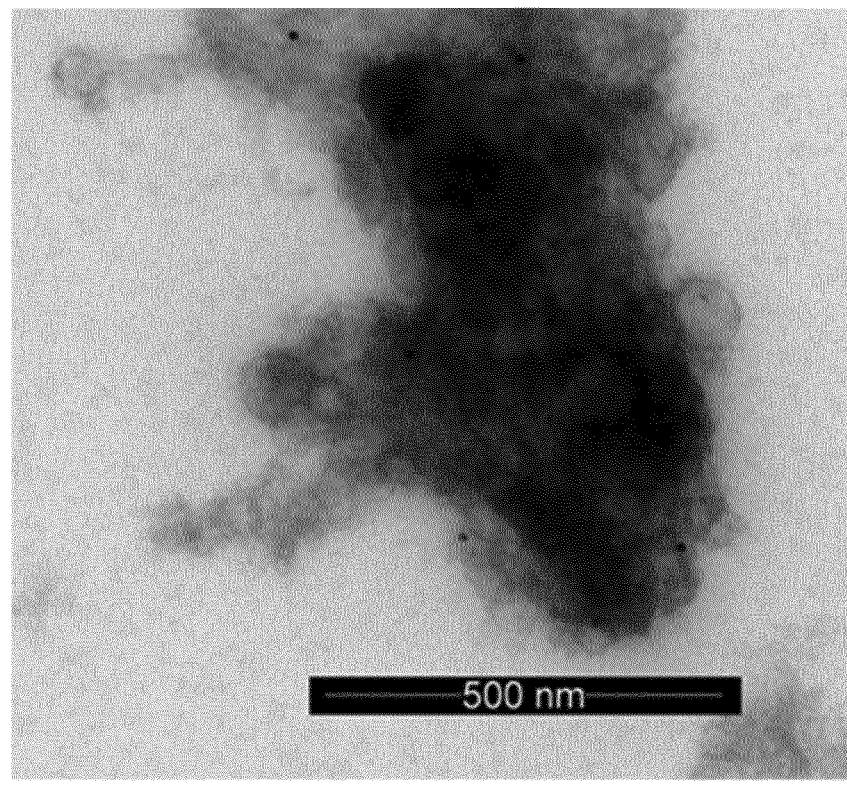
Figure 8D:
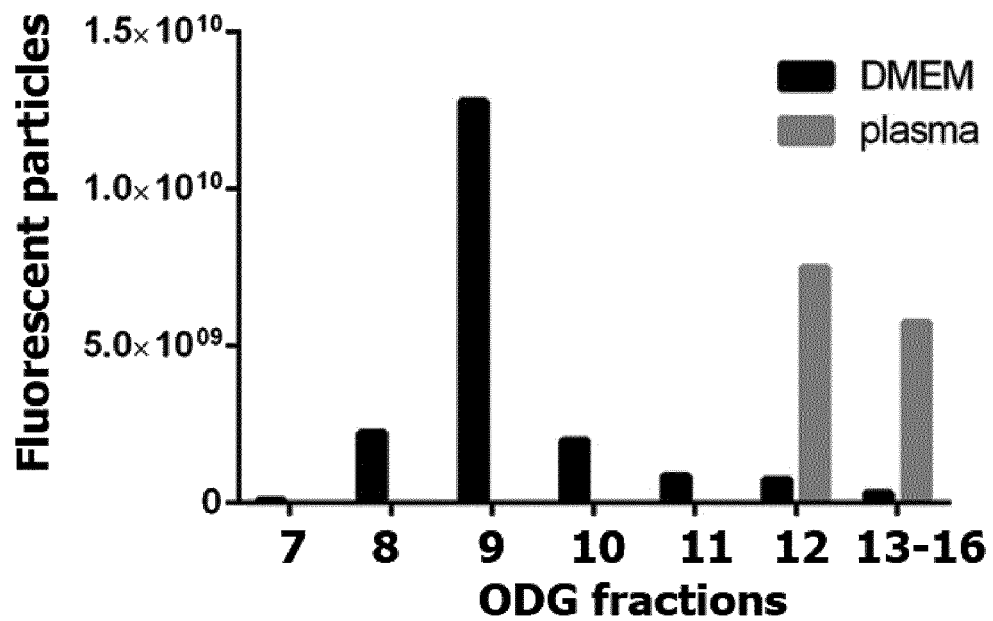
Figure 8E:
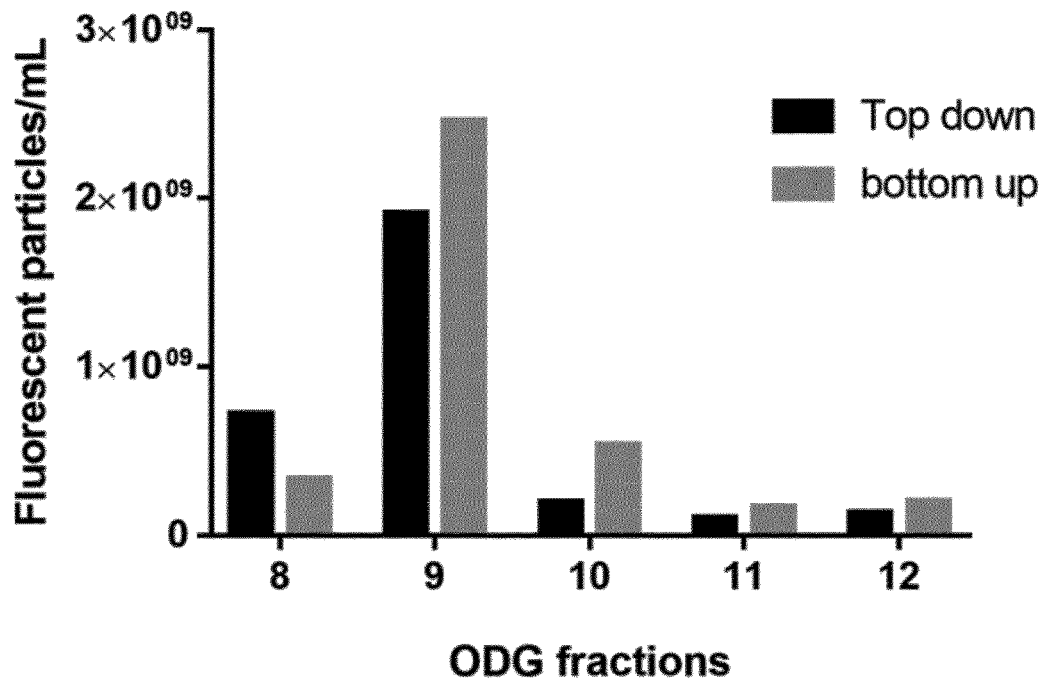
Figure 8F:
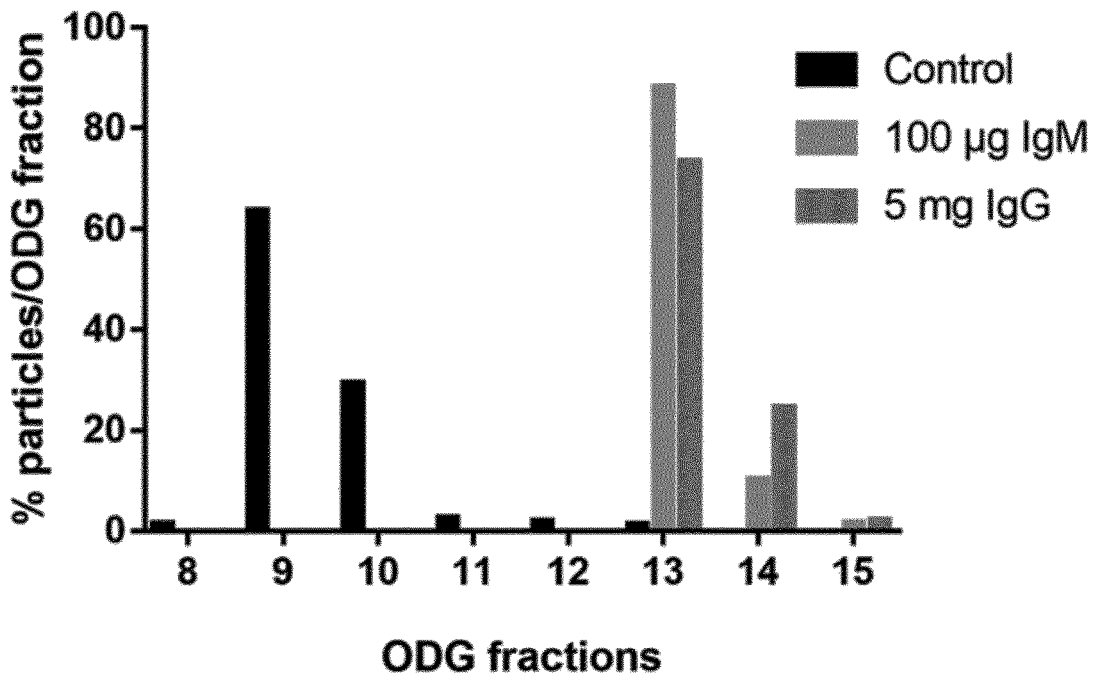

Next, SEC fractions 4 to 6 from plasma spiked with rEV were concentrated to 1 mL and loaded on top of a discontinuous iodixanol gradient. After 18 hours centrifugation at 100,000 g, all top to bottom fractions were collected. Western blot analysis and fNTA measurements revealed that rEV was localized in higher density fractions 12-13 (1.14-1.18 g/mL), in contrast to plasma sample EV, localized in fractions 8-9 (FIGS. 8a, 8b). Electron microscopy and Western blot analysis identified rEV aggregation and interaction with plasma proteins including immunoglobulins (IgG) (FIGS. 8b, 8c). Quantification with fNTA revealed an isolation efficiency of only 27.5% in ODG fractions 12-13 (data not shown). Aggregation of rEV only seemed to occur when spiked in plasma, since 40% of rEV particles were retrieved after ODG centrifugation when spiked in DMEM culture medium supplemented with 10% FBS (FIG. 8d). When performing a bottom-up or top-down ODG on urine spiked with rEV all rEV particles could be found in the endogenous EV enriched density fractions (FIG. 8e). This shift in density could also be mimicked by incubation of the rEV particles with 100 μg IgM or 5 mg IgG isolated from healthy human serum prior to spike in PBS and isolation via ODG (FIG. 8f).

Figure 7C:
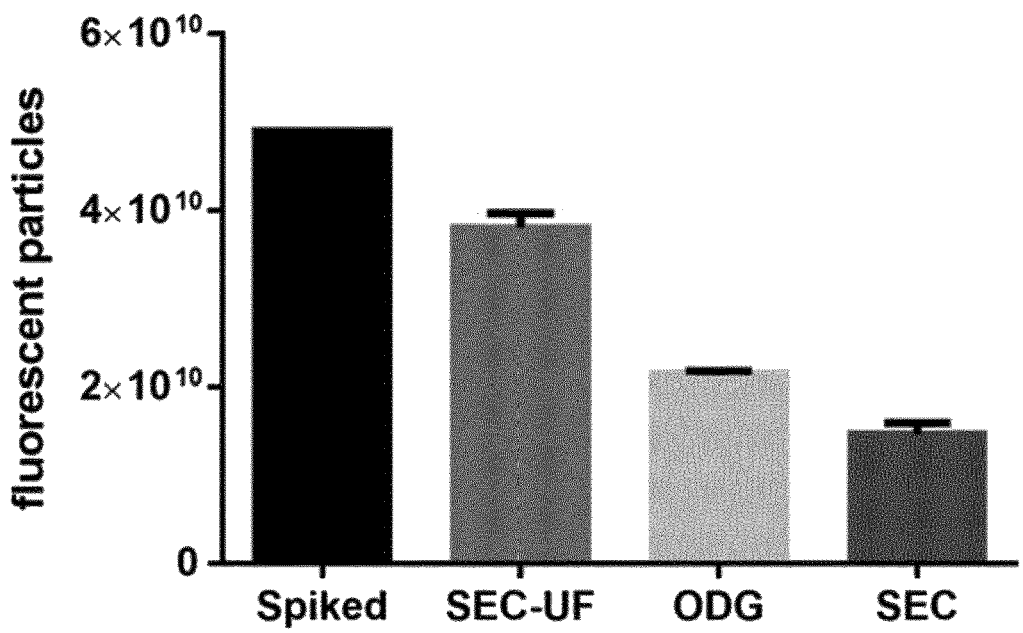
Figure 7D:
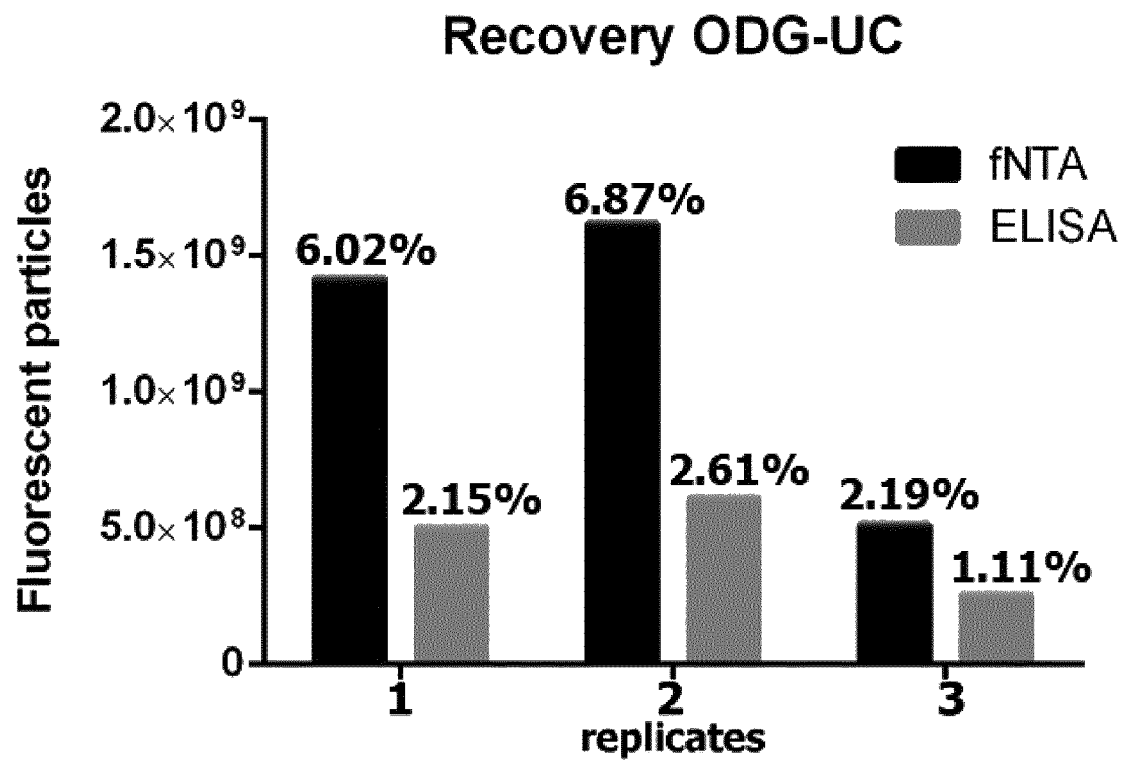
Figure 7E:
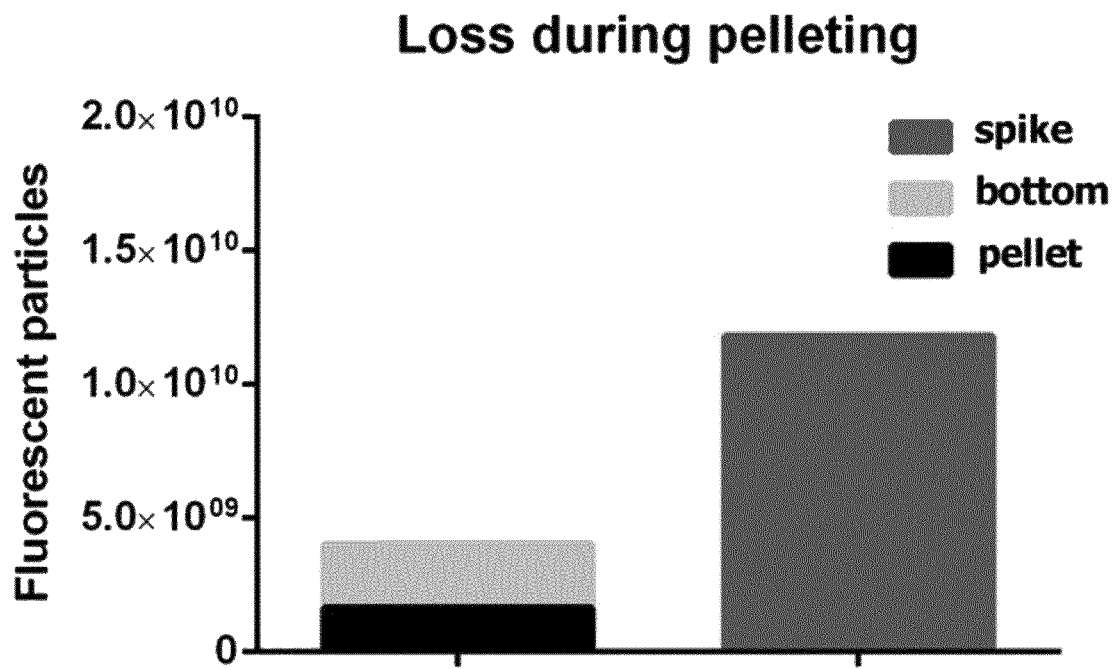
Figure 7F:
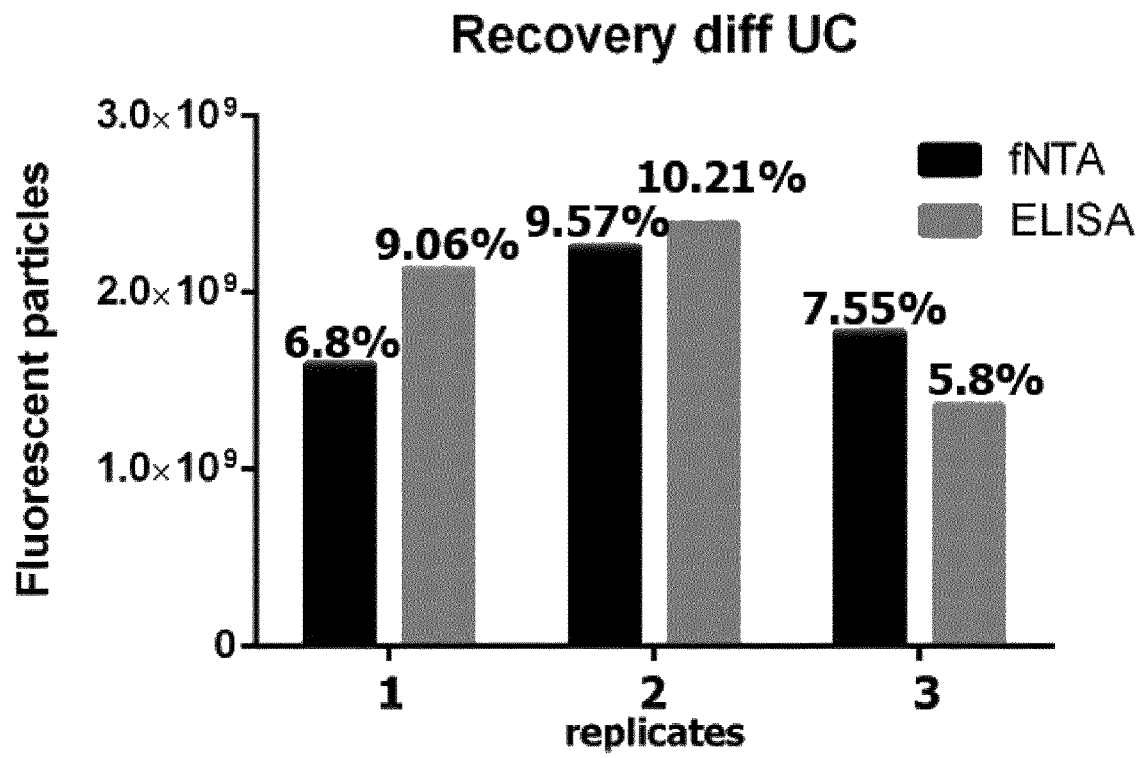
Figure 8G:
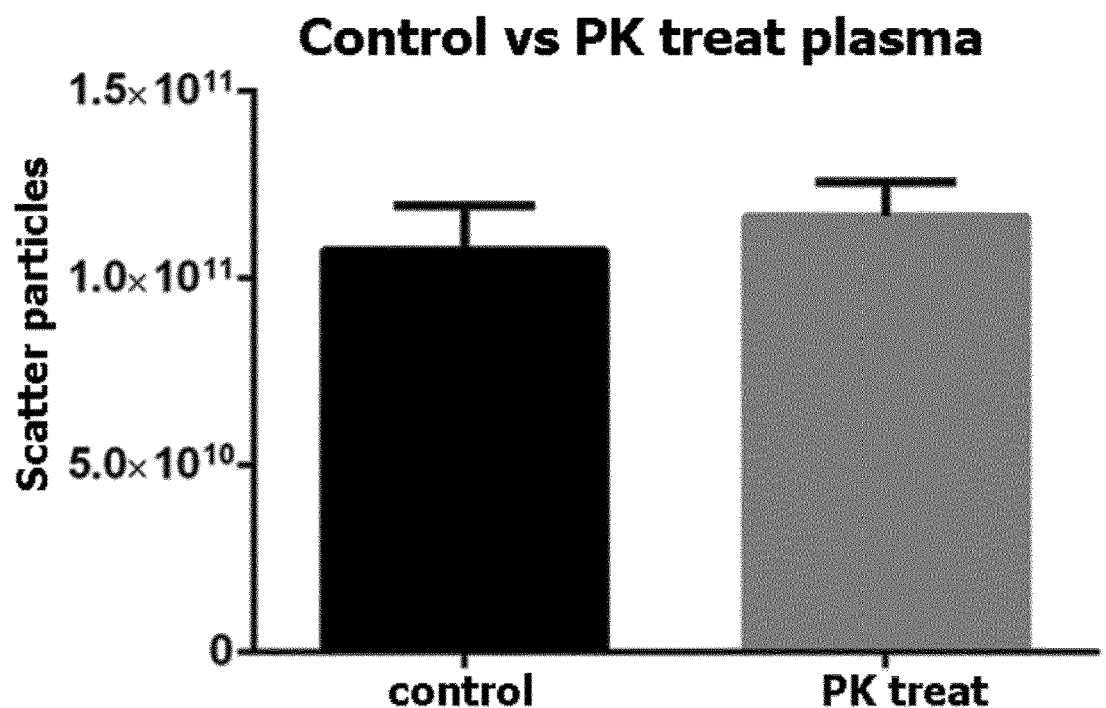
Figure 8H:
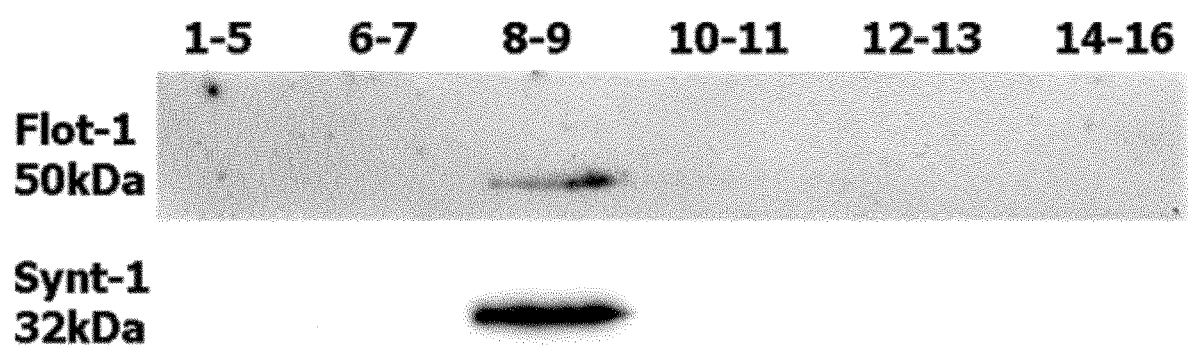
Figure 9A:
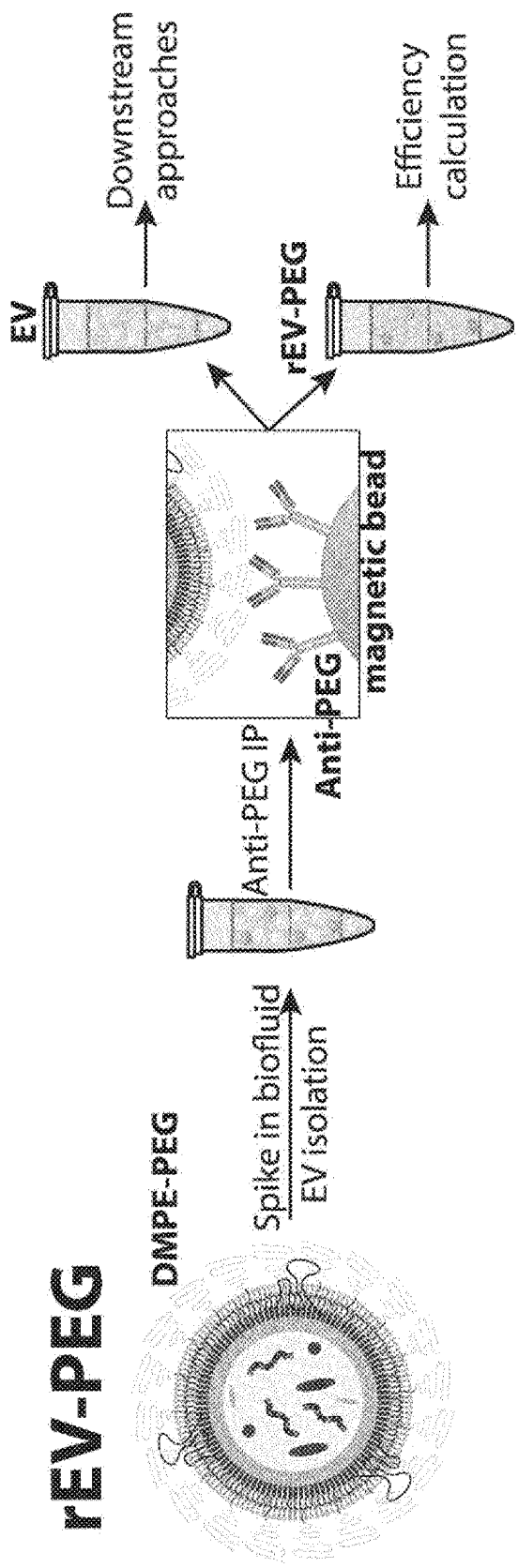
FIGS. 9a-9e: rEV modification and implementation in applications for normalization.
Figure 9B:
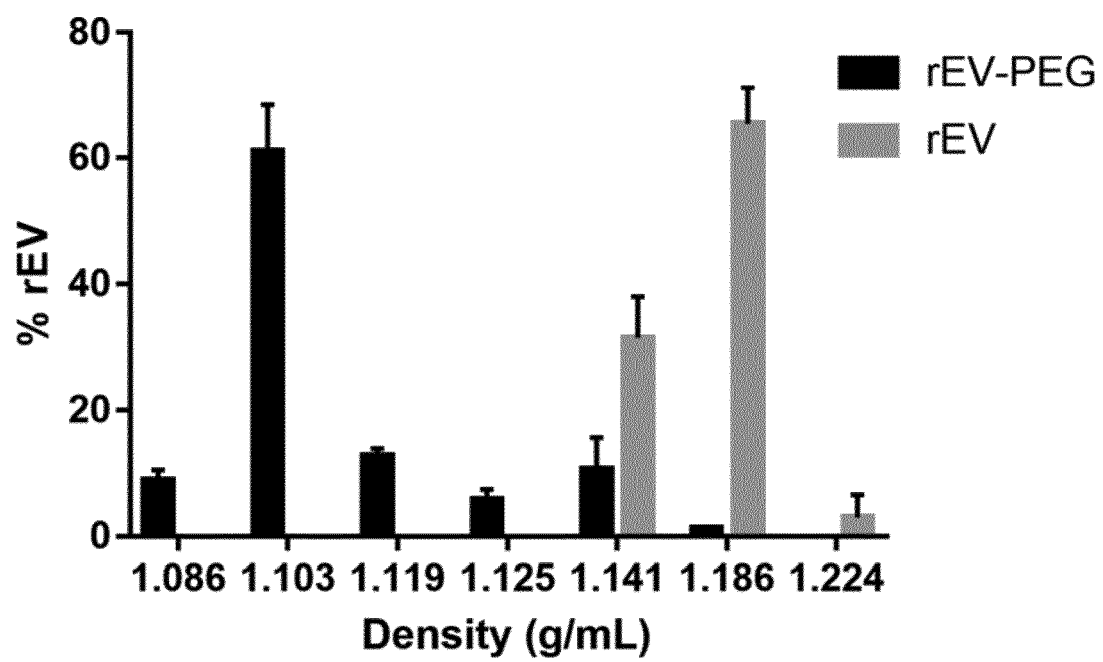
Figure 9C:
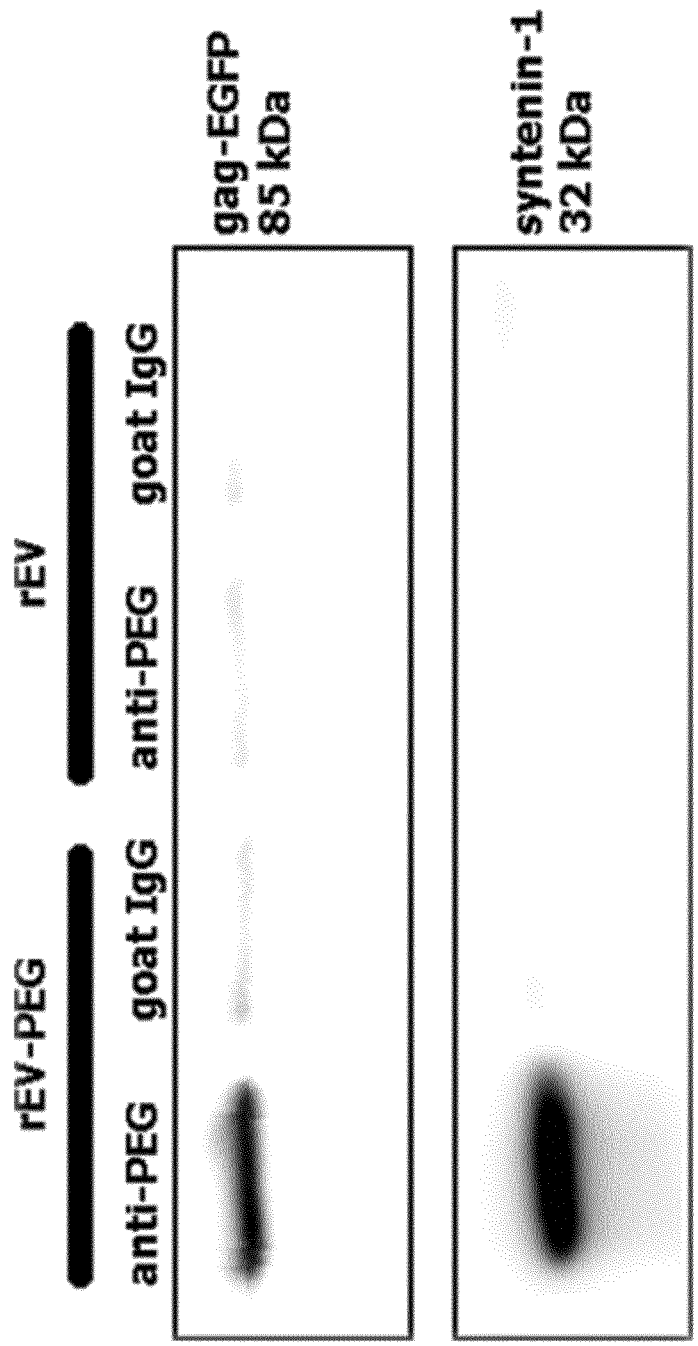

Alternatively, a proteinase K (PK) treatment was performed (1 mg/mL for 1 hour at $37°$ C.) on the concentrated SEC fractions of the spiked plasma prior to ODG centrifugation. PK treatment shifted rEV from density fractions 12-13 to 8-9 (FIG. 8a). To remove iodixanol remnants, ODG fractions 8 and 9 were pooled and subjected to SEC. Fractions 4 to 7 were collected and quantified by fNTA. This revealed an isolation efficiency of 30% (FIG. 7c). PK treatment did not influence the isolation of plasma sample EV since the amount of particles was similar for untreated plasma and the EV markers syntenin-1 and flotillin-1 were still detected by Western blot analysis after isolation by SEC-ODG (FIGS. 8g, 8h). Although this density shift is a unique feature to separate rEV from EV, it is not tailor-made for other EV isolation methods and it may be incompatible with certain downstream applications. Therefore, rEV was modified by post-insertion PEGylation to avoid plasma protein interactions while providing the unique opportunity for proteinase-independent separation of spiked rEV from EV in any biofluid (FIG. 9a). Surface masking of rEV by DMPE-PEG (1,2-dimyristoyl-sn-glycero-3-phosphoethanolamine conjugated to polyethylene glycol) does not alter fluorescence intensity and size distribution, but prevents the interaction with plasma proteins (FIG. 9b). More than 85% of rEV-PEG spiked in plasma floats at similar densities as EV (1.086-1.119 g/mL). Immune precipitation using anti-PEG-coated magnetic beads specifically captures rEV-PEG compared to rEV (FIG. 9c).

rEV could also be isolated when spiked in DMEM culture medium supplemented with 10% FBS after ODG centrifugation followed by high speed pelleting (100,000 g for 3 hours), but this with very low efficiency (2 to 7% of the initially spiked amount was retrieved) (FIG. 7d). Since ODG centrifugation had a recovery of 40% (fNTA on pure ODG fractions 8-9), it was hypothesized that high speed pelleting of EV could be responsible for such a great loss. This was tested by flushing the bottom of a UC tube with 1 mL of PBS after resuspension of the pellet in 100 μL PBS until no fluorescent signal could be detected by fNTA and observed that more EV stuck to the bottom of the tube than could be resuspended in low volumes of PBS (100 μL) (FIG. 7e). To check whether the adherence to the bottom and probably also to the wall of the tube was not an artefact of rEV itself, these experimental conditions were repeated with EV isolated from MCF7-Rab27b cells spiked in PBS and concluded similar observations as with rEV. dUC on plasma spiked with rEV recovered around 10% rEV as measured with fNTA and ELISA (FIG. 7f). This low recovery was probably caused by the bottom/wall adherence as described above.

Figure 7G:
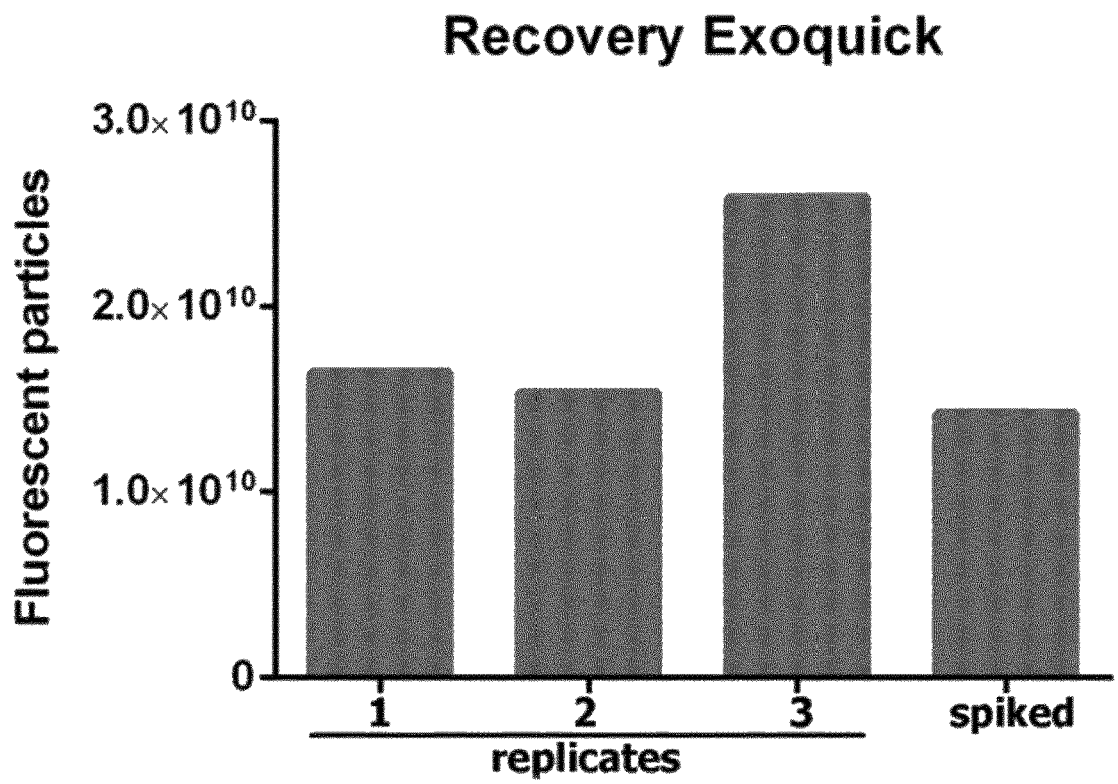

Exoquick precipitation of plasma spiked with rEV resulted in 100% efficiency of EV isolation as measured by anti-p24 ELISA (FIG. 7g).

Figure 9D:
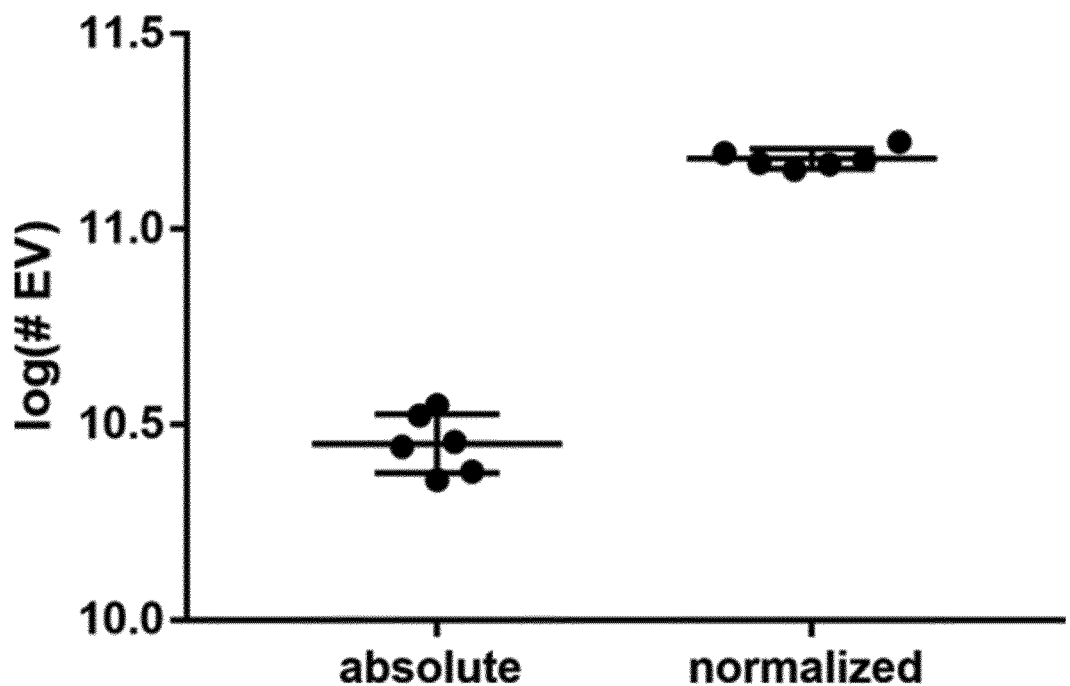
Figure 9E:
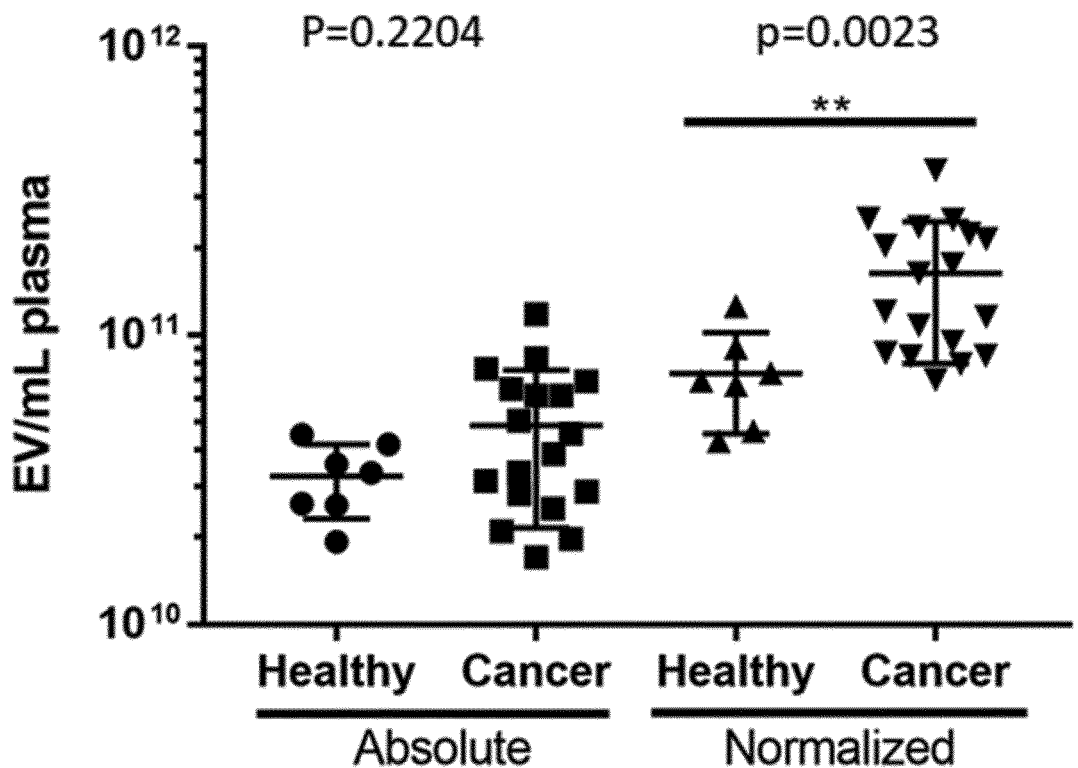

Example 5: rEV Allows for an Accurate Comparison of EV Numbers in Plasma from Cancer Patients Versus Healthy Individuals To demonstrate the applicability of rEV to define and mitigate for inter-user variations, rEV are spiked in plasma and isolated by SEC-ODG-SEC (n=6). The total number of EV and rEV are quantified by NTA and fNTA, respectively. The inter-user variation, expressed as the coefficient of variation (CV), is reduced by 66% (from 17.5% to 6.1%) by normalization according to rEV isolation efficiencies (FIG. 9d). In a proof of concept experiment, $5\times10^{10}$ fluorescent rEV particles were spiked in 2 mL plasma from breast cancer patients (n=18) and age-matched healthy volunteers (n=6). EV and rEV were next isolated from the PK-treated spiked plasma samples through a combination of SEC-ODG-SEC and quantified the total amount of isolated vesicles and the fluorescent rEV via NTA and fNTA, respectively. From the latter quantification, the recovery of each EV isolation is calculated and the total amount of vesicles is normalized based on this recovery. EV concentrations per mL plasma normalized according to rEV isolation efficiencies are increased by 2.2 fold (p=0.0023, Mann-Whitney test) in breast cancer patients compared to healthy individuals. This fold change is of higher significance after normalization compared to the absolute values (p=0.0023 vs p=0.2204, Mann-Whitney test) (FIG. 9e).

Example 6: Implementing the PSI Sequence to Load EGFP mRNA in rEV

The presence of EGFP mRNA in rEV was observed. Since no packaging signal is introduced during transfection, EGFP mRNA is presumably non-specifically sorted in rEV. The pMET7-GAG-EGFP plasmid, used for rEV production, was modified by fusing HIV-1 gRNA packaging (PSI)-signal to the GAG-EGFP fusion gene.[38] fNTA confirmed loading of PSI-fused GFP mRNA in rEV. Using this RNA packaging signal PSI, it is possible to sort any exogenous or synthetic RNA inside rEV.

REFERENCES

1. Crowley E., F. Di Nicolantonio, F. Loupakis, and A. Bardelli. Liquid biopsy: monitoring cancer-genetics in the blood. *Nat. Rev. Clin. Oncol.* 10, 472-484 (2013).
2. Brock G., E. Castellanos-Rizaldos, L. Hu, C. Coticchia, and J. Skog. Liquid biopsy for cancer screening, patient stratification and monitoring. Transl. *Cancer Res.* 4, 280-290 (2015).
3. Kalluri R. The biology and function of fibroblasts in cancer. *Nat. Rev. Cancer* 16, 582-598 (2016).
4. Kalra H., G. P. C. Drummen, and S. Mathivanan. Focus on extracellular vesicles:
Introducing the next small big thing. *Int. J. Mol. Sci.* 17, (2016).
5. Tkach M. and C. Théry. Communication by Extracellular Vesicles: Where We Are and Where We Need to Go. *Cell* 164, 1226-1232 (2016).
6. Hoshino A. et al. Tumour exosome integrins determine organotropic metastasis. *Nature* 1-19 (2015). doi: 10.1038/nature15756
7. Sadovska L., J. Eglītis, and A. Linē. Extracellular Vesicles as Biomarkers and Therapeutic Targets in Breast Cancer. *Anticancer Res.* 35, 6379-90 (2015).
8. Nawaz M. et al. The emerging role of extracellular vesicles as biomarkers for urogenital cancers. *Nat. Rev. Urol.* 11, 688-701 (2014).
9. Tang M. K. S. and A. S. T. Wong. Exosomes: Emerging biomarkers and targets for ovarian cancer. *Cancer Lett.* 367, 26-33 (2015).
10. Melo S. A. et al. Glypican-1 identifies cancer exosomes and detects early pancreatic cancer. *Nature* 523, 177-182 (2015).
11. Lötvall J. et al. Minimal experimental requirements for definition of extracellular vesicles and their functions: A position statement from the International Society for Extracellular Vesicles. *J. Extracell. Vesicles* 3, 1-6 (2014).
12. Witwer K. W. et al. Standardization of sample collection, isolation and analysis methods in extracellular vesicle research. *J. Extracell. Vesicles* 2 (2013).
13. Van Deun J. et al. EV-TRACK: transparent reporting and centralizing knowledge in extracellular vesicle research. *Nat. Methods* 14, 228-232 (2017).
14. Van Der Pol E., F. A. W. Coumans, A. Sturk, R. Nieuwland, and T. G. Van Leeuwen. Refractive index determination of nanoparticles in suspension using nanoparticle tracking analysis. *Nano Lett.* 14, 6195-6201 (2014).
15. Gardiner C., Y. J. Ferreira, R. A. Dragovic, C. W. G. Redman, and I. L. Sargent. Extracellular vesicle sizing and enumeration by nanoparticle tracking analysis. *Journal of Extracellular Vesicles* 2, (2013).
16. Valkonen S. et al. Biological reference materials for extracellular vesicle studies. *Eur. Pharm. Sci.* 98, 4-16 (2017).
17. Zhang L. et al. Microenvironment-induced PTEN loss by exosomal microRNA primes brain metastasis outgrowth. *Nature* (2015). doi:10.1038/nature15376
18. Saad J. S. et al. Structural basis for targeting HIV-1 Gag proteins to the plasma membrane for virus assembly. *Proc. Natl. Acad. Sci. U.S.A* 103, 11364-9 (2006).
19. Bieniasz P. D. Late budding domains and host proteins in enveloped virus release. *Virology* 344, 55-63 (2006).
20. Coffin J. M., S. H. Hughes, V. H. *Retroviruses.* (Cold Spring Harbor Laboratory Press, 1997).
21. Lamb R. A. and R. M. Krug. Orthomyxoviridae: The viruses and their replication. (1996).
22. Nabhan J. F., R. Hu, R. S. Oh, S. N. Cohen, and Q. Lu. Formation and release of arrestin domain-containing protein 1-mediated microvesicles (ARMMs) at plasma membrane by recruitment of TSG101 protein. *Proc. Natl. Acad. Sci. U.S.A* 109, 4146-51 (2012).
23. Harty R. N., M. E. Brown, G. Wang, J. Huibregtse, and F. P. Hayes. A PPxY motif within the VP40 protein of Ebola virus interacts physically and functionally with a ubiquitin ligase: implications for filovirus budding. *Proc. Natl. Acad. Sci. U.S.A* 97, 13871-6 (2000).
24. Pastuzyn E. D. et al. The Neuronal Gene Arc Encodes a Repurposed Retrotransposon Gag Protein that Mediates Intercellular RNA Transfer. *Cell* 172, 275-288.e18 (2018).
25. Justice P. A. et al. Membrane vesiculation function and exocytosis of wild-type and mutant matrix proteins of vesicular stomatitis virus. *J. Virol.* 69, 3156-60 (1995).
26. Van Deun J. et al. The Impact of Disparate Isolation Methods for Extracellular Vesicles on Downstream RNA Profiling. *J. Extracell. vesicles* (2014).
27. Petersen K. E. et al. A review of exosome separation techniques and characterization of B16-F10 mouse melanoma exosomes with AF4-UV-MALS-DLS-TEM. *Anal. Bioanal. Chem.* 406, 7855-66 (2014).
28. Lee K., H. Shao, R. Weissleder, and H. Lee. Acoustic purification of extracellular microvesicles. *ACS Nano* 9, 2321-7 (2015).
29. Nakai W. et al. A novel affinity-based method for the isolation of highly purified extracellular vesicles. *Sci. Rep.* 6, 33935 (2016).

30. Théry C., A. Clayton, S. Amigorena, and G. Raposo, G. Isolation and characterization of exosomes from cell culture supernatants. *Curr. Protoc. Cell Biol.* 3.22.1-3.22.29 (2006).
31. van der Vlist E. J., E. N. M. Nolte-'t Hoen, W. Stoorvogel, G. J. A. Arkesteijn, and M. H. M. Wauben. Fluorescent labeling of nano-sized vesicles released by cells and subsequent quantitative and qualitative analysis by high-resolution flow cytometry. *Nat. Protoc.* 7, 1311-26 (2012).
32. Grönwall C., J. Vas, and G. J. Silverman. Protective roles of natural IgM antibodies. *Frontiers in Immunology* 3, 66 (2012).
33. Blanc L., C. Barres, P. Bette-Bobillo, and M. Vidal. Reticulocyte-secreted exosomes bind natural IgM antibodies: Involvement of a ROS-activatable endosomal phospholipase iPLA2. *Blood* 110, 3407-3416 (2007).
34. Eyckerman S. et al. Trapping mammalian protein complexes in viral particles. *Nat. Commun.* 7, 11416 (2016).
35. Vergauwen G. et al. Confounding factors of ultrafiltration and protein analysis in extracellular vesicle research. *Sci. Rep.* 7, 2704 (2017).
36. Hogue I. B., J. R. Grover, F. Soheilian, K. Nagashima, and A. Ono. Gag induces the coalescence of clustered lipid rafts and tetraspanin-enriched microdomains at HIV-1 assembly sites on the plasma membrane. *J. Virol.* 85, 9749-66 (2011).
37. Jouvenet N. et al. Plasma membrane is the site of productive HIV-1 particle assembly. *PLoS Biol.* 4, e435 (2006).
38. Comas-Garcia M. et al. Efficient support of virus-like particle assembly by the HIV-1 packaging signal. *Elife* 7, (2018).

The invention claimed is:
1. A method of determining recovery rate of sample extracellular vesicles, the method comprising:
mixing a biofluid sample comprising sample extracellular vesicles with a known amount of recombinant extracellular vesicles, wherein the recombinant extracellular vesicles comprise:
a) a self-assembling protein that directs its own release through vesicles as a luminal membrane-bound protein, wherein the self-assembling protein comprises
i) a membrane insertion domain that directly inserts in a double lipid layer or that recruits a lipid chain for insertion into a double lipid layer,
ii) a self-assembling domain responsible for oligomerization, and
iii) a late budding protein domain, and
b) a heterologous marker,
to obtain a mixture,
isolating the extracellular vesicles from the mixture,
detecting an amount of the recombinant extracellular vesicles among the isolated extracellular vesicles, and
determining the recovery rate of the sample extracellular vesicles based on a ratio of the amount of recombinant extracellular vesicles after isolation to the known amount of recombinant extracellular vesicles mixed with the biofluid sample before isolation.

2. The method according to claim 1, wherein the heterologous marker is a heterologous nucleic acid molecule or a heterologous protein.

3. The method according to claim 2, wherein the heterologous marker is a heterologous protein fused to the self-assembling protein.

4. A method of determining recovery rate of sample extracellular vesicles, the method comprising:
mixing a biofluid sample comprising sample extracellular vesicles with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
isolating the extracellular vesicles from the mixture,
detecting an amount of the recombinant extracellular vesicles among the isolated extracellular vesicles, and
determining the recovery rate of the sample extracellular vesicles based on a ratio of the amount of recombinant extracellular vesicles after isolation to the known amount of recombinant extracellular vesicles mixed with the biofluid sample before isolation;
wherein the heterologous marker is a heterologous nucleic acid fused to retroviral packaging signal psi.

5. A method of determining recovery rate of sample extracellular vesicles, the method comprising:
mixing a biofluid sample comprising sample extracellular vesicles with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
isolating the extracellular vesicles from the mixture,
detecting an amount of the recombinant extracellular vesicles among the isolated extracellular vesicles, and
determining the recovery rate of the sample extracellular vesicles based on a ratio of the amount of recombinant extracellular vesicles after isolation to the known amount of recombinant extracellular vesicles mixed with the biofluid sample before isolation;
wherein the heterologous marker is a heterologous nucleic acid molecule or a heterologous protein and wherein detecting the amount of the recombinant extracellular vesicles is undertaken by determining amount of any heterologous nucleic acid by real-time PCR, RT-qPCR, digital PCR, RNA sequencing, nanostring, branched DNA amplification or serial analysis of gene expression.

6. The method according to claim 2, wherein the heterologous marker is a light-emitting protein.

7. The method according to claim 2, wherein the heterologous marker is light-emitting protein mRNA.

8. A method of determining recovery rate of sample extracellular vesicles, the method comprising:
mixing a biofluid sample comprising sample extracellular vesicles with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
isolating the extracellular vesicles from the mixture,
detecting an amount of the recombinant extracellular vesicles among the isolated extracellular vesicles, and
determining the recovery rate of the sample extracellular vesicles based on a ratio of the amount of recombinant extracellular vesicles after isolation to the known amount of recombinant extracellular vesicles mixed with the biofluid sample before isolation;
wherein the self-assembling protein that directs its own release through vesicles as a luminal membrane-bound protein is selected from the group consisting of: retroviral group-specific antigen, retroviral group-specific antigen variations, influenza M1 protein, ARRDC1 protein, ARC protein, Ebola virus VP40 protein, and M proteins of vesicular stomatitis virus.

9. The method according to claim 1,
wherein isolating the extracellular vesicles from the mixture comprises and/or is combined with a separation step resulting in obtaining a first fraction comprising the recombinant extracellular vesicles and a second fraction comprising the sample extracellular vesicles, and
wherein the detecting of the amount of the recombinant extracellular vesicles occurs in the first fraction.

10. The method according to claim 9, wherein the separation step is a density-based separation step.

11. The method according to claim 9, wherein the biofluid sample is a plasma sample or serum sample.

12. The method according to claim 9,
wherein the mixture is treated with a protease before isolating the extracellular vesicles from the mixture, or
wherein the recombinant extracellular vesicles are incubated with polyethyleneglycol (PEG) so that the recombinant extracellular vesicles and the sample extracellular vesicles are present in the same fraction after the isolation.

13. A method of determining recovery rate of sample extracellular vesicles, the method comprising:
mixing a biofluid sample comprising sample extracellular vesicles with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
isolating the extracellular vesicles from the mixture,
detecting an amount of the recombinant extracellular vesicles among the isolated extracellular vesicles, and
determining the recovery rate of the sample extracellular vesicles based on a ratio of the amount of recombinant extracellular vesicles after isolation to the known amount of recombinant extracellular vesicles mixed with the biofluid sample before isolation;
wherein the recombinant extracellular vesicles are incubated with immunoglobulin proteins IgG and/or IgM before mixing the biofluid sample with a known amount of the recombinant extracellular vesicles so that the recombinant extracellular vesicles and the sample extracellular vesicles are present in a different fraction after the isolation.

14. A method of determining recovery rate of sample extracellular vesicles, the method comprising:
mixing a biofluid sample comprising a plasma sample or serum sample with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
treating the mixture with a protease or incubating the recombinant extracellular vesicle with polyethylene glycol (PEG) so that the recombinant extracellular vesicles and the sample extracellular vesicles are present in the same fraction;
isolating the extracellular vesicles from the mixture comprising and/or combining with a density-based separation step resulting in obtaining a first fraction comprising the recombinant extracellular vesicles and a second fraction comprising the sample extracellular vesicles
detecting an amount of the recombinant extracellular vesicles among the isolated extracellular vesicles of the first fraction, and
determining the recovery rate of the sample extracellular vesicles based on a ratio of the amount of recombinant extracellular vesicles after isolation to the known amount of recombinant extracellular vesicles mixed with the biofluid sample before isolation;
wherein the recombinant extracellular vesicles incubated with PEG and the sample extracellular vesicles isolated in the same fraction after the isolation are incubated with immobilized anti-PEG antibodies so that the recombinant extracellular vesicles incubated with PEG are separated from the sample extracellular vesicles.

15. The method according to claim 14, wherein the anti-PEG antibodies are coated on magnetic beads.

16. A method of determining recovery rate of sample extracellular vesicles, the method comprising:
mixing a biofluid sample comprising a plasma sample or serum sample with a known amount of recombinant extracellular vesicles, wherein the recombinant extracellular vesicles comprise:
a) a self-assembling protein that directs its own release through vesicles as a luminal membrane-bound protein, and
b) a heterologous marker,
to obtain a mixture,
treating the mixture with a protease or incubating the recombinant extracellular vesicle with polyethylene glycol (PEG) so that the recombinant extracellular vesicles and the sample extracellular vesicles are present in the same fraction;
isolating the extracellular vesicles from the mixture comprising and/or combining with a density-based separation step resulting in obtaining a first fraction comprising the recombinant extracellular vesicles and a second fraction comprising the sample extracellular vesicles
detecting an amount of the recombinant extracellular vesicles among the isolated extracellular vesicles of the first fraction, and
determining the recovery rate of the sample extracellular vesicles based on a ratio of the amount of recombinant extracellular vesicles after isolation to the known amount of recombinant extracellular vesicles mixed with the biofluid sample before isolation;
wherein the protease is proteinase K.

17. The method according to claim 10, wherein the density-based separation is an iodixanol density gradient ultracentrifugation.

18. The method according to claim 10, wherein the density-based separation is preceded by an additional biophysical isolation step.

* * * * *